(12) United States Patent
Feingold et al.

(10) Patent No.: US 11,426,467 B2
(45) Date of Patent: Aug. 30, 2022

(54) DOSAGE REGIMES FOR THE ADMINISTRATION OF AN ANTI-CD25 ADC

(71) Applicants: ADC THERAPEUTICS SA, Epalinges (CH); MEDIMMUNE LIMITED, Cambridge (GB)

(72) Inventors: Jay Marshall Feingold, Murray Hill, NJ (US); Jens Wuerthner, Epalinges (CH)

(73) Assignees: ADC THERAPEUTICS SA, Epalinges (CH); MEDIMMUNE LIMITED, Cambridge (GB)

( * ) Notice: Subject to any disclaimer, the term of this patent is extended or adjusted under 35 U.S.C. 154(b) by 155 days.

(21) Appl. No.: 16/622,663

(22) PCT Filed: Jun. 14, 2018

(86) PCT No.: PCT/EP2018/065862
§ 371 (c)(1),
(2) Date: Dec. 13, 2019

(87) PCT Pub. No.: WO2018/229218
PCT Pub. Date: Dec. 20, 2018

(65) Prior Publication Data
US 2020/0405872 A1    Dec. 31, 2020

(30) Foreign Application Priority Data

Jun. 14, 2017 (GB) ..................... 1709439
Jun. 14, 2017 (GB) ..................... 1709441
(Continued)

(51) Int. Cl.
*A61K 47/68* (2017.01)
*A61K 47/54* (2017.01)
(Continued)

(52) U.S. Cl.
CPC ...... *A61K 47/6803* (2017.08); *A61K 31/5517* (2013.01); *A61K 39/3955* (2013.01);
(Continued)

(58) Field of Classification Search
CPC .............. A61K 47/6803; A61K 47/545; A61K 39/3955; A61K 31/5517; A61K 45/06; A61K 2039/545; A61P 35/00
See application file for complete search history.

(56) References Cited

U.S. PATENT DOCUMENTS 4,816,567 A    3/1989 Cabilly et al.
7,438,907 B2   10/2008 Schuurman et al.
(Continued)

FOREIGN PATENT DOCUMENTS

WO    2014057118 A1    4/2014
WO    2014057119 A1    4/2014
(Continued)

OTHER PUBLICATIONS

Polakis P. Antibody Drug Conjugates for Cancer Therapy. Pharmacol Rev. Jan. 2016;68(1):3-19. doi: 10.1124/pr.114.009373. PMID: 26589413 (Year: 2016).*
(Continued)

*Primary Examiner* — Joanne Hama
*Assistant Examiner* — Miles Joseph Delahoussaye
(74) *Attorney, Agent, or Firm* — Medler, Ferro, Woodhouse & Mills PLLC

(57) ABSTRACT

The present disclosure relates to novel dosage regimes for the treatment of pathological conditions, such as cancer, with Antibody Drug Conjugates (ADCs). In particular, the present disclosure relates to novel dosage regimes for the administration of ADCs which bind to CD25 (CD25-ADCS).

(Continued)

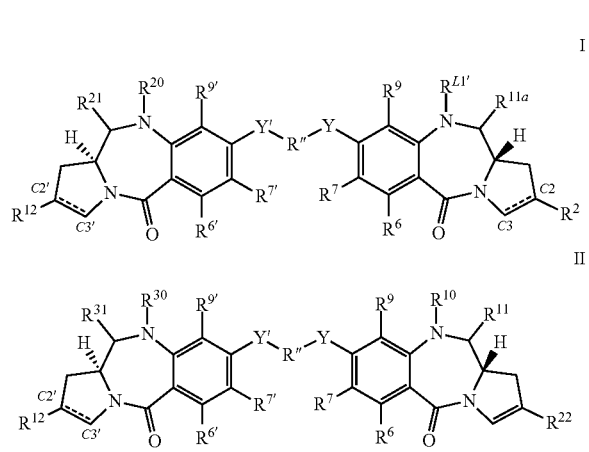

25 Claims, 4 Drawing Sheets

Specification includes a Sequence Listing.

(30) Foreign Application Priority Data

| Jun. 30, 2017 | (GB) | 1710493 |
|---|---|---|
| Jun. 30, 2017 | (GB) | 1710496 |
| Dec. 8, 2017 | (GB) | 1720541 |
| Dec. 8, 2017 | (GB) | 1720544 |
| Feb. 28, 2018 | (GB) | 1803298 |

(51) Int. Cl.
- A61P 35/00 (2006.01)
- A61K 31/5517 (2006.01)
- A61K 39/395 (2006.01)
- A61K 45/06 (2006.01)
- A61K 39/00 (2006.01)

(52) U.S. Cl.
CPC ............ *A61K 45/06* (2013.01); *A61K 47/545* (2017.08); *A61P 35/00* (2018.01); *A61K 2039/545* (2013.01)

(56) References Cited

U.S. PATENT DOCUMENTS

| 7,803,839 | B2 | 9/2010 | Aay et al. |
|---|---|---|---|
| 9,919,056 | B2 | 3/2018 | Van Berkel et al. |
| 9,931,414 | B2* | 4/2018 | Van Berkel et al. ........ A61K 39/395 |
| 9,931,415 | B2 | 4/2018 | Van Berkel et al. |
| 9,950,078 | B2 | 4/2018 | Howard et al. |
| 9,956,299 | B2 | 5/2018 | Howard et al. |
| 10,010,624 | B2 | 7/2018 | Howard et al. |
| 10,017,580 | B2 | 7/2018 | Van Berkel et al. |
| 10,695,433 | B2 | 6/2020 | Van Berkel et al. |
| 10,736,903 | B2 | 8/2020 | Van Berkel et al. |
| 10,751,346 | B2 | 8/2020 | Van Berkel et al. |
| 10,780,096 | B2* | 9/2020 | Van Berkel et al. ........ A61K 31/5517 |
| 2015/0273077 | A1 | 10/2015 | Van Berkel et al. |
| 2015/0283262 | A1* | 10/2015 | Van Berkel et al. ........ A61K 47/48561 |
| 2016/0256561 | A1 | 9/2016 | Howard et al. |
| 2018/0086828 | A1 | 3/2018 | Van Berkel et al. |
| 2018/0092985 | A1 | 4/2018 | Van Berkel et al. |
| 2018/0092986 | A1 | 4/2018 | Van Berkel et al. |
| 2018/0099055 | A1 | 4/2018 | Van Berkel et al. |
| 2018/0117172 | A1 | 5/2018 | Van Berkel et al. |
| 2018/0125994 | A1 | 5/2018 | Van Berkel et al. |
| 2018/0127505 | A1 | 5/2018 | Van Berkel et al. |
| 2018/0142025 | A1 | 5/2018 | Van Berkel |
| 2018/0303953 | A1 | 10/2018 | Van Berkel et al. |
| 2020/0405873 | A1 | 12/2020 | Feingold et al. |

FOREIGN PATENT DOCUMENTS

| WO | 2014057120 A1 | 4/2014 |
|---|---|---|
| WO | WO2014057119 A1 * | 4/2014 |
| WO | 2016083468 A1 | 6/2016 |
| WO | WO2016083468 A1 * | 6/2016 |
| WO | 2016166305 A1 | 10/2016 |
| WO | 2016166341 A1 | 10/2016 |
| WO | 2017020972 A1 | 2/2017 |
| WO | WO2017020972 A1 * | 2/2017 |

OTHER PUBLICATIONS

Govindan SV, Cardillo TM, Rossi EA, Trisal P, McBride WJ, Sharkey RM, Goldenberg DM. Improving the therapeutic index in cancer therapy by using antibody-drug conjugates designed with a moderately cytotoxic drug. Mol Pharm. Jun. 1, 2015;12(6):1836-47. doi: 10.1021/mp5006195. Epub Nov. 25, 2014. (Year: 2014).*
Flynn MJ et al. ADCT-301, a Pyrrolobenzodiazepine (PBD) Dimer-Containing Antibody-Drug Conjugate (ADC) Targeting CD25-Expressing Hematological Malignancies. Mol Cancer Ther. Nov. 2016;15(11):2709-2721doi: 10.1158/1535-7163.MCT-16-0233. Epub Aug. 17, 2016. PMID: 27535974 (Year: 2016).*
Cook AM, McDonnell AM, Lake RA, Nowak AK. Dexamethasone co-medication in cancer patients undergoing chemotherapy causes substantial immunomodulatory effects with implications for chemo-immunotherapy strategies. Oncoimmunology. 2015;5(3):e1066062. Published Sep. 16, 2015. (Year: 2015).*
Betts AM, Haddish-Berhane N, Tolsma J, Jasper P, King LE, Sun Y, Chakrapani S, Shor B, Boni J, Johnson TR. Preclinical to Clinical Translation of Antibody-Drug Conjugates Using PK/PD Modeling: a Retrospective Analysis of Inotuzumab Ozogamicin. AAPS J. Sep. 2016;18(5):1101-1116. (Year: 2016).*
Aue et al., "Fractionated subcutaneous rituximab is well-tolerated and preserves CD20 expression on tumor cells in patients with chronic lymphocytic leukemia," Haematologica 95(2):329-332 (2010).
Carter, P., "Potent antibody therapeutics by design," Nature Reviews Immunology 6(5):343-357 (2006).
Clackson et al., "Making antibody fragments using phage display libraries," Nature 352:624-628 (1991).
Frey et al., "Abstract 7002. Optimizing chimeric antigen receptor (CAR) T cell therapy for adult patients with relapsed or refractory (r/r) acute lymphoblastic leukemia (ALL)," Journal of Clinical Oncology 34(15_supplment):7002 (2016).
Hamann P., "Monoclonal antibody-drug conjugates," Expert Opinion on Therapeutic Patents 15(9):1087-1103 (2005).
Hartley J., "The development of pyrrolobenzodiazepines as antitumour agents," Expert Opinion on Investigational Drugs 20(6):733-744 (2011).
Hartley et al., "Pre-clinical pharmacology and mechanism of action of SG3199, the pyrrolobenzodiazepine (PBD) dimer warhead component of antibody-drug conjugate (ADC) payload tesirine," Scientific Reports 8(1):1-10 (2018).
Hartley J., "Antibody-drug conjugates (ADCs) delivering pyrrolobenzodiazepine (PBD) dimers for cancer therapy," Expert Opinion on Biological Therapy 21(7):931-943 (2020).
Johnston et al., "A Phase II trial of the oral mTOR inhibitor everolimus in relapsed Hodgkin lymphoma," American Journal of Hematology 85(5):320-324 (2010).
Kohler et al., "Continuous cultures of fused cells secreting antibody of predefined specificity," Nature 256:495-497 (1975).
Kouno et al., "Standardization of the Body Surface Area (BSA) Formula to Calculate the Dose of Anticancer Agents in Japan," Japanese Journal of Clinical Oncology, 33(6):309-313 (2003).

(56) References Cited

OTHER PUBLICATIONS

Kovtun et al., "Antibody-Drug Conjugates Designed to Eradicate Tumors with Homogeneous and Heterogeneous Expression of the Target Antigen," Cancer Research 66(6):3214-3221 (2006).
Lambert J., "Drug-conjugated monoclonal antibodies for the treatment of cancer," Current Opinion in Pharmacology 5(5):543-549 (2005).
Law et al., "Lymphocyte Activation Antigen CD70 Expressed by Renal Cell Carcinoma Is a Potential Therapeutic Target for Anti-CD70 Antibody-Drug Conjugates," Cancer Research 66(4):2328-2337 (2006).
Levi et al., "Detection of interleukin-2 receptors on tumor cells in formalin-fixed, paraffin-embedded tissues," Applied Immunohistochemistry 5(4):234-238 (1997).
Lonberg N., "Fully human antibodies from transgenic mouse and phage display platforms," Current Opinion in Immunology 20(4):450-459 (2008).
Marks et al., "By-passing Immunization, Human Antibodies from V-gene Libraries Displayed on Phage," Journal of Molecular Biology 222(3):581-597 (1991).
Merz et al., "ImmunoMax. A maximized immunohistochemical method for the retrieval and enhancement of hidden antigens," Laboratory Investigation 73(1):149-156 (1995).
Miller et al., "Design, Construction, and In Vitro Analyses of Multivalent Antibodies," Journal of Immunology 170(9):4854-4861 (2003).
Morrison et al., "Chimeric human antibody molecules: Mouse antigen-binding domains with human constant region domains," Proc. Natl. Acad. Sci. USA, 81(21):6851-6855 (1984).
Moskowitz et al., "Phase II study of bendamustine in relapsed and refractory Hodgkin lymphoma," Journal of Clinical Oncology, 31(4):456-460 (2013).
Nicolaou et al., "Calicheamicin $\theta$ 1I: A Rationally Designed Molecule with Extremely Potent and Selective DNA Cleaving Properties and Apoptosis Inducing Activity," Angewandte Chemie International Edition, 33(2):183-186 (1994).
Payne, G. "Progress in immunoconjugate cancer therapeutics," Cancer Cell 3(3):207-212 (2003).
Santoro et al., "Gemcitabine in the treatment of refractory Hodgkin's disease: results of a multicenter phase II study," Journal of Clinical Oncology 18(13):2615-2619 (2000).
Syrigos et al., "Antibody Directed Enzyme Prodrug Therapy (ADEPT): A Review of the Experimental and Clinical Considerations," Anticancer Research 19(1A):605-613 (1999).
Taksin et al., "High efficacy and safety profile of fractionated doses of Mylotarg as induction therapy in patients with relapsed acute myeloblastic leukemia: a prospective study of the alfa group," Leukemia 21(1):66-71 (2007).
Trail et al., "Monoclonal antibody drug immunoconjugates for targeted treatment of cancer," Cancer Immunology, Immunotherapy 52(5):328-337 (2003).
Van Heertum et al., "Lugano 2014 criteria for assessing FDG-PET/CT in lymphoma: an operational approach for clinical trials," Drug Design, Development and Therapy 11:1719-1728 (2017).
Vardiman et al., "The World Health Organization (WHO) classification of the myeloid neoplasms," Blood 100(7):2292-2302 (2002).
Wu et al., "Arming antibodies: prospects and challenges for immunoconjugates," Nature Biotechnology 23(9):1137-1146 (2005).
Xie et al., "In vivo behaviour of antibody-drug conjugates for the targeted treatment of cancer," Expert Opinion on Biological Therapy 6(3):281-291 (2006).

\* cited by examiner

SEQUENCES

SEQ ID NO. 1 (AB12 VH):
QVQLVQSGAEVKKPGSSVKVSCKASGGTFSRYIINWVRQAPGQGLEWMGRIIPILGVENYA
QKFQGRVTITADKSTSTAYMELSSLRSEDTAVYYCARKDWFDYWGQGTLVTVSSASTKGP
SVFPLA

SEQ ID NO. 2 (AB12 VL):
EIVLTQSPGTLSLSPGERATLSCRASQSVSSYLAWYQQKPGQAPRLLIYGASSRATGIPDRF
SGSGSGTDFTLTISRLEPEDFAVYYCQQYGSSPLTFGGGTKVEIKRTVAAPSVFIFP

SEQ ID NO. 3 (VH CDR1):
RYIIN

SEQ ID NO. 4 (VH CDR2):
RIIPILGVENYAQKFQG

SEQ ID NO. 5 (VH CDR3):
KDWFDY

SEQ ID NO. 6 (VL CDR1):
RASQSVSSYLA

SEQ ID NO. 7 (VL CDR2):
GASSRAT

SEQ ID NO. 8 (VL CDR3):
QQYGSSPLT

Figure 1

DOSAGE REGIMES FOR THE ADMINISTRATION OF AN ANTI-CD25 ADC

FIELD

The present disclosure relates to novel dosage regimes for the treatment of pathological conditions, such as cancer, with Antibody Drug Conjugates (ADCs). In particular, the present disclosure relates to novel dosage regimes for the administration of ADCs which bind to CD25 (CD25-ADCs).

BACKGROUND

Antibody Therapy

Antibody therapy has been established for the targeted treatment of subjects with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumour cells in the treatment of cancer, targets delivery of the drug moiety to tumours, and intracellular accumulation therein, whereas systemic administration of these unconjugated drug agents may result in unacceptable levels of toxicity to normal cells (Xie et al (2006) *Expert. Opin. Biol. Ther.* 6(3):281-291; Kovtun et al (2006) *Cancer Res.* 66(6): 3214-3121; Law et al (2006) *Cancer Res.* 66(4):2328-2337; Wu et al (2005) *Nature Biotech.* 23(9):1137-1145; Lambert J. (2005) *Current Opin. in Pharmacol.* 5:543-549; Hamann P. (2005) *Expert Opin. Ther. Patents* 15(9):1087-1103; Payne, G. (2003) *Cancer Cell* 3:207-212; Trail et al (2003) *Cancer Immunol. Immunother.* 52:328-337; Syrigos and Epenetos (1999) *Anticancer Research* 19:605-614).

CD25

The type I transmembrane protein CD25 is present on activated T- and B-cells, some thymocytes, myeloid precursors, and oligodendrocytes. On activated T-cells, it forms heterodimers with the beta- and gamma subunits (CD122 and CD132), thus comprising the high-affinity receptor for IL-2. This ligand represents a survival factor for activated T-cells, as removal of IL-2 leads to immediate death of these cells.

In case of B-cells, CD25 is physiologically expressed in early developmental stages of late pro-B and pre-B cells. Malignancies arising from this stage of B-cell differentiation may thus also express CD25. Mast cell lesions are also positive for CD25 which is thus considered as a key diagnostic criterion for determination of systemic mastocytosis. In Hodgkin lymphomas, CD25 is reported to be not expressed in Hodgkin-/Reed-Sternberg cells in nodular lymphocyte predominance Hodgkin lymphoma (NLPHL), whereas the same cell type expresses CD25 at varying levels in classical Hodgkin' lymphomas of mixed cellularity type. The general expression levels are reported to be lower than in tumor infiltrating lymphocytes (TILs), which may result in problems demonstrating CD25 tumor cells in these cases (Levi et al., Merz et al, 1995).

Expression of the target antigen has also been reported for several B- and T-cell-derived subtypes of non-Hodgkin-lymphomas, i.e. B-cell chronic lymphatic leukaemia, hairy cell leukaemia, small cell lymphocytic lymphoma/chronic lymphocytic leukaemia as well as adult T-cell leukaemia/lymphoma and anaplastic large cell lymphoma.

CD25 may be localised to the membrane, with some expression observed in the cytoplasm. Soluble CD25 may also be observed outside of cells, such as in serum.

Therapeutic Uses of Anti-CD25 ADCs

The efficacy of an Antibody Drug Conjugate comprising an anti-CD25 antibody (an anti-CD25-ADC) in the treatment of, for example, cancer has been described—see, for example, WO2014/057119, WO2016/083468, and WO2016/166341.

Research continues to further improve the efficacy, tolerability, and clinical utility of anti-CD25 ADCs. To this end, the present authors have identified clinically advantageous dosage regimes for the administration of an anti-CD25 ADC.

SUMMARY

Through treatment of subjects with CD25-ADC, the present authors have developed dosage regimes that allow for improved efficacy, efficiency, and/or tolerability of CD25-ADC treatment. Interesting, it was found that the parameters required for optimal treatment efficacy, efficiency, and/or tolerability differed between indication subsets.

Leukemias

During treatment of a cohort of human subjects with relapsed or refractory CD25+ acute myeloid leukemia (AML) using a single dose of CD25-ADC per 3-week treatment cycle, the present authors noted a group of subjects where there was a transient significant decrease in their peripheral and bone marrow myeloblast count followed by an increase in myeloblast count prior to the scheduled subsequent dose. This observation was coupled with pharmokinetic (PK) analysis indicating that the administered CD25-ADC was rapidly eliminated from subjects' circulations.

Accordingly, the present authors sought an altered dosage regime to improve the efficacy of CD25-ADC treatment. Data collected from a number of different mouse xenograft models of CD25+ proliferative disease indicated that administration of CD25-ADC as a single dose on day 1 of the treatment cycle led to effective treatment, with administration of an identical total dose of AD25-ADC as a series of smaller partial doses resulting in higher mortality levels (see FIGS. 2 and 3).

Nonetheless, the present authors reasoned that fractionating the dose of the CD25-ADC and administering it at more regular intervals throughout the treatment cycle would result in improved efficacy of drug exposure being maintained throughout the treatment cycle. Furthermore, by employing a fractionated dosage regime, more consistent exposure throughout the dosage interval and decreased peak levels are expected to reduce toxicity associated with peak exposure levels.

Without wishing to be bound by theory, the use of such fractionated dosage regimes is potentially especially advantageous in diseases such as acute leukaemia, where the rapid production of circulating myeloblasts acts as an antigenic sink for the CD25-ADC. In addition, normal T-reg cells express CD25 and so may also act as antigenic sink contributing to the rapid clearance of the ADC. Moreover, the direct access of the CD25-ADC to the site of action afforded by presence of leukemic myeloblasts primarily in the systemic circulation allows for the ready maintenance of effective drug concentrations at the site of action through fractionated dosing. This is consistent with the exploration or adoption of fractionated dosage regimes in some other treatments of subjects with leukaemia (Frey F, et al. Abstract 7002. Presented at: ASCO Annual Meeting; Jun. 3-7, 2016; Chicago; Aue G, et al. Haematologica February 2010 95: 329-332; Taksin A, et al. Leukemia (2007) 21, 66-71. Published online 19 Oct. 2006).

Accordingly, the part of the subject-matter of the present disclosure concerns the use of CD25-ADCs in fractionated dosage regimes for treating disease, for example, proliferative diseases. These fractionated regimes are expected to be associated with a range of clinical benefits, including improved efficacy, reduced toxicity and side-effects, and the consequent expansion of the population eligible to be treated to include subjects intolerant of the greater side effects of known dosage regimes.

In a first aspect the disclosure provides a method of treating a proliferative disease in a subject, said method comprising administering to a subject a CD25-ADC, wherein the CD25-ADC is administered to the subject in a fractionated dosage regime.

The CD25-ADC may be ADCX25 as described herein.

The term "fractionated dosage regime" is used herein to describe a dosage regime in which the total dose of CD25-ADC administered during the treatment cycle is administered in a series of two or more partial doses during the treatment cycle. The term 'partial dose' is used herein to denote a dose of ADC that is a fraction of the total dose of ADC to be administered in the treatment cycle. The sum of all partial doses delivered in a treatment cycle equals the total dose. A fractionated dosage regime contrasts with a 'single-dose' dosing regime in which the total dose of CD25-ADC administered in the treatment cycle is administered as a single dose at the start of the treatment cycle.

Preferably the total dose of CD25-ADC is administered as partial doses of equal size regularly spaced throughout the treatment cycle. Administration to the subject once per week is particularly preferred. In some cases the total dose of CD25-ADC is administered over a three week treatment cycle in 3 equal partial doses, with a partial dose administered once a week. For example, with administration of a partial dose on days 1, 8, and 15 of a 3-week treatment cycle. Further features of fractionated dosage regimes are discussed herein.

The subject may be human. The subject may have cancer, or may have been determined to have cancer. The subject may have, or have been determined to have, a CD25+ cancer or CD25+ tumour-associated non-tumour cells, such as CD25+ infiltrating T-cells.

Preferably, the fractionated dosage regimes described here are employed when the subject has, is suspected of having, or have been diagnosed with leukaemia. For example, the subject may have, may be suspected or having, or may have been diagnosed with Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL).

The proliferative disease may be CD25+AML.

The proliferative disease may be CD25+ALL.

In other, less-preferred embodiments, the subject may have, may be suspected or having, or may have been diagnosed with lymphoma. For example, with non-Hodgkin's Lymphoma, such as diffuse large B-cell lymphoma (DLBCL), follicular lymphoma, (FL), Mantle Cell lymphoma (MCL), chronic lymphatic lymphoma (CLL), and Marginal Zone B-cell lymphoma (MZBL).

The proliferative disease may be resistant, relapsed or refractory.

In some cases the subject has been diagnosed as having the proliferative disease prior to the start of treatment with the CD25-ADC.

In some cases the method further comprises administering a second anti-cancer compound in combination with the CD25-ADC.

In some cases the fractional dosage regime reduces the treatment toxicity or side-effects as compared to a single dose per treatment cycle regime.

In some cases the fractional dosage regime increases the treatment efficacy as compared to a single dose per treatment cycle regime.

In some cases the CD25-ADC is administered intravenously.

In a second aspect, the present disclosure provides a method of reducing the toxicity and/or side effects associated with administration of a CD25-ADC to a subject, the method comprising administering the CD25-ADC in a fractionated dosage regime as defined herein.

In a third aspect, the present disclosure provides a method of increasing the treatment efficacy associated with administration of an CD25-ADC to a subject, the method comprising administering the CD25-ADC in a fractionated dosage regime as defined herein.

In a fourth aspect, the present disclosure provides a method of selecting a subject for treatment by a fractionated dosage regime as described herein, which selection method comprises selecting for treatment subjects that express CD25 in a tissue of interest.

In a fifth aspect the present disclosure provides a packaged pharmaceutical product comprising a CD25-ADC as described herein in combination with a label or insert advising that the CD25-ADC should be administered in a fractionated dosage regime.

The disclosure also provides a kit comprising:
a first medicament comprising a CD25-ADC; and, optionally,
a package insert or label comprising instructions for administration of the CD25-ADC in a fractionated dosage regime as described herein..

In a sixth aspect the present disclosure provides a CD25-ADC as defined herein for use in a method of treatment as described herein.

In a seventh aspect the present disclosure provides the use of a CD25-ADC as defined herein in the preparation of a medicament for use in a method of treatment as described herein.

Lymphomas

During treatment of a cohort of subjects with Relapsed or Refractory Non-Hodgkin Lymphoma using a single dose of ADC per 3-week treatment cycle, the present authors noted that that repetitive dosing every three weeks is not well tolerated or necessary at doses of 120 µg/kg and higher:

Of six responding patients treated at 120 µg/kg (four complete remissions, two partial remissions), four required at least one dose delay during treatment (3 to 7 treatment cycles) due to adverse events and two were discontinued from treatment.

Of three patients treated at 150 µg/kg received 2 to 3 treatment cycles of ADC before side effects necessitated dose delay. The delay eventually led to removal from the study since the toxicities were slow to resolve.

Of 6 patients treated at 200 µg/kg, five attained complete response and the other attained partial response. However, all patients had some evidence of toxicity at the end of the second or third treatment cycle.

In addition, pharmacokinetic studies indicate that ADC is not rapidly cleared from the bloodstream, with trough levels at the end of each 3-week treatment cycle maintained at a relatively high level, or even gradually increasing with each treatment cycle.

Accordingly, the present authors reasoned that tapering the dose of the ADC and/or increasing the length of each treatment cycle would allow for more effective long term treatment of subjects having lymphoma by providing reasonable exposure to ADC to provide efficacy while maximizing long term tolerability through reducing ADC accumulation.

Accordingly, part of the subject-matter of the present disclosure concerns the use of ADCs in tapered and/or elongated dosage regimes for treating proliferative diseases, in particular lymphomas. These tapered and/or elongated regimes are expected to be associated with a range of clinical benefits, including reduced toxicity and side-effects, and the consequent expansion of the population eligible to be treated to include subjects intolerant of the side effects of known dosage regimes.

Preferably, the tapered and/or elongated dosage regimes described here are employed when the subject has, is suspected of having, or have been diagnosed with a lymphoma. For example, the subject may have, may be suspected or having, or may have been diagnosed with Hodgkin Lymphoma, or a non-Hodgkin's Lymphoma (NHL). NHL includes lymphomas from both:
(1) B-cell lineages, such as diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL); and
(2) T-cell lineages, such as Extranodal T cell lymphoma, Cutaneous T-cell lymphomas (Sézary syndrome and Mycosis fungoides), Anaplastic large cell lymphoma, T-cell lymphoblastic lymphoma, including acute T-cell lymphoblastic lymphoma (ATLL), and Angioimmunoblastic T-cell lymphoma.

In an eighth aspect the disclosure provides a method of treating a proliferative disease in a subject, said method comprising administering to a subject a CD25-ADC, wherein the CD25-ADC is administered to the subject in a tapered and/or elongated dosage regime.

The CD25-ADC may be ADCx25 as described herein.

The term "tapered dosage regime" is used herein to describe a dosage regime in which the total dose of CD25-ADC administered in the first treatment cycle (from hereon in termed the "starting dose") is greater than the total dose of CD25-ADC administered in one or more subsequent treatment cycle. A tapered dosage regime contrasts with a constant dosing regime in which the starting dose is the same as the total dose administered in each subsequent treatment cycle (see 'Constant' in Table 1, below).

In some cases, the administered dose is only reduced if the subject has attained at least Stable Disease [SD] at the end of the preceding treatment cycle (i.e. SD or better response, such as PR or CR).

Preferably the starting dose is reduced no more than once during the treatment of a subject. In these cases the total dose following dose reduction is from hereon in termed the "reduced dose".

In some cases the dose is reduced following the first treatment cycle. That is, the starting dose is administered in the first treatment cycle and the reduced dose is administered in the second and subsequent treatment cycles. Dosing regime 'Taper 6' in Table 1 is an example of such a dosing regime.

In some cases the dose is reduced following the second treatment cycle. That is, the starting dose is administered in each of the first and second treatment cycles and the reduced dose is administered in each of the third and subsequent treatment cycles. Dosing regime 'Taper 3', 'Taper 4', 'Taper 5', and 'Taper 10' in Table 1 are examples of such a dosing regime.

In some cases the dose is reduced following the third treatment cycle. That is, the starting dose is administered in each of the first, second, and third treatment cycles and the reduced dose is administered in each of the fourth and subsequent treatment cycles. Dosing regime 'Taper 8' and 'Taper 9' are examples of such a dosing regime.

In some cases the starting dose is at least 120 µg/kg. In some cases the starting dose is at least 150 µg/kg, such as at least 200 µg/kg. In some cases the starting dose is about 45, 60, 80, 120, 150, or 200 µg/kg. In some cases the reduced dose is about 30, 40 or 60 µg/kg. In some cases the starting dose is about 200 µg/kg and the reduced dose is about 60 µg/kg. In some cases the starting dose is about 45 µg/kg and the reduced dose is about 30 µg/kg. In some cases the starting dose is about 60 µg/kg and the reduced dose is about 30 µg/kg. In some cases the starting dose is about 80 µg/kg and the reduced dose is about 40 µg/kg.

In some cases the length of each treatment cycle is 3 weeks.

In some cases the length of each treatment cycle is 6 weeks.

The term "elongated dosage regime" is used herein to describe a dosage regime in which the length of the first treatment cycle (from hereon in termed the "starting length") is shorter than the length of one or more subsequent treatment cycles. An elongated dosage regime contrasts with a constant dosing regime in which the starting length is the same as the length of each subsequent treatment cycle (see 'Constant' in Table 2, below).

In some cases, the treatment cycle length is only increased if the subject has attained at least Stable Disease [SD] at the end of the preceding treatment cycle.

Preferably the treatment cycle length is increased no more than once during the treatment of a subject. In these cases the treatment cycle length following length increase is from hereon in termed the "increased length".

In some cases the cycle length is increased following the first treatment cycle. That is, the first treatment cycle is the starting length, and each of the second and subsequent treatment cycles is the increased length. Dosing regime 'Long 4' in Table 2 is an example of such a dosing regime.

In some cases the cycle length is increased following the second treatment cycle. That is, each of the first and second treatment cycles is the starting length, and each of the third and subsequent treatment cycles is the increased length. Dosing regime 'Long 3' in Table 2 is an example of such a dosing regime.

In some cases the starting length is 3 weeks. In some cases the increased length is 6 weeks.

Preferably, in a tapered and elongated dosage regime the starting dose is reduced no more than once and the treatment cycle length is increased no more than once during the treatment of a subject.

In some cases, the administered dose is only reduced and/or the cycle length increased if the subject has attained at least Stable Disease [SD] at the end of the preceding treatment cycle.

In some cases the dose reduction and the length increase is made following the second treatment cycle. That is, each of the first and second treatment cycles have the starting dose and the starting length, and each of the third and subsequent treatment cycles have the reduced dose and increased length.

In some cases the starting dose is at least 120 µg/kg. In some cases the starting dose is at least 150 µg/kg, such as at least 200 µg/kg. In some cases the starting dose is about 120, 150, or 200 µg/kg. In some cases the reduced dose is about 60 µg/kg. In some cases the starting length is 3 weeks and the increased length is 6 weeks. In some cases the starting dose and starting length are respectively about 120 µg/kg and three weeks and the reduced dose and increased length are respectively about 60 µg/kg and six weeks. In some cases the starting dose and starting length are respectively about 150 µg/kg and three weeks and the reduced dose and increased length are respectively about 60 µg/kg and six weeks.

The subject may be human. The subject may have cancer, or may have been determined to have cancer. The subject may have, or have been determined to have, a CD25+ cancer or CD25+ tumour-associated non-tumour cells, such as CD25+ infiltrating cells.

Preferably, the tapered and/or elongated dosage regimes described here are employed when the subject has, is suspected of having, or have been diagnosed with a lymphoma. For example, the subject may have, may be suspected or having, or may have been diagnosed with a Hodgkin Lymphoma, or a non-Hodgkin's Lymphoma (NHL). NHL includes lymphomas from both:
(1) B-cell lineages, such as diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL); and
(2) T-cell lineages, such as Extranodal T cell lymphoma, Cutaneous T-cell lymphomas (Sézary syndrome and Mycosis fungoides), Anaplastic large cell lymphoma, T-cell lymphoblastic lymphoma, including acute T-cell lymphoblastic lymphoma (ATLL), and Angioimmunoblastic T-cell lymphoma.

The subject may have, or have been determined to have Relapsed or Refractory Hodgkin Lymphoma.

In some cases the subject has been diagnosed as having the proliferative disease prior to the start of treatment with the CD25-ADC.

In some cases the method further comprises administering a second anti-cancer compound in combination with the CD25-ADC.

In some cases the tapered and/or elongated dosage regime reduces the treatment toxicity or side-effects as compared to a constant dose level and cycle length regime.

In some cases the tapered and/or elongated dosage regime increases the treatment efficacy as compared to a constant dose level and cycle length regime.

In some cases the CD25-ADC is administered intravenously.

In a ninth aspect, the present disclosure provides a method of reducing the toxicity and/or side effects associated with administration of a CD25-ADC to a subject, the method comprising administering the CD25-ADC in a tapered and/or elongated dosage regime as defined herein.

In a tenth aspect, the present disclosure provides a method of increasing the treatment efficacy associated with administration of an CD25-ADC to a subject, the method comprising administering the CD25-ADC in tapered and/or elongated dosage regime as defined herein.

In a eleventh aspect, the present disclosure provides a method of selecting a subject for treatment by a tapered and/or elongated dosage regime as described herein, which selection method comprises selecting for treatment subjects that express CD25 in a tissue of interest.

In a twelfth aspect the present disclosure provides a packaged pharmaceutical product comprising a CD25-ADC as described herein in combination with a label or insert advising that the CD25-ADC should be administered in a tapered and/or elongated dosage regime.

The disclosure also provides a kit comprising:
a first medicament comprising a CD25-ADC; and, optionally,
a package insert or label comprising instructions for administration of the CD25-ADC in tapered and/or elongated dosage regime as described herein.

In a thirteenth aspect the present disclosure provides a CD25-ADC as defined herein for use in a method of treatment as described herein.

In a fourteenth aspect the present disclosure provides the use of a CD25-ADC as defined herein in the preparation of a medicament for use in a method of treatment as described herein.

DETAILED DISCLOSURE

As described in more detail below, the present authors have reasoned that CD25-ADCs as defined herein, when administered in a fractionated dosage regime, have improved efficacy and/or reduced toxicity for treating leukaemias as compared to that observed when an equivalent amount of ADC is administered as a single dose.

Thus, in a first aspect the disclosure provides a method of treating a proliferative disease in a subject, said method comprising administering to a subject a CD25-ADC, wherein the CD25-ADC is administered to the subject in a fractionated dosage regime.

Further, the present authors have reasoned that CD25-ADCs as defined herein, when administered in tapered and/or elongated dosage regimes, have improved efficacy and/or reduced toxicity for treating lymphomas as compared to that observed when an ADC is administered in a regime with constant dosage size and treatment cycle length.

Thus, in an eighth aspect the disclosure provides a method of treating a proliferative disease in a subject, said method comprising administering to a subject a CD25-ADC, wherein the CD25-ADC is administered to the subject in a tapered and/or elongated dosage regimes.

These findings provide additional utilities for such CD25-ADCs, implying new therapeutic contexts for use, for example in relation to patient groups with heightened sensitivity to CD25-ADC toxicity, or in relation to patient groups requiring larger doses of CD25-ADC for effective treatment.

Anti-CD25 ADCs

As used herein, the term "CD25-ADC" refers to an ADC in which the antibody component is an anti-CD25 antibody. The term "PBD-ADC" refers to an ADC in which the drug component is a pyrrolobenzodiazepine (PBD) warhead. The term "anti-CD25-ADC" refers to an ADC in which the antibody component is an anti-CD25 antibody, and the drug component is a PBD warhead.

The CD25-ADC may comprise a conjugate of formula $L-(D^L)_p$, where $D^L$ is of formula I or II:

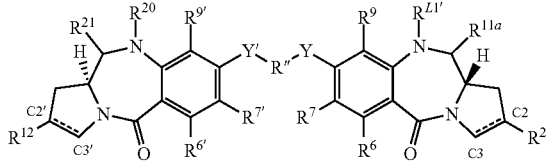

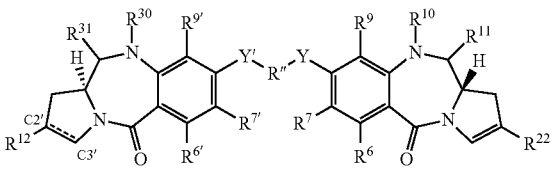

wherein:

L is an antibody (Ab) which is an antibody that binds to CD25;

when there is a double bond present between C2' and C3', $R^{12}$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id) 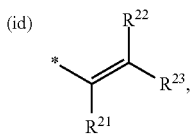

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie) 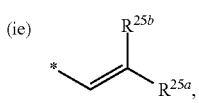

wherein one of $R^{25a}$ and $R^{25b}$ is H and the other is selected from: phenyl, which phenyl is optionally substituted by a group selected from halo, methyl, methoxy; pyridyl; and thiophenyl; and (if) 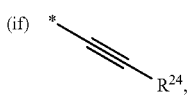

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is

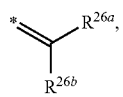

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester; $R^{6}$ and $R^{9}$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;

$R^{7}$ is selected from H, R, OH, OR, SH, SR, $NH_2$, NHR, NHRR', nitro, $Me_3Sn$ and halo;

R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^{6}$, $R^{7}$ and $R^{9}$ respectively;

[Formula I]

$R^{L1'}$ is a linker for connection to the antibody (Ab);

$R^{11a}$ is selected from OH, $OR^{A}$, where $R^{A}$ is $C_{1-4}$ alkyl, and $SO_zM$, where z is 2 or 3 and M is a monovalent pharmaceutically acceptable cation;

$R^{20}$ and $R^{21}$ either together form a double bond between the nitrogen and carbon atoms to which they are bound or;

$R^{20}$ is selected from H and $R^{C}$, where $R^{C}$ is a capping group;

$R^{21}$ is selected from OH, $OR^{A}$ and $SO_zM$;

when there is a double bond present between C2 and C3, $R^{2}$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id) 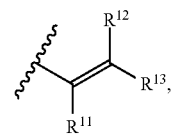

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^{2}$ group is no more than 5;

(ie) 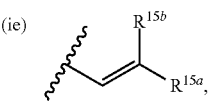

wherein one of $R^{15a}$ and $R^{15b}$ is H and the other is selected from: phenyl, which phenyl is optionally substituted by a group selected from halo, methyl, methoxy; pyridyl; and thiophenyl; and (if) 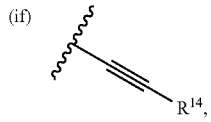

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is

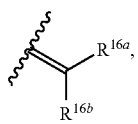

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula IIIa, formula IIIb or formula IIIc:

(a) 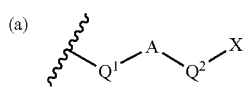 IIIa where A is a $C_{57}$ aryl group, and either (i) $Q^1$ is a single bond, and $Q^2$ is selected from a single bond and $-Z-(CH_2)_n-$, where Z is selected from a single bond, O, S and NH and n is from 1 to 3; or (ii) $Q^1$ is $-CH=CH-$, and $Q^2$ is a single bond;

(b) 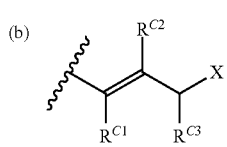 IIIb where;

$R^{C1}$, $R^{C2}$ and $R^{C3}$ are independently selected from H and unsubstituted $C_{1-2}$ alkyl;

(c) 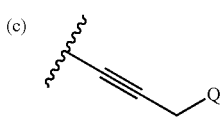 IIIc where Q is selected from $O-R^{L2'}$, $S-R^{L2'}$ and $NR^N-R^{L2'}$, and $R^N$ is selected from H, methyl and ethyl X is selected from the group comprising: $O-R^{L2'}$, $S-R^{L2'}$, $CO_2-R^{L2'}$, $CO-R^{L2'}$, $NH-C(=O)-R^{L2'}$, $NHNH-R^{L2'}$, $CONHNH-R^{L2'}$,

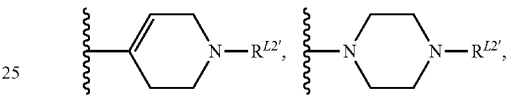

$NR^N R^{L2'}$, wherein $R^N$ is selected from the group comprising H and $C_{1-4}$ alkyl;

$R^{L2'}$ is a linker for connection to the antibody (Ab);

$R^{10}$ and $R^{11}$ either together form a double bond between the nitrogen and carbon atoms to which they are bound or;

$R^{10}$ is H and $R^{11}$ is selected from OH, $OR^A$ and $SO_zM$;

$R^{30}$ and $R^{31}$ either together form a double bond between the nitrogen and carbon atoms to which they are bound or;

$R^{30}$ is H and $R^{31}$ is selected from OH, $OR^A$ and $SO_zM$.

In some embodiments $L-R^{L1'}$ or $L-R^{L2'}$ is a group:

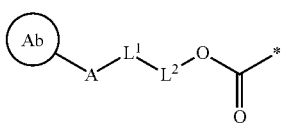

where the asterisk indicates the point of attachment to the PBD, Ab is the antibody, $L^1$ is a cleavable linker, A is a connecting group connecting $L^1$ to the antibody, $L^2$ is a covalent bond or together with $-OC(=O)-$ forms a self-immolative linker.

In some of these embodiments, $L^1$ is enzyme cleavable.

It has previously been shown that such ADCs are useful in the treatment of CD25 expressing cancers (see, for example, WO2014/057119, which is incorporated by reference herein in its entirety).

The term anti-CD25-ADC may include any embodiment described in WO 2014/057119. In particular, in preferred embodiments the ADC may have the chemical structure:

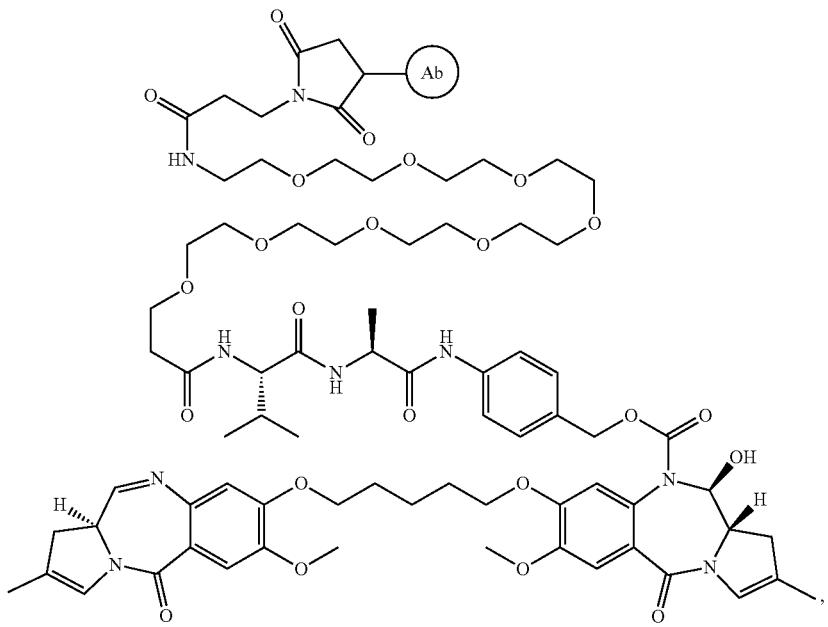

where the Ab is a CD25 antibody, and the DAR is between 1 and 8.

The antibody may comprise a VH domain comprising a VH CDR1 with the amino acid sequence of SEQ ID NO:3, a VH CDR2 with the amino acid sequence of SEQ ID NO:4, and a VH CDR3 with the amino acid sequence of SEQ ID NO:5.

In some aspects the antibody component of the anti-CD25-ADC is an antibody comprising: a VH domain comprising a VH CDR1 with the amino acid sequence of SEQ ID NO:3, a VH CDR2 with the amino acid sequence of SEQ ID NO:4, and a VH CDR3 with the amino acid sequence of SEQ ID NO:5. In some embodiments the antibody comprises a VH domain having the sequence according to SEQ ID NO:1.

The antibody may further comprise: a VL domain comprising a VL CDR1 with the amino acid sequence of SEQ ID NO:6, a VL CDR2 with the amino acid sequence of SEQ ID NO:7, and a VL CDR3 with the amino acid sequence of SEQ ID NO:8. In some embodiments the antibody further comprises a VL domain having the sequence according to SEQ ID NO:2.

In some embodiments the antibody comprises a VH domain and a VL domain, the VH and VL domains having the sequences of SEQ ID NO:1 paired with SEQ ID NO:2.

The VH and VL domain(s) may pair so as to form an antibody antigen binding site that binds CD25.

In preferred embodiments the antibody is an intact antibody comprising a VH domain and a VL domain, the VH and VL domains having sequences of SEQ ID NO:1 and SEQ ID NO:2.

In some embodiments the antibody is a fully human monoclonal IgG1 antibody, preferably IgG1,κ.

In some embodiments the antibody is the AB12 antibody described in WO 2004/045512 (Genmab A/S).

In an aspect the antibody is an antibody as described herein which has been modified (or further modified) as described below. In some embodiments the antibody is a humanised, deimmunised or resurfaced version of an antibody disclosed herein.

The preferred anti-CD25-ADC for use with the aspects of the present disclosure is ADCX25, as described herein below.

ADCx25

ADCx25 is an antibody drug conjugate composed of a human antibody against human CD25 attached to a pyrrolobenzodiazepine (PBD) warhead via a cleavable linker. The mechanism of action of ADCX25 depends on CD25 binding. The CD25 specific antibody targets the antibody drug conjugate (ADC) to cells expressing CD25. Upon binding, the ADC internalizes and is transported to the lysosome, where the protease sensitive linker is cleaved and free PBD dimer is released inside the target cell. The released PBD dimer inhibits transcription in a sequence-selective manner, due either to direct inhibition of RNA polymerase or inhibition of the interaction of associated transcription factors. The PBD dimer produces covalent crosslinks that do not distort the DNA double helix and which are not recognized by nucleotide excision repair factors, allowing for a longer effective period (Hartley 2011). These DNA crosslinks cause strand breaks when the DNA replication fork reaches them, leading to apoptosis induction.

It has the chemical structure:

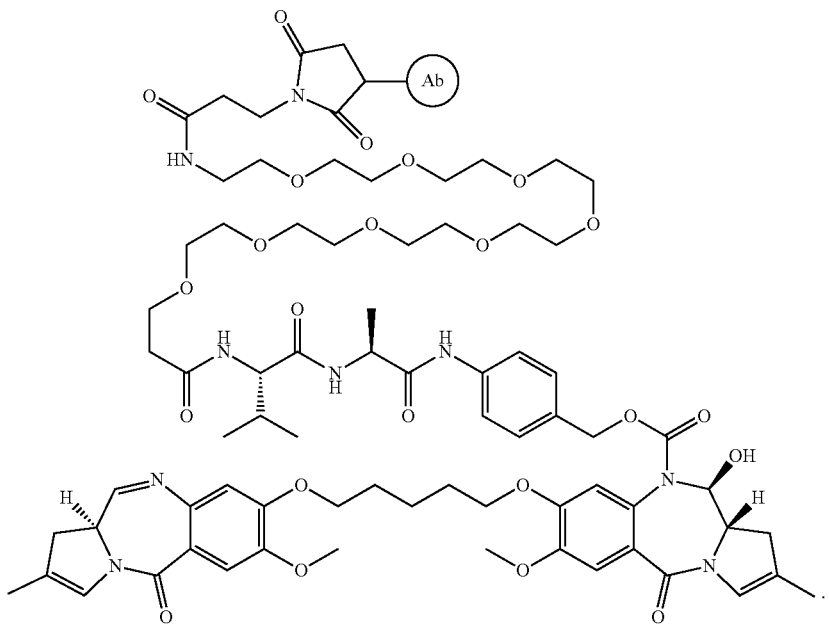

Ab represents Antibody AB12 (fully human monoclonal IgG1, K antibody with the VH and VL sequences SEQ ID NO:1 and SEQ ID NO:2, respectively, also known as HuMax-TAC). It is synthesised as described in WO 2014/057119 (Conj AB12-E) and typically has a DAR (Drug to Antibody Ratio) of 2.0+/−0.3.

CD25 Binding

As used herein, "binds CD25" is used to mean the antibody binds CD25 with a higher affinity than a non-specific partner such as Bovine Serum Albumin (BSA, Genbank accession no. CAA76847, version no. CAA76847.1 GI:3336842, record update date: Jan. 7, 2011 02:30 PM). In some embodiments the antibody binds CD25 with an association constant ($K_a$) at least 2, 3, 4, 5, 10, 20, 50, 100, 200, 500, 1000, 2000, 5000, 104, 105 or $10^6$-fold higher than the antibody's association constant for BSA, when measured at physiological conditions. The antibodies of the disclosure can bind CD25 with a high affinity. For example, in some embodiments the antibody can bind CD25 with a $K_D$ equal to or less than about $10^{-6}$ M, such as equal to or less than one of $1\times10^{-6}$, $10^{-7}$, $10^{-8}$, $10^{-9}$, $10^{-10}$, $10^{-11}$, $10^{-12}$, $10^{-13}$ or $10^{-14}$.

In some embodiments, CD25 polypeptide corresponds to Genbank accession no. NP_000408, version no. NP_000408.1 GI:4557667, record update date: Sep. 9, 2012 04:59 PM. In one embodiment, the nucleic acid encoding CD25 polypeptide corresponds to Genbank accession no. NM_000417, version no. NM_000417.2 GI:269973860, record update date: Sep. 9, 2012 04:59 PM. In some embodiments, CD25 polypeptide corresponds to Uniprot/Swiss-Prot accession No. P01589.

Fractionated Dosage Regimes

The term "fractionated dosage regime" is used herein to describe a dosage regime in which the total dose of CD25-ADC administered during the treatment cycle is administered in a series of two or more partial doses during the treatment cycle. The term 'partial dose' is used herein to denote a dose of ADC that is a fraction of the total dose of ADC to be administered in the treatment cycle. The sum of all partial doses delivered in a treatment cycle equals the total dose. A fractionated dosage regime contrasts with a 'single-dose' dosing regime in which the total dose of CD25-ADC administered in the treatment cycle is administered as a single dose at the start of the treatment cycle.

For example, in an example single-dose dosing regime for a CD25-ADC, 100% of the total dose of CD25-ADC administered during the treatment cycle is administered on day 1 of a 3-week treatment cycle. The subject is then monitored throughout the cycle and the subject's level of response used to decide if the treatment cycle should be repeated, stopped, or amended. In contrast, a fractionated dosage regime may involve administering only 33% of the total dose of ADC administered during the treatment cycle on day 1 of a 3-week treatment cycle, with a further 33% administered on day 8, and the final 33% administered on day 15.

The total dose administered may be fractionated into any number of separate doses, with the number being determined according to the clinical requirements of the subject. For example, the total dose administered may be fractionated into 2, 3, 4, 5, 6, 7, 8, 9, 10 or more than 10 doses.

The amount of CD25-ADC administered in each partial dose may be the same or different. So, for example, a total dose of 100 units of ADC delivered in 3 partial doses may be delivered as (1×50 units, 1×30 units, and 1×20 units) or (3×33⅓ units). Preferably all of the partial doses contain the same amount of CD25-ADC i.e. all of the partial doses are of equal size.

The time interval between one partial dose and the next partial dose may be the same as, or different to, the time interval between the one partial dose and the preceding partial dose. Preferably, the time interval between one partial dose and the next partial dose is the same as the time interval between the one partial dose and the preceding partial dose. That is, preferably the administration of the partial doses is regularly spaced throughout the treatment cycle. An example of such regular administration is the administration of 3 partial doses on days 1, 8, and 15 of a 3-week (i.e. 21 day) treatment cycle.

The length of the treatment cycle may vary depending upon the pharmokinetics (PK) of the CD25-ADC and the clinical requirements of the subject. The treatment cycle may be 1 week, 2 weeks, 3 weeks, 4 weeks, 5 weeks, 6 weeks, 7 weeks, 8 weeks, or 9 weeks. Preferably the treatment cycle is 3 weeks or 6 weeks, with 3 weeks being particularly preferred.

The total dose of CD25-ADC administered during the treatment cycle may vary according to the clinical requirements of the subject. For example, the total dose may be about 10, 20, 30, 40, 50, 60, 70, 80, 90, 100, 120, 150, 200, 250, or 300 µg/kg. In some cases the total dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240 µg/kg, 241 to 260 µg/kg, 261 to 280 µg/kg, or 281 to 300 µg/kg.

The size of the partial dose will depend upon the total dose of CD25-ADC administered during the treatment cycle, and the number of partial doses into which the total dose it is divided, and the relative sizes of the partial doses. In some cases each partial dose is of equal size. In some cases the partial dose is about 3, 10, 20, 30, 37.5, 40, 42.5, 45, 47.5, 50, 60, 70, 80, 90, or 100 µg/kg. In some the partial dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, or 91 to 100 µg/kg.

Preferably the total dose of CD25-ADC is administered as partial doses of equal size regularly spaced throughout the treatment cycle. Administration to the subject once per week is particularly preferred. Each partial dose may be 37.5, 40, 42.5, 45, 47.5, or 50 µg/kg. Preferably, each partial dose is about 40 to 60 µg/kg, such as about 45 to 55 µg/kg. Most preferably, each partial dose is about 50 µg/kg.

In some cases the total dose of CD25-ADC is administered over a three week treatment cycle in 3 equal partial doses, with a partial dose administered once a week. For example, with administration of a partial dose on days 1, 8, and 15 of a 3-week treatment cycle.

Tapered and/or Elongated Dosage Regimes

The term "tapered dosage regime" is used herein to describe a dosage regime in which the total dose of CD25-ADC administered in the first treatment cycle (from hereon in termed the "starting dose") is greater than the total dose of CD25-ADC administered in one or more subsequent treatment cycle. A tapered dosage regime contrasts with a constant dosing regime in which the starting dose is the same as the total dose administered in each subsequent treatment cycle (see 'Constant' in Table 1, below).

As used herein, the term 'total dose' is used to mean the total amount of ADC administered during a single treatment cycle.

A subject's tapered dosage regime may consist of 2, 3, 4, 5, 6, 7, 8, 9, 10, 11, 12, 13, 14, 15, 16, 17, 18, 19, 20, 21, 22, 23, 24, 25, 26, 27, 28, 29, 30, or more treatment cycles. In some cases, the dosage regime is ended once the subject attains CR. In some cases, the dosage regime is ended when the subject experiences a DLT. In some cases, the dosage regime is considered as ended if a dose delay exceeding the length of the preceding treatment cycle is required.

In a tapered dosage regime, the starting dose may be reduced no more than once, no more than twice, or no more than three times during the dosage regime. In cases where there are two or more reductions to the starting dose, each reduction may be by the same or a different amount. A total dose may be held constant for one, two, three, or more than three treatment cycles before it is reduced (see Table 1, below, for examples).

TABLE 1

| Dosing Regime | Dose (µg/kg) | | | | | | |
| --- | --- | --- | --- | --- | --- | --- | --- |
| | Cycle 1 | Cycle 2 | Cycle 3 | Cycle 4 | Cycle 5 | Cycle 6 | Cycle 7 |
| Constant | 100 | 100 | 100 | 100 | 100 | 100 | 100 |
| Taper 1 | 100 | 90 | 80 | 70 | 60 | 50 | 40 |
| Taper 2 | 100 | 90 | 70 | 65 | 60 | 40 | 40 |
| Taper 3 | 120 | 120 | 60 | 60 | 60 | 60 | 60 |
| Taper 4 | 150 | 150 | 60 | 60 | 60 | 60 | 60 |
| Taper 5 | 200 | 200 | 60 | 60 | 60 | 60 | 60 |
| Taper 6 | 200 | 60 | 60 | 60 | 60 | 60 | 60 |
| Taper 7 | 150 | 150 | 75 | 75 | 75 | 75 | 75 |
| Taper 8 | 45 | 45 | 45 | 30 | 30 | 30 | 30 |
| Taper 9 | 80 | 80 | 80 | 40 | 40 | 40 | 40 |
| Taper 10 | 60 | 60 | 60 | 40 | 40 | 40 | 40 |

In some cases, the administered dose is only reduced if the subject has attained at least Stable Disease [SD] at the end of the preceding treatment cycle.

In some cases the starting dose is at least about 10, 15, 20, 25, 30, 35, 40, 45, 50, 55, 60, 65, 70, 75, 80, 85, 90, 95, 100, 110, 120, 130, 140, 150, 160, 170, 180, 190, or 200 µg/kg. In some cases the starting dose is at least 120 µg/kg. In some cases the starting dose is at least 150 µg/kg, such as at least 200 µg/kg.

In some cases the starting dose is about 10, 15, 20, 25, 30, 35, 40, 45, 50, 55, 60, 65, 70, 75, 80, 85, 90, 95, 100, 120, 150, 200, 250, 300, 350, 400, 450, 500, 550, or 600 µg/kg. In some cases the starting dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240 µg/kg, 241 to 260 µg/kg, 261 to 280 µg/kg, 281 to 300 µg/kg, 301 to 320 µg/kg, 321 to 340 µg/kg, 341 to 360 µg/kg, 361 to 380 µg/kg, 381 to 400 µg/kg, 401 to 420 µg/kg, 421 to 440 µg/kg, 441 to 460 µg/kg, 461 to 480 µg/kg, 481 to 500 µg/kg, 501 to 520 µg/kg, 521 to 540 µg/kg, 541 to 560 µg/kg, 561 to 580 µg/kg, or 581 to 600 µg/kg.

In some cases the starting dose is about 45, 60, 80, 120, 150, or 200 µg/kg.

In some cases the starting dose is about 40 to 50 µg/kg. In some cases the starting dose is about 45 µg/kg. In some of these cases the treated proliferative disease is Hodgkin's lymphoma.

In some cases the starting dose is about 55 to 65 µg/kg. In some cases the starting dose is about 60 µg/kg. In some of these cases the treated proliferative disease is a T-cell lymphoma.

In some cases the starting dose is about 75 to 85 µg/kg. In some cases the starting dose is about 80 µg/kg. In some of these cases the treated proliferative disease is Acute T-cell lymphoblastic lymphoma (ATLL).

In some cases the starting dose is about 140 to 160 µg/kg. In some cases the starting dose is about 150 µg/kg.

In some cases, each dose reduction reduces the administered dose by at least 50%, 55%, 60%, 65%, 70%, 75%, 80%, 85%, 90% or at least 95%. In some cases, each dose reduction reduces the administered dose by about 50%.

Preferably the starting dose is reduced no more than once during the treatment of a subject. In these cases the total dose following dose reduction is from hereon termed the "reduced dose".

In some cases the dose is reduced following the first treatment cycle. That is, the starting dose is administered in the first treatment cycle and the reduced dose is administered in the second and subsequent treatment cycles. Dosing regime 'Taper 6' in Table 1 is an example of such a dosing regime.

In some cases the dose is reduced following the second treatment cycle. That is, the starting dose is administered in each of the first and second treatment cycles and the reduced dose is administered in each of the third and subsequent treatment cycles. Dosing regime 'Taper 3', 'Taper 4', 'Taper 5', and 'Taper 10' in Table 1 are examples of such a dosing regime.

In some cases the dose is reduced following the third treatment cycle. That is, the starting dose is administered in each of the first, second, and third treatment cycles and the reduced dose is administered in each of the fourth and subsequent treatment cycles. Dosing regime 'Taper 8' and 'Taper 9' are examples of such a dosing regime.

In some cases the reduced dose is about 10, 15, 20, 25, 30, 35, 40, 45, 50, 55, 60, 65, 70, 75, 80, 85, 90, 95, 100, 120, 150, 200, 250, or 300 µg/kg. In some cases the reduced dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240 µg/kg, 241 to 260 µg/kg, 261 to 280 µg/kg, or 281 to 300 µg/kg.

In some cases the reduced dose is 30 µg/kg. In some of these cases the treated proliferative disease is Hodgkin's lymphoma.

In some cases the reduced dose is 60 µg/kg.

In some cases the reduced dose is 70 to 80 µg/kg. In some cases the reduced dose is 75 µg/kg.

In some cases the length of each treatment cycle is 1 week, 2 weeks, 3 weeks, 4 weeks, 5 weeks, 6 weeks, 7 weeks, 8 weeks, or 9 weeks.

In some cases the length of each treatment cycle is 3 weeks. In some cases the length of each treatment cycle is 6 weeks.

The term "elongated dosage regime" is used herein to describe a dosage regime in which the length of the first treatment cycle (from hereon in termed the "starting length") is shorter than the length of one or more subsequent treatment cycle. An elongated dosage regime contrasts with a constant dosing regime in which the starting length is the same the length of each subsequent treatment cycle (see 'Constant' in Table 2, below).

A subject's tapered dosage regime may consist of 2, 3, 4, 5, 6, 7, 8, 9, 10, 11, 12, 13, 14, 15, 16, 17, 18, 19, 20, 21, 22, 23, 24, 25, 26, 27, 28, 29 or 30 treatment cycles. In some cases the dosage regime is ended once the subject attains CR. In some cases the dosage regime is ended when the subject experiences a DLT. In some cases the dosage regime is considered as ended if a dose delay exceeding the length of the preceding treatment cycle is required.

In an elongated dosage regime the treatment cycle length may be increased no more than once, no more than twice, or no more than three times during the dosage regime. In cases where there are two or more increases in length, each increase may be by the same or a different amount. The length of treatment cycle may be held constant for one, two, three, or more than three treatment cycles before it is increased (see Table 2, below, for examples).

TABLE 2

| Dosing Regime | Cycle length (weeks) | | | | | | |
| --- | --- | --- | --- | --- | --- | --- | --- |
| | Cycle 1 | Cycle 2 | Cycle 3 | Cycle 4 | Cycle 5 | Cycle 6 | Cycle 7 |
| Constant | 3 | 3 | 3 | 3 | 3 | 3 | 3 |
| Long 1 | 3 | 4 | 5 | 6 | 6 | 6 | 6 |
| Long 2 | 3 | 3 | 4 | 5 | 5 | 5 | 5 |
| Long 3 | 3 | 3 | 6 | 6 | 6 | 6 | 6 |
| Long 4 | 3 | 6 | 6 | 6 | 6 | 6 | 6 |

In some cases, the treatment cycle length is only increased if the subject has attained at least Stable Disease [SD] at the end of the preceding treatment cycle.

Preferably, the dose is administered as a single dose on Day 1 of the treatment cycle. So, for example, a subject starting the 'constant' dosing regime above may receive a dose on Day 1, Day 22, Day 43, and so on until the regime is halted.

Following this pattern, a subject starting the 'Long 3' dosing regime above may receive a dose on Day 1-(+3 weeks)→Day 22-(+3 weeks)→Day 43-(+6 weeks)→Day 85-(+6 weeks)→Day 127 and so on until the regime is halted. However, preferably the 'Day 1' of the first treatment cycle of increased length is delayed so that the time elapsed between 'Day 1' of the final shorter treatment cycle and 'Day 1' of the first treatment cycle of increased length is equal in length to the increased treatment cycle. Accordingly, in the preferred administration pattern of the 'Long 3' dosing regime a subject receive a dose on Day 1-(+3 weeks)→Day 22-(+3 weeks)→-(+3 week delay)→Day 64-(+6 weeks)→Day 106-(+6 weeks)→Day 148 and so on until the regime is halted.

In some cases the starting length is 1 week, 2 weeks, 3 weeks, 4 weeks, 5 weeks, 6 weeks, 7 weeks, 8 weeks, or 9 weeks.

In some cases the starting length is 3 weeks.

In some cases each length increase increases the treatment cycle length by at least 50%, 55%, 60%, 65%, 70%, 75%, 80%, 85%, 90%, 95% or at least 100%. In some cases each length increase increases the treatment cycle length by 1 week, 2 weeks, 3 weeks, 4 weeks, 5 weeks, or 6 weeks.

Preferably the treatment cycle length is increased no more than once during the treatment of a subject. In these cases the treatment cycle length following length increase is from hereon in termed the "increased length".

In some cases the cycle length is increased following the first treatment cycle. That is, the first treatment cycle is the starting length, and each of the second and subsequent treatment cycles is the increased length. Dosing regime 'Long 4' in Table 2 is an example of such a dosing regime.

In some cases the cycle length is increased following the second treatment cycle. That is, each of the first and second treatment cycles is the starting length, and each of the third and subsequent treatment cycles is the increased length. Dosing regime 'Long 3' in Table 2 is an example of such a dosing regime.

In some cases the increased length is 2 weeks, 3 weeks, 4 weeks, 5 weeks, 6 weeks, 7 weeks, 8 weeks, 9 weeks, 10 weeks, 11 weeks, or 12 weeks.

In some cases the starting length is 3 weeks. In some cases the increased length is 6 weeks. In some cases the starting length is 3 weeks and the increased length is 6 weeks.

A dosing regime may be tapered, elongated, or both tapered and elongated.

Tapered and elongated dosing regimes incorporate both of those elements as described herein.

In some cases, the administered dose is only reduced and/or the treatment cycle length increased if the subject has attained at least Stable Disease [SD] at the end of the preceding treatment cycle.

Preferably, in a tapered and elongated dosage regime the starting dose is reduced no more than once and the treatment cycle length is increased no more than once during the treatment of a subject.

In some cases the dose reduction and the length increase is made following the first treatment cycle. That is, the first treatment cycle has the starting dose and the starting length, and each of the second and subsequent treatment cycles have the reduced dose and increased length.

In some cases the dose reduction and the length increase is made following the second treatment cycle. That is, each of the first and second treatment cycles have the starting dose and the starting length, and each of the third and subsequent treatment cycles have the reduced dose and increased length.

In some cases the dose reduction and the length increase is made following the third treatment cycle. That is, each of the first, second, and third treatment cycles have the starting dose and the starting length, and each of the fourth and subsequent treatment cycles have the reduced dose and increased length.

In some cases the starting dose is at least about 10, 20, 30, 40, 50, 60, 70, 80, 90, 100, 110, 120, 130, 140, 150, 160, 170, 180, 190, or 200 µg/kg. In some cases the starting dose is at least 120 µg/kg. In some cases the starting dose is at least 150 µg/kg, such as at least 200 µg/kg.

In some cases the starting dose is about 10, 15, 20, 25, 30, 35, 40, 45, 50, 55, 60, 65, 70, 75, 80, 85, 90, 95, 100, 120, 150, 200, 250, 300, 350, 400, 450, 500, 550, or 600 µg/kg. In some cases the starting dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240 µg/kg, 241 to 260 µg/kg, 261 to 280 µg/kg, 281 to 300 µg/kg, 301 to 320 µg/kg, 321 to 340 µg/kg, 341 to 360 µg/kg, 361 to 380 µg/kg, 381 to 400 µg/kg, 401 to 420 µg/kg, 421 to 440 µg/kg, 441 to 460 µg/kg, 461 to 480 µg/kg, 481 to 500 µg/kg, 501 to 520 µg/kg, 521 to 540 µg/kg, 541 to 560 µg/kg, 561 to 580 µg/kg, or 581 to 600 µg/kg.

In some cases the reduced dose is about 10, 15, 20, 25, 30, 35, 40, 45, 50, 55, 60, 65, 70, 75, 80, 85, 90, 95, 100, 120, 150, 200, 250, or 300 µg/kg. In some cases the reduced dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240 µg/kg, 241 to 260 µg/kg, 261 to 280 µg/kg, or 281 to 300 µg/kg.

In some cases the starting length is 1 week, 2 weeks, 3 weeks, 4 weeks, 5 weeks, 6 weeks, 7 weeks, 8 weeks, or 9 weeks.

In some cases the increased length is 2 weeks, 3 weeks, 4 weeks, 5 weeks, 6 weeks, 7 weeks, 8 weeks, 9 weeks, 10 weeks, 11 weeks, or 12 weeks.

In some cases the starting dose is about 45, 60, 80, 120, 150, or 200 µg/kg. In some cases the starting dose is about 45 µg/kg. In some of these cases the treated proliferative disease is Hodgkin's lymphoma. In some cases the starting dose is about 55 to 65 µg/kg. In some cases the starting dose is about 60 µg/kg. In some of these cases the treated proliferative disease is a T-cell lymphoma. In some cases the starting dose is about 75 to 85 µg/kg. In some cases the starting dose is about 80 µg/kg. In some of these cases the treated proliferative disease is Acute T-cell lymphoblastic lymphoma (ATLL). In some cases the starting dose is about 140 to 160 µg/kg. In some cases the starting dose is about 150 µg/kg.

In some cases the reduced dose is 30 µg/kg. In some of these cases the treated proliferative disease is Hodgkin's lymphoma. In some cases the reduced dose is 60 µg/kg. In some cases the reduced dose is 70 to 80 µg/kg. In some cases the reduced dose is 75 µg/kg. In some cases the starting length is 3 weeks and the increased length is 6 weeks. In some cases the starting dose and starting length are respectively about 120 µg/kg and three weeks and the reduced dose and increased length are respectively about 60 µg/kg and six weeks. In some cases the starting dose and starting length are respectively about 150 µg/kg and three weeks and the reduced dose and increased length are respectively about 60 µg/kg and six weeks.

In some particularly preferred cases the starting dose and starting length are respectively about 140 to 160 µg/kg and three weeks and the reduced dose and increased length are respectively about 70 to 80 µg/kg and three weeks (i.e. the regime is tapered but NOT elongated).

In some particularly preferred cases the starting dose and starting length are respectively about 150 µg/kg and three weeks and the reduced dose and increased length are respectively about 75 µg/kg and three weeks (i.e. the regime is tapered but NOT elongated).

In some particularly preferred cases, the dosing regime of the present disclosure is as shown in the table below, with {+21} indicating that the reduced 75 µg/kg dose may be repeated at three weekly intervals for as many treatment cycles as deemed appropriate by the medical professional administering the ADC.

| Regimen Day | 1 | 22 | 43 | 65 | 86 | [+21] |
|---|---|---|---|---|---|---|
| ADC dose | 150 ug/kg | 150 ug/kg | 75 ug/kg | 75 ug/kg | 75 ug/kg | [75 ug/kg] |

In some particularly preferred cases the starting dose and starting length are respectively about 40 to 50 µg/kg and three weeks and the reduced dose and increased length are respectively about 25 to 35 µg/kg and three weeks (i.e. the regime is tapered but NOT elongated). In some of these cases the disorder treated is Hodgkin's lymphoma.

In some particularly preferred cases the starting dose and starting length are respectively about 45 µg/kg and three weeks and the reduced dose and increased length are respectively about 30 µg/kg and three weeks (i.e. the regime is tapered but NOT elongated).

In some particularly preferred cases, the dosing regime of the present disclosure is as shown in the table below, with {+21} indicating that the reduced 30 µg/kg dose may be repeated at three weekly intervals for as many treatment cycles as deemed appropriate by the medical professional administering the ADC.

| Regimen Day | 1 | 22 | 43 | 65 | 86 | [+21] |
|---|---|---|---|---|---|---|
| ADC dose | 45 ug/kg | 45 ug/kg | 45 ug/kg | 30 ug/kg | 30 ug/kg | [30 ug/kg] |

Treated Disorders

The methods of therapy described herein include those with utility for anticancer activity. In particular, in certain aspects the therapies include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the disclosure selectively deliver an effective dose of a cytotoxic agent to tumor tissue whereby greater selectivity, i.e. less off-target toxicity and therefore a better therapeutic index, may be achieved.

The disorders treated may be proliferative disorders. The disorders treated may be non-proliferative disorders, such as disorders in which CD25+ play a role in the pathology.

Thus, in one aspect, the present disclosure provides a method of therapy comprising administering an ADC which binds CD25 for use in therapy, wherein the method comprises selecting a subject based on expression of CD25.

In one aspect, the present disclosure provides a packaged ADC for use in therapy, wherein the packaged ADC is supplied with a label that specifies that the therapy is suitable for use with a subject determined to be suitable for such use. The label may specify that the therapy is suitable for use in a subject has expression of CD25, that is, is CD25+. The label may specify that the ADC is administered in a fractionated dosage regime as described herein. The label may specify that the subject has a particular type of cancer, such as a leukaemia like CD25+ Acute Myeloid Leukemia or CD25+ Acute Lymphoblastic Leukemia. Examples of leukaemia suitable for treatment by a fractionated dosage regime include Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL).B-cell Lineage Acute Lymphoblastic Leukemias (B-ALL).

The label may specify that the ADC is administered in a tapered and/or elongated dosage regime as described herein. The label may specify that the subject has a particular type of cancer, such as lymphoma like Hodgkin lymphoma, or Non Hodgkin Lymphoma (NHL), optionally wherein the lymphoma is Relapsed or Refractory. NHL includes lymphomas from both:

(1) B-cell lineages, such as diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL); and (2) T-cell lineages, such as Extranodal T cell lymphoma, Cutaneous T-cell lymphomas (Sézary syndrome and Mycosis fungoides), Anaplastic large cell lymphoma, T-cell lymphoblastic lymphoma, including acute T-cell lymphoblastic lymphoma (ATLL), and Angioimmunoblastic T-cell lymphoma Other proliferative diseases treatable with CD25-ADCs include T-cell lineage leukaemias, such as Large granular lymphocytic leukaemia, adult T-cell leukaemia, and T-cell prolymphocytic leukaemia. In some embodiments, these diseases are treated with a CD25-ADC in a Q3W treatment regime that is neither tapered or elongated. The dosage of CD25-ADC (preferably ADCx25) administered per treatment cycle may be 50 to 70 µg/kg, such as 55 to 65 µg/kg, for example about 60 µg/kg.

The proliferative disease may be characterised by the presence of a neoplasm comprising both CD25+ve and CD25−ve cells. Both CD25+ve and CD25−ve cells may be neoplastic cells. When administered to a subject with such disease, the ADC may cause cell death of both the CD25+ve and CD25−ve cells in the neoplasm.

The proliferative disease treated by the methods disclosed herein may be CD25+. However as explained herein, in the practice of the disclosure, in at least some of the cells in the target location (typically a neoplasm) the antigen may be absent, or present on the cell surface at an insignificant level. For example in the target neoplasm only e.g. less than 80, 70, 60, 50, 30, 20%, 10% or 5% of the cells may be CD25 positive. In some cases where the disease is a leukemia, such as AML, CD25+ is defined as determination of CD25 expression by ≥5% of leukemic myeloblast cells within bone marrow (aspirate or biopsy), as assessed at an approved clinical laboratory.

In some cases the CD25+ve cell is a tumour infiltrating lymphocyte. In some cases the neoplasm or neoplastic cells are, or are present in, a hematological cancer. In some cases the neoplasm or neoplastic cells are, or are present in, a solid tumor. "Solid tumor" herein will be understood to include solid hematological cancers such as lymphomas (Hodgkin's lymphoma or non-Hodgkin's lymphoma) which are discussed in more detail below.

Other solid tumors may be neoplasms, including non-hematological cancers, infiltrated with CD-25 positive T-cells.

In some cases the neoplasm or neoplastic cells are malignant. In some cases the neoplasm or neoplastic cells are metastatic.

The therapies described herein may be used to treat a proliferative disease. The term "proliferative disease" pertains to an unwanted or uncontrolled cellular proliferation of excessive or abnormal cells which is undesired, such as, neoplastic or hyperplastic growth, whether in vitro or in vivo.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

It is contemplated that the therapies of the present disclosure may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune disorders and graft-versus-host disease (GVHD).

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, soft-tissue-sarcoma, osteosarcoma as well as head and neck cancer.

Autoimmune diseases for which the combined therapies may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, graft-versus-host disease (GVHD), and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

In some aspects, the subject has a proliferative disorder selected from (classical) Hodgkin lymphomas, with mixed cellularity type (Hodgkin-/Reed-Sternbert-Cells: CD25+/−), or non-Hodgkin lymphoma. NHL includes lymphomas from both:

(1) B-cell lineages, such as diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL); and
(2) T-cell lineages, such as Extranodal T cell lymphoma, Cutaneous T-cell lymphomas (Sézary syndrome and Mycosis fungoides), Anaplastic large cell lymphoma, T-cell lymphoblastic lymphoma, including acute T-cell lymphoblastic lymphoma (ATLL), and Angioimmunoblastic T-cell lymphoma Classical Hodgkins lymphoma includes the subtypes nodular sclerosing, lymphocyte predominant, lymphocyte depleted and mixed cellularity. The Hodgkins lymphoma subtype may not be defined. In certain aspects, the subjects tested according to the methods here have Hodgkins lymphoma of the nodular sclerosing and mixed cellularity subtypes.

In certain aspects, the subject has diffuse large B cell lymphoma or peripheral T cell lymphoma, including the anaplastic large cell lymphoma and angioimmunoblastic T cell lymphoma subtypes.

The disease may be resistant, relapsed or refractory. For example the disease may be relapsed or refractory AML. The term "relapsed or refractory AML" as used herein refers to the diagnosis and classification of AML & rAML as per World Health Organization (WHO) classification of AML (Jaffe E S, Harris N L, Stein H, Vardiman J W (eds) Pathology and genetics of tumors of haematopoietic and lymphoid tissues. Lyon: IARC Press; 2001. p. 75-107; Vardiman J W, Harris N L, Brunning R D. The World Health Organization (WHO) classification of the myeloid neoplasms. Blood. 2002; 100:2292-302).

Preferably, the fractionated dosage regimes described here are employed when the proliferative disease is leukaemia, such as Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL). In some cases the proliferative disease is Relapsed or Refractory B-cell Lineage Acute Lymphoblastic Leukemias (B-ALL). In some cases the proliferative disease is Relapsed or Refractory CD25+ Acute Myeloid Leukemia.

Preferably, the tapered and/or elongated dosage regimes described here are employed when the proliferative disease is lymphoma. For example, the proliferative disease may be a Hodgkin lymphoma, or non-Hodgkin's Lymphoma. NHL includes lymphomas from both:

(1) B-cell lineages, such as diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL); and
(2) T-cell lineages, such as Extranodal T cell lymphoma, Cutaneous T-cell lymphomas (Sézary syndrome and Mycosis fungoides), Anaplastic large cell lymphoma, T-cell lymphoblastic lymphoma, including acute T-cell lymphoblastic lymphoma (ATLL), and Angioimmunoblastic T-cell lymphoma Reduced Toxicity and of Improved Efficacy Fractionated Dosage Regimes The present disclosure provides a method of reducing the toxicity and/or side effects associated with administration of an CD25-ADC to a subject, the method comprising administering the CD25-ADC in a fractionated dosage regime as defined herein.

In some cases the reduction in toxicity is measured relative to a single-dose dosage regime having the same total dose administered and length of treatment cycle. In such a single dose regime, the total dose of CD25-ADC is administered as a single dose at the start of the treatment cycle.

In some cases the level of toxicity is measured as the incidence of Treatment Emergent Adverse Events (TEAE) occurring after one treatment cycle at a given total dose of CD25-ADC. A treatment-emergent AE (TEAE) is defined as any event not present before exposure to the CD25-ADC or any event already present that worsens in either intensity or frequency after exposure to the CD25-ADC. The incidence of AE with the fractionated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of AE in the corresponding single dose regime. Adverse events will be graded according to CTCAE Version 4.0 (v4.03, published Jun. 14, 2010; NIH Publication No. 09-5410).

For example, if a single treatment cycle of a single-dose regime in 100 subjects leads to 10 AEs and a single treatment cycle the corresponding fractionated regime leads to 5 AEs, the incidence of AEs with the fractionated regime is 50% of the incidence of AE in the corresponding single dose regime.

In some cases the level of toxicity is measured as the incidence of Serious Adverse Events (SAE) occurring after one treatment cycle at a given total dose of CD25-ADC. A serious adverse event (SAE) is defined as any event that results in death, is immediately life-threatening, requires inpatient hospitalization or prolongation of existing hospitalization, results in persistent or significant disability/incapacity, or is a congenital anomaly/birth defect. Hospitalization for elective procedures or for protocol compliance is not considered an SAE. Important medical events that may not result in death, be life-threatening, or require hospitalization may be considered SAEs when, based upon appropriate medical judgment, they may jeopardize the patient or may require medical or surgical intervention to prevent 1 of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse. The incidence of SAE with the fractionated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of SAE in the corresponding single dose regime. Adverse events will be graded according to CTCAE Version 4.0 (v4.03, published Jun. 14, 2010; NIH Publication No. 09-5410).

In some cases the level of toxicity is measured as the incidence of Dose Limiting Toxicity (DLT) occurring after one treatment cycle at a given total dose of CD25-ADC. The incidence of DLT with the fractionated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of DLT in the corresponding single dose regime.

For example, if a single treatment cycle of a single-dose regime in 100 subjects leads to 10 DLTs and a single treatment cycle of the corresponding fractionated regime leads to 5 DLTs, the incidence of DLTs with the fractionated regime is 50% of the incidence of DLT in the corresponding single dose regime.

A DLT as used herein is defined as any of the following events, except those that are clearly due to underlying disease or extraneous causes:
A hematologic DLT is defined as:
Grade 3 or higher event of neutropenia and/or thrombocytopenia or a Grade 4 anaemia, with a hypocellular bone marrow lasting for 6 weeks or more after the start of a cycle, in the absence of residual leukemia (i.e., with <5% blasts). In case of a normocellular bone marrow with <5% blasts, 8 weeks with ≥Grade 3 pancytopenia will be considered a DLT.
A non-hematologic DLT is defined as:
Grade 4 tumor lysis syndrome (Grade 3 TLS will not constitute DLT unless it leads to irreversible end-organ damage).
Grade 3 or higher AEs (including nausea, vomiting, diarrhoea, and electrolyte imbalances lasting more than 48 hours despite optimal therapy; excluding all grades of alopecia).
Grade 3 or higher hypersensitivity reaction (regardless of premedication).
Grade 3 or higher skin ulceration.

The above adverse events will be graded according to CTCAE Version 4.0 (v4.03, published Jun. 14, 2010; NIH Publication No. 09-5410).

The present disclosure also provides a method of increasing the treatment efficacy associated with administration of a CD25-ADC to a subject, the method comprising administering the CD25-ADC in a fractionated dosage regime as defined herein.

In some cases the increase in efficacy is measured relative to a single-dose dosage regime having the same total dose administered and length of treatment cycle. In such a single dose regime, the total dose of ADC is administered as a single dose at the start of the treatment cycle.

In some cases the level of efficacy is measured as the proportion of subjects achieving at least a partial response [PR] after one treatment cycle at a given total dose of ADC (i.e the proportion of subjects achieving either a partial response [PR], a complete response with incomplete blood count recovery [CRi], or a complete response [CR]. The proportion of subjects achieving at least PR may be at least 110%, such as at least 120%, at least 130%, at least 140%, at least 150%, at least 160%, at least 170%, at least 180%, at least 190%, or at least 200%, of the proportion of subjects achieving at least a partial response [PR] in the corresponding single dose regime.

For example, if a single-dose regime in 100 subjects leads to at least PR in 50 subjects and the corresponding fractionated regime leads to at least PR in 80 subjects, the proportion of subjects achieving at least PR with the fractionated regime is 160% of the proportion of subjects achieving at least a partial response [PR] in the corresponding single dose regime.

Assessment of response to treatment with ADC may be based on bone marrow samples (aspirate or biopsy if aspirate unattainable) taken toward the end of each treatment cycle. For example, on day 19±3 days in a 21-day treatment cycle. The subject's response to ADC may be categorised as CR, CRi, PR, PD or NR according to the following criteria:
Complete response (CR) is defined as achieving each of the following:
Bone marrow differential showing ≤55% blast cells and absence of blast cells with Auer rods.
Absolute neutrophil count ≥1.0×109/L and platelet count ≥100×109/L.
Absence of extramedullary disease.
Patient is independent of red blood cell (RBC) transfusions.
Complete response with incomplete blood count recovery (CRi) is defined as achieving all CR criteria except that values for ANC may be <1.0×109/L and/or values for platelets may be <100×109/L.
Partial response (PR) is defined as achieving each of the following:
Absolute neutrophil count ≥1.0×109/L and platelet count ≥100×109/L.
Bone marrow differential showing a ≥50% decrease from baseline in the percentage of bone marrow blast cells to a level ≥5% and ≤25%, or bone marrow differential showing <5% blast cells and presence of Auer rods.

No response (NR) is defined as not achieving CR, CRi, or PR.

Progressive disease (PD) is defined as:
  For patients with CR or CRi, the first date of reappearance of blast cells in bone marrow and/or peripheral blood to a level ≥5%, or development of extramedullary disease.
  For patients with PR, the first date of an increase in blast cells in bone marrow and/or peripheral blood such that the patient does not continue to meet the criteria for PR.

Tapered/Elongated Dosage Regimes

The present disclosure provides a method of reducing the toxicity and/or side effects associated with administration of a CD25-ADC to a subject, the method comprising administering the CD25-ADC in a tapered and/or elongated dosage regime as defined herein.

In some cases the reduction in toxicity is measured relative to a dosage regime having constant dosage level and cycle length. The dosage level and cycle length of the constant comparator may be the same as the starting dose and starting length of the tapered and/or elongated regime.

In some cases the level of toxicity is measured as the incidence of Treatment Emergent Adverse Events (TEAE) occurring after one treatment cycle at a given total dose of CD25-ADC. A treatment-emergent AE (TEAE) is defined as any event not present before exposure to the CD25-ADC or any event already present that worsens in either intensity or frequency after exposure to the CD25-ADC. The incidence of AE with the tapered and/or elongated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of AE in the corresponding constant dose level and cycle length regime. Adverse events will be graded according to CTCAE Version 4.0 (v4.03, published Jun. 14, 2010; NIH Publication No. 09-5410).

For example, if a single treatment cycle of a single-dose regime in 100 subjects leads to 10 AEs and a single treatment cycle the corresponding tapered and/or elongated regime leads to 5 AEs, the incidence of AEs with the tapered and/or elongated regime is 50% of the incidence of AE in the corresponding constant dose level and cycle length regime.

In some cases the level of toxicity is measured as the incidence of Serious Adverse Events (SAE) occurring after one treatment cycle at a given total dose of CD25-ADC. A serious adverse event (SAE) is defined as any event that results in death, is immediately life-threatening, requires inpatient hospitalization or prolongation of existing hospitalization, results in persistent or significant disability/incapacity, or is a congenital anomaly/birth defect. Hospitalization for elective procedures or for protocol compliance is not considered an SAE. Important medical events that may not result in death, be life-threatening, or require hospitalization may be considered SAEs when, based upon appropriate medical judgment, they may jeopardize the patient or may require medical or surgical intervention to prevent 1 of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse. The incidence of SAE with the tapered and/or elongated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of SAE in the corresponding constant dose level and cycle length regime. Adverse events will be graded according to CTCAE Version 4.0 (v4.03, published Jun. 14, 2010; NIH Publication No. 09-5410).

In some cases the level of toxicity is measured as the incidence of Dose Limiting Toxicity (DLT) occurring after one treatment cycle at a given total dose of CD25-ADC. The incidence of DLT with the tapered and/or elongated dosage regime may be no more that 95%, such as no more than 90%, no more than 80%, no more than 70%, no more than 60%, no more than 50%, no more than 40%, no more than 30%, no more than 20%, no more than 10%, or no more than 5% of the incidence of DLT in the corresponding constant dose level and cycle length regime.

For example, if a single treatment cycle of a single-dose regime in 100 subjects leads to 10 DLTs and a single treatment cycle of the corresponding tapered and/or elongated regime leads to 5 DLTs, the incidence of DLTs with the tapered and/or elongated regime is 50% of the incidence of DLT in the corresponding constant dose level and cycle length regime.

A DLT as used herein is defined as any of the following events, except those that are clearly due to underlying disease or extraneous causes:
  A hematologic DLT is defined as:
    Grade 3 or 4 febrile neutropenia or neutropenic infection.
    Grade 4 neutropenia lasting >7 days.
    Grade 4 thrombocytopenia.
    Grade 3 thrombocytopenia with clinically significant bleeding, or Grade 3 thrombocytopenia requiring a platelet transfusion
    Grade 4 anemia.
  A non-hematologic DLT is defined as:
    Grade 4 tumor lysis syndrome (Grade 3 TLS will not constitute DLT unless it leads to irreversible end-organ damage).
    Grade 3 or higher AE (including nausea, vomiting, diarrhea, and electrolyte imbalances lasting more than 48 hours despite optimal therapy; excluding all grade of alopecia).
    Grade 3 or higher hypersensitivity reaction (regardless of premedication).
    Grade 2 or higher skin ulceration.

The above adverse events will be graded according to CTCAE Version 4.0 (v4.03, published Jun. 14, 2010; NIH Publication No. 09-5410).

The present disclosure also provides a method of increasing the treatment efficacy associated with administration of a CD25-ADC to a subject, the method comprising administering the CD25-ADC in a tapered and/or elongated dosage regime as defined herein.

In some cases the increase in efficacy is measured relative to a dosage regime having constant dosage level and cycle length. The dosage level and cycle length of the constant comparator may be the same as the starting dose and starting length of the tapered and/or elongated regime.

In some cases the level of efficacy is measured as the proportion of subjects achieving at least stable disease [SD] after one treatment cycle at a given total dose of ADC (i.e the proportion of subjects achieving either stable disease [SD], a partial response [PR], or a complete response [CR]. The proportion of subjects achieving at least SD may be at least 110%, such as at least 120%, at least 130%, at least 140%, at least 150%, at least 160%, at least 170%, at least 180%, at least 190%, or at least 200%, of the proportion of subjects achieving at least stable disease [SD] in the corresponding constant dose level and cycle length regime.

For example, if a single-dose regime in 100 subjects leads to at least SD in 50 subjects and the corresponding tapered and/or elongated regime leads to at least SD in 80 subjects, the proportion of subjects achieving at least SD with the tapered and/or elongated regime is 160% of the proportion of subjects achieving at least a partial response [SD] in the corresponding constant dose level and cycle length regime.

Assessment of response to treatment with ADC may be based on bone marrow samples (aspirate or biopsy if aspirate unattainable) taken toward the end of each treatment cycle. For example, on day 19±3 days in a 21-day treatment cycle. The subject's response to ADC may be categorised as CR, PR, SD, or PD according to the 2014 Lugano Classification Criteria (using the New "Cheson" Criteria), in which:

Complete response (CR) is defined as achieving each of the following:
Nodal Disease <1.5 cm in LDi
Extranodal Disease: Absent
Spleen: regress to normal
No new lesions
Bone marrow: Normal by morphology; if indeterminate, IHC negative Partial response (PR) is defined as achieving each of the following:
Nodal Disease >=50% decrease from baseline in SPD of all target lesions
No increase in non-target
Spleen: >50% decrease from baseline in enlarged portion of spleen (value >13 cm)
No new lesions Stable Disease (SD) is defined as achieving each of the following:
Nodal Disease <50% decrease from baseline in SPD of all target lesions
No criteria for nodal PD are met
No progression in non-target
No progression in spleen enlargment
No new lesions Nodal PD criteria:
An individual node/lesion must be abnormal with:
LDi>1.5 cm AND
Increase by >=50% from PPD nadir AND
An increase in LDi or SDi from nadir
≥0.5 cm for lesions ≤2 cm
≥1.0 cm for lesions >2 cm In some embodiments, PET response is used as an assessment criteria for treatment efficacy. In these embodiments, for a subject to be classed as attaining complete response [CR] they would require a score of 1 to 3 in the modified 5-pont scale described in van Heertum, R L et al., Drug Des Devel Ther. 2017; 11: 1719-1728.

Patient Selection

In certain cases, the subjects are selected as suitable for treatment with either, (a) the fractionated dosage regime, or (b) the tapered and/or elongated dosage regime, before the treatment is administered.

Preferably, subjects are selected for treatment with the tapered and/or elongated dosage regimes described if they have, are suspected of having, or have been diagnosed with lymphoma. For example, the lymphoma may be a Hodgkin lymphoma, or non-Hodgkin's Lymphoma. NHL includes lymphomas from both:

(1) B-cell lineages, such as diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL); and
(2) T-cell lineages, such as Extranodal T cell lymphoma, Cutaneous T-cell lymphomas (Sézary syndrome and Mycosis fungoides), Anaplastic large cell lymphoma, T-cell lymphoblastic lymphoma, including acute T-cell lymphoblastic lymphoma (ATLL), and Angioimmunoblastic T-cell lymphoma Preferably, subjects are selected for treatment with the fractionated dosage regimes described if they have, are suspected of having, or have been diagnosed with leukaemia, For example, the leukaemia may be Hairy cell leukaemia (HCL), Hairy cell leukaemia variant (HCL-v), and Acute Lymphoblastic Leukaemia (ALL) such as Philadelphia chromosome-positive ALL (Ph+ALL) or Philadelphia chromosome-negative ALL (Ph-ALL).

As used herein, subjects who are considered suitable for treatment are those subjects who are expected to benefit from, or respond to, the treatment. Subjects may have, or be suspected of having, or be at risk of having cancer. Subjects may have received a diagnosis of cancer. In particular, subjects may have, or be suspected of having, or be at risk of having, lymphoma. In some cases, subjects may have, or be suspected of having, or be at risk of having, a solid cancer that has tumour associated non-tumor cells that express a CD25, such as infiltrating T-cells that express CD25.

In some cases, subjects are selected on the basis of the amount or pattern of expression of CD25. In some cases, the selection is based on expression of CD25 at the cell surface.

In some cases, expression of CD25 in a particular tissue of interest is determined. For example, in a sample of lymphoid tissue or tumor tissue. In some cases, systemic expression of CD25 is determined. For example, in a sample of circulating fluid such as blood, plasma, serum or lymph.

In a preferred embodiment, the level of soluble CD25 (sCD25) is measured in a sample of circulating fluid such as blood, plasma, serum or lymph. The level of soluble CD25 measures may be used to determine: (1) suitability of subject for treatment with CD25-ADC; (2) optimal dose of CD25-ADC to be administered to the subject; and/or (3) efficacy of treatment following administration of CD25-ADC. The level of sCD25 in the sample may be quantified by ELISA, such as the CD25 Quantikine® ELISA, Catalog numbers DR2A00, SR2A00, and PDR2A00.

In some cases, the subject is selected as suitable for treatment due to the presence of CD25 expression in a sample. In those cases, subjects without CD25 expression may be considered not suitable for treatment.

In other cases, the level of CD25 expression is used to select a subject as suitable for treatment. Where the level of expression of CD25 is above a threshold level, the subject is determined to be suitable for treatment.

In some cases, the presence of CD25 in cells in the sample indicates that the subject is suitable for treatment with a combination comprising an ADC. In other cases, the amount of CD25 expression must be above a threshold level to indicate that the subject is suitable for treatment. In some cases, the observation that CD25 localisation is altered in the sample as compared to a control indicates that the subject is suitable for treatment.

In some cases, a subject is indicated as suitable for treatment if cells obtained from lymph node or extra nodal sites react with antibodies against CD25 as determined by IHC.

In some cases, a patient is determined to be suitable for treatment if at least 5%, 10%, 15%, 20%, 25%, 30%, 35%, 40%, 45%, 50%, 55%, 60%, 65%, 70%, 75%, 80%, 85%, 90% or more of all cells in the sample express CD25. In some cases disclosed herein, a patient is determined to be suitable for treatment if at least at least 5% of the cells in the sample express CD25.

In some cases, a patient is determined to be suitable for treatment if they have had a DLT in a previous single-dose treatment cycle with the ADC.

In some cases, a patient is determined to be suitable for treatment if they have exhibited any sign of ADC-induced toxicity in a previous single-dose treatment cycle with the ADC.

In some cases, a patient is determined to be suitable for treatment if they have increased sensitivity to ADC-induced toxicity.

In some cases, a patient is determined to be suitable for treatment if their disease is relapsed or refractory.

In some cases, a subject undergoes a neurological examination prior to treatment with the ADC. Preferably the neurological examination includes tests of strength, sensation, and deep-tendon reflexes.

In some cases, a subject is determined to be not suitable for treatment with the ADC if they have, or have recently had, a neurologic disorder. Examples of such disorders include poliomyelitis and multiple sclerosis Generally, neurological disorders that are explained by the subject's previous medical history and known not to be related to, or a risk factor for, to treatment with ADC do not render a subject unsuitable for treatment with the ADC. An example of such a disorder is a left-sided weakness known to be a result of a previous cerebral vascular accident, such as a stroke.

The neurologic disorder, as discussed herein, may be polyradiculopathy (including acute inflammatory demyelinating polyradiculoneuropathy (AIDP)), Guillain-Barré syndrome (GBS), myasthenia gravis, or neurologic disorder that is linked to or is an early indicator of polyradiculitis, GBS, or myasthenia gravis (e.g. ascending (bilateral) sensory loss and/or motor weakness).

In some cases, a subject undergoes a neurological examination after administration of the ADC. In some cases the results of the neurological examination of a subject after administration of the ADC are compared to the results from before administration of the ADC in order to assess any change in the tested neurological parameters. In some cases, treatment with the ADC is reduced, suspended, or permanently discontinued if the subject experiences a neurologic toxicity.

The neurologic toxicity, as discussed herein, may be polyradiculopathy (including acute inflammatory demyelinating polyradiculoneuropathy (AIDP)), Guillain-Barré syndrome (GBS), myasthenia gravis, or neurologic disorder that is linked to or is an early indicator of polyradiculitis, GBS, or myasthenia gravis (e.g. ascending (bilateral) sensory loss and/or motor weakness).

In some cases, a subject undergoes a neurological examination after each administration of the ADC. In some cases the results of the neurological examination of a subject after each administration of the ADC are compared to the results from before the most recent administration of the ADC in order to assess any change in the tested neurological parameters. In some cases the results of the neurological examination of a subject after each administration of the ADC are compared to the results from before the first administration of the ADC in order to assess any change in the tested neurological parameters.

In some cases, a subject undergoes a neurological examination if they experience a neurologic toxicity following administration of the ADC.

In some cases, treatment with the ADC is reduced, suspended, or permanently discontinued if the subject has a neurological disorder or experiences a neurologic toxicity. For example, if a subject experiences ≥grade 1 neurologic toxicity, such as a grade 1 neurologic toxicity that is linked to or is an early indicator of polyradiculitis (e.g. ascending (bilateral) sensory loss and/or motor weakness) treatment with the ADC may be reduced or suspended. In some case, if the subject experiences a grade ≥2 neurologic toxicity (e.g. grade 2 polyradiculitis or GBS), treatment with the ADC may be permanently discontinued.

Adverse events will be graded according to CTCAE Version 4.0 (v4.03, published Jun. 14, 2010; NIH Publication No. 09-5410).

In some cases, treatment with the ADC is reduced by reducing the dose of ADC that is administered to the subject in each subsequent treatment cycle. In some cases, treatment with the ADC is reduced by increasing the length of each subsequent treatment cycle for example, from a 3 week cycle to a 6 week cycle). In some cases, treatment with the ADC is reduced by reducing the dose of ADC that is administered to the subject in each subsequent treatments cycle and increasing the length of each subsequent treatment.

In some cases, treatment with the ADC is suspended by stopping treatment with the ADC until the toxicity is resolved. In some cases, treatment with the ADC is resumed after resolution of the toxicity to baseline. The subject may be monitored weekly until the neurologic toxicity is resolved. In some cases the treatment is suspended for up to 3 weeks (21 days).

For example, in some cases a subject undergoes a neurological examination if they experience ≥grade 1 neurologic toxicity, such as a grade 1 neurologic toxicity that is linked to or is an early indicator of polyradiculitis (e.g. ascending (bilateral) sensory loss and/or motor weakness). In some cases, if a subject experiences a ≥grade 1 neurologic toxicity (e.g. grade 1 polyradiculitis or GBS), treatment with the ADC is resumed after resolution of the toxicity to baseline. The subject may be monitored weekly until the neurologic toxicity is resolved.

In some cases, if a subject experiences a ≥grade 2 neurologic toxicity (e.g. grade 2 polyradiculitis or GBS), treatment with the ADC is permanently discontinued.

In some cases, a subject is determined to be not suitable for treatment with the ADC if they have, have recently had, or historically had, an infection caused by a pathogen that may be associated with neurologic and/or immune-related disease. Examples of such pathogens include HSV1, HSV2, VZV, EBV, CMV, measles, Influenza A, Zika virus, Chikungunya virus, *Mycoplasma pneumonia, Campylobacter jejuni*, or enterovirus D68.

In some cases, treatment with the ADC is reduced, suspended, or permanently discontinued if the subject experiences has, or acquires, an infection caused by a pathogen that may be associated with neurologic and/or immune-related disease. Examples of such pathogens include HSV1, HSV2, VZV, EBV, CMV, measles, Influenza A, Zika virus, Chikungunya virus, *Mycoplasma pneumonia, Campylobacter jejuni*, or enterovirus D68. In some cases, treatment with the ADC is suspended until at least 4 weeks after symptoms of the infection are resolved.

Examples of immune-relatyed diseases include rheumatoid arthritis, systemic progressive sclerosis [scleroderma], systemic lupus erythematosus, Sjögren's syndrome, autoimmune vasculitis [e.g., Wegener's granulomatosis].

In some cases, treatment with the ADC is reduced, suspended, or permanently discontinued if the subject experiences any ≥grade 1 autoimmune toxicities (e.g. endocrinopathies,).

Samples

The sample may comprise or may be derived from: a quantity of blood; a quantity of serum derived from the subject's blood which may comprise the fluid portion of the blood obtained after removal of the fibrin clot and blood cells; a quantity of pancreatic juice; a tissue sample or biopsy; or cells isolated from said subject.

A sample may be taken from any tissue or bodily fluid. In certain cases, the sample may include or may be derived from a tissue sample, biopsy, resection or isolated cells from said subject.

In certain cases, the sample is a tissue sample. The sample may be a sample of tumor tissue, such as cancerous tumor tissue. The sample may have been obtained by a tumor biopsy. In some cases, the sample is a lymphoid tissue sample, such as a lymphoid lesion sample or lymph node biopsy. In some cases, the sample is a skin biopsy.

In some cases the sample is taken from a bodily fluid, more preferably one that circulates through the body. Accordingly, the sample may be a blood sample or lymph sample. In some cases, the sample is cerebrospinal fluid, a urine sample or a saliva sample.

In some cases, the sample is a blood sample, a bone-marrow aspirate, or blood-derived sample. The blood derived sample may be a selected fraction of a subject's blood, e.g. a selected cell-containing fraction or a plasma or serum fraction.

A selected cell-containing fraction may contain cell types of interest which may include white blood cells (WBC), particularly peripheral blood mononuclear cells (PBC) and/or granulocytes, and/or red blood cells (RBC). Accordingly, methods according to the present disclosure may involve detection of a CD25 polypeptide or nucleic acid in the blood, in white blood cells, peripheral blood mononuclear cells, granulocytes and/or red blood cells.

The sample may be fresh or archival. For example, archival tissue may be from the first diagnosis of a subject, or a biopsy at a relapse. In certain cases, the sample is a fresh biopsy.

Subject Status

The subject may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a foetus. In one preferred embodiment, the subject is a human. The terms "subject", "patient" and "individual" are used interchangeably herein.

In some cases disclosed herein, a subject has, or is suspected as having, or has been identified as being at risk of, cancer. In some cases disclosed herein, the subject has already received a diagnosis of cancer.

The subject may have, be suspected of having, been identified as being at risk of, or received a diagnosis of lymphoma, like (classical) Hodgkins lymphoma (including nodular sclerosing, lymphocyte predominant, lymphocyte, or mixed cellularity type, or where the type is unspecified), or NHL. NHL includes lymphomas from both: (1) B-cell lineages, such as diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL); and (2) T-cell lineages, such as Extranodal T cell lymphoma, Cutaneous T-cell lymphomas (Sézary syndrome and Mycosis fungoides), Anaplastic large cell lymphoma, T-cell lymphoblastic lymphoma, including acute T-cell lymphoblastic lymphoma (ATLL), and Angio-immunoblastic T-cell lymphoma. Such subjects are preferably treated with a tapered and/or elongated dosage regime as disclosed herein.

In some cases, the subject has received a diagnosis of cutaneous T-cell lymphoma, mycosis fungoides, Sezary syndrome, systemic mastocytosis, B-cell lymphoma, non-hematopoietic tumors, peripheral T cell lymphoma and histiocytic proliferation.

In some cases, the subject has received a diagnosis of a solid cancer containing CD25+ expressing infiltrating T-cells.

The Subject may be undergoing, or have undergone, a therapeutic treatment for that cancer. The subject may, or may not, have previously received ADCX25. In some cases the cancer is lymphoma, including Hodgkin's or non-Hodgkin's lymphoma.

Controls

In some cases, CD25 expression in the subject is compared to target expression in a control. Controls are useful to support the validity of staining, and to identify experimental artefacts.

In some cases, the control may be a reference sample or reference dataset. The reference may be a sample that has been previously obtained from a subject with a known degree of suitability. The reference may be a dataset obtained from analyzing a reference sample.

Controls may be positive controls in which the target molecule is known to be present, or expressed at high level, or negative controls in which the target molecule is known to be absent or expressed at low level.

Controls may be samples of tissue that are from subjects who are known to benefit from the treatment. The tissue may be of the same type as the sample being tested. For example, a sample of tumor tissue from a subject may be compared to a control sample of tumor tissue from a subject who is known to be suitable for the treatment, such as a subject who has previously responded to the treatment.

In some cases the control may be a sample obtained from the same subject as the test sample, but from a tissue known to be healthy. Thus, a sample of cancerous tissue from a subject may be compared to a non-cancerous tissue sample.

In some cases, the control is a cell culture sample.

In some cases, a test sample is analyzed prior to incubation with an antibody to determine the level of background staining inherent to that sample.

In some cases an isotype control is used. Isotype controls use an antibody of the same class as the target specific antibody, but are not immunoreactive with the sample. Such controls are useful for distinguishing non-specific interactions of the target specific antibody.

The methods may include hematopathologist interpretation of morphology and immunohistochemistry, to ensure accurate interpretation of test results. The method may involve confirmation that the pattern of expression correlates with the expected pattern. For example, where the amount of CD25 expression is analyzed, the method may involve confirmation that in the test sample the expression is observed as membrane staining, with a cytoplasmic component. The method may involve confirmation that the ratio of target signal to noise is above a threshold level, thereby allowing clear discrimination between specific and non-specific background signals.

Methods of Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount" or "effective amount" as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen. Generally, when a method of treatment describes the use of an ADC, it is intended that the ADC is used in a therapeutically-effective amount.

The actual amount administered, and rate and time-course of administration, will depend on the nature and severity of what is being treated. Prescription of treatment, e.g. decisions on dosage, is within the responsibility of general practitioners and other medical doctors. The subject may have been tested to determine their eligibility to receive the treatment according to the methods disclosed herein. The method of treatment may comprise a step of determining whether a subject is eligible for treatment, using a method disclosed herein.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Disclosed herein are methods of therapy. Also provided is a method of treatment, comprising administering to a subject in need of treatment a therapeutically-effective amount of an ADC in a fractionated dosage regime.

The ADC may comprise an anti-CD25 antibody. The anti-CD25 antibody may be HuMax-TAC™. The ADC may comprise a drug which is a PBD dimer. The ADC may be a anti-CD25-ADC, and in particular, ADCX25. The ADC may be an ADC disclosed in WO2014/057119.

The treatment may involve administration of the ADC alone or in further combination with other treatments, either simultaneously or sequentially dependent upon the condition to be treated. In sequential administration, for some cases the ADC is administered before the other treatment; for other cases the ADC is administered after the other treatment. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: Lenalidomide (REVLIMID®, Celgene), Vorinostat (ZOLINZA®, Merck), Panobinostat (FARYDAK®, Novartis), Mocetinostat (MGCD0103), Everolimus (ZORTRESS®, CERTICAN®, Novartis), Bendamustine (TREAKISYM®, RIBOMUSTIN®, LEVACT®, TREANDA®, Mundipharma International), erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gammall, calicheamicin omegall (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above. Combinations of agents may be used, such as CHP (doxorubicin, prednisone, cyclophosphamide), or CHOP (doxorubicin, prednisone, cyclophopsphamide, vincristine).

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), MDX-060 (Medarex) and the antibody drug conjugate, gemtuzumab ozogamicin (MYLOTARG®, Wyeth) or checkpoint inhibitors such as pembrolizumab (KEYTRUDA), nivolumab (Opdivo), atezolizumab (TECENTRIQ), durvalumab (IMFINZI) and ipilimumab (YERVOY).

In some cases in particular, the ADC is administered to subjects in combination with rituximab.

Humanized monoclonal antibodies with therapeutic potential as chemotherapeutic agents in combination with the conjugates of the disclosure include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Combination with Steroids

In developing the ADC dosage regimes described herein, it was observed that administration of steroids such as dexamethasone reduced the frequency and/or severity of toxicity symptom reported by subjects.

Accordingly, in preferred embodiments the ADC is administered in combination with a steroid, such as dexamethasone.

Preferably, the steroid is dexamethasone. Other suitable steroid are found in the classes of corticosteroids, such as glucocorticoids. Example glucocorticoids are Cortisol (hydrocortisone), Cortisone, Prednisone, Prednisolone, Methylprednisolone, Dexamethasone, Betamethasone, Triamcinolone, Fludrocortisone acetate, and Deoxycorticosterone acetate.

The steroid may be administered before the ADC is administered, for example at least 2 hours, at least 6 hours, at least 12 hours, or the day before the ADC is administered.

In some embodiments, a first dose of steroid is administered the day before the ADC is administered. A second dose of steroid may then be administered on the day the ADC is administered, preferably before the ADC is administered, such as at least 2 hours before the ADC is administered. A third dose of steroid may then be administered on the day after the ADC is administered. In dosing regimes comprising more than one administration of ADC per treatment cycle (e.g. fractionated dosage regimes), the steroid is preferably administered only in conjunction with the first administration of ADC in each treatment cycle.

In some embodiments, a first dose of steroid is administered the day the ADC is administered, preferably before the ADC is administered, such as at least 2 hours before the ADC is administered. A second dose of steroid may then be administered on the day after the ADC is administered. In dosing regimes comprising more than one administration of ADC per treatment cycle (e.g. fractionated dosage regimes), the steroid is preferably administered only in conjunction with the first administration of ADC in each treatment cycle.

The steroid may be administered in any method known in the art, such as orally, parenterally (e.g. injection intravenously, intramuscularly, or intrathecally), inhalation, or topically. Preferably the steroid is administered orally.

The steroid may be administered in a range of dosage regimes. For example, the dose of steroid to be administered in a day may be administered as a single dose, two partial doses, three partial doses, or more than three partial doses. Preferably partial doses are of equal size. Preferably, the dose of steroid to be administered in a day is administered as two equal, partial doses.

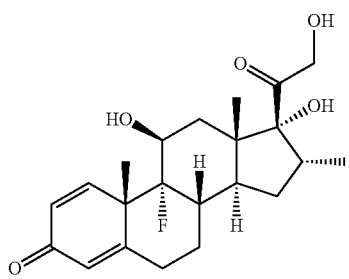

Each dose of steroid may be 1 mg, 2 mg, 3 mg, 4 mg, 5 mg, 6 mg, 7 mg, 8 mg, 9 mg, 10 mg, 11 mg, 12 mg, 14 mg, 16 mg, 18 mg, 20 mg, 22 mg, 24 mg, 26 mg, 28 mg, or 30 mg.

Each partial dose of steroid may be 1 mg, 2 mg, 3 mg, 4 mg, 5 mg, 6 mg, 7 mg, 8 mg, 9 mg, 10 mg, 11 mg, 12 mg, 13 mg, 14 mg, or 15 mg.

In some embodiments Dexamethasone is administered orally as 4 mg twice daily: (i) the day before ADC administration, (ii) the day of ADC administration, and (iii) the day after ADC administration. The steroid is administered in conjunction with the ADC administered on Week 1, Day 1 of each cycle only, regardless of ADC treatment schedule.

In some embodiments Dexamethasone is administered orally as 4 mg twice daily: (i) the day of ADC administration, at least 2 hours before the ADC, and (ii) the day after ADC administration. The steroid is administered in conjunction with the ADC administered on Week 1, Day 1 of each cycle only, regardless of ADC treatment schedule.

Dexamthasone:
(i) CAS Number→50-02-2 (see www.cas.org/content/chemical-substances/faqs)
(ii) Unique Ingredient Identifier (UNII)→7S517G3JQL (see www.fda.gov/ForIndustry/DataStandards/SubstanceRegistrationSystem-UniqueIngredientIdentifierUNII/default.htm)
(iii) IUPAC name→(8S,9R,10S,11S,13S,14S,16R,17R)-9-Fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one
(iv) Structure→

Compositions according to the present disclosure are preferably pharmaceutical compositions. Pharmaceutical compositions according to the present disclosure, and for use in accordance with the present disclosure, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

ADCx25 may be administered in combination with SGN-CD33A or inotuzumab ozogamicin.

SGN-CD33A is an anti-CD33 ADC that is also known as Vadastuximab talirine. It has the CAS number 1436390-64-5. It has the structure:

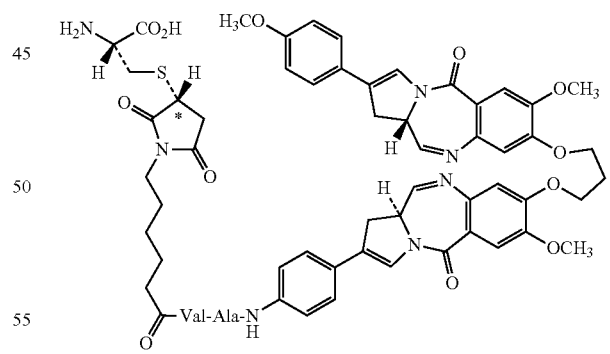

where the indicated cysteine amino acid represents cysteine residue 239 in the heavy chain of the following antibody sequence:

```
[Heavy chain]
QVQLVQSGAE   VKKPGASVKV   SCKASGYTFT   NYDINWVRQA   PGQGLEWIGW

IYPGDGSTKY   NEKFKAKATL   TADTSTSTAY   MELRSLRSDD   TAVYYCASGY
```

```
                         -continued
EDAMDYWGQG    TTVTVSSAST    KGPSVFPLAP    SSKSTSGGTA    ALGCLVKDYF

PEPVTVSWNS    GALTSGVHTF    PAVLQSSGLY    SLSSVVTVPS    SSLGTQTYIC

NVNHKPSNTK    VDKKVEPKSC    DKTHTCPPCP    APELLGGPC*V   FLFPPKPKDT

LMISRTPEVT    CVVVDVSHED    PEVKFNWYVD    GVEVHNAKTK    PREEQYNSTY

RVVSVLTVLH    QDWLNGKEYK    CKVSNKALPA    PIEKTISKAK    GQPREPQVYT

LPPSRDELTK    NQVSLTCLVK    GFYPSDIAVE    WESNGQPENN    YKTTPPVLDS

DGSFFLYSKL    TVDKSRWQQG    NVFSCSVMHE    ALHNHYTQKS    LSLSPGK

[Light chain]
DIQMTQSPSS    LSASVGDRVT    INCKASQDIN    SYLSWFQQKP    GKAPKTLIYR    50

ANRLVDGVPS    RFSGSGSGQD    YTLTISSLQP    EDFATYYCLQ    YDEFPLTFGG

GTKVEIKRTV    AAPSVFIFPP    SDEQLKSGTA    SVVCLLNNFY    PREAKVQWKV

DNALQSGNSQ    ESVTEQDSKD    STYSLSSTLT    LSKADYEKHK    VYACEVTHQG

LSSPVTKSFN    RGEC
```

Inotuzumab ozogamicin is an anti-CD22 ADC. It has the CAS number 635715-01-4 and the FDA unique ingredient identifier of P93RUU11P7.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Dosage

It will be appreciated by one of skill in the art that appropriate dosages of the ADC and compositions comprising these active elements, can vary from subject to subject. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the subject. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

In certain aspects, the dosage of ADC is determined by the expression of CD25 in a sample obtained from the subject. Thus, the level or localisation of expression of CD25 in the sample may be indicative that a higher or lower dose of ADC is required. For example, a high expression level CD25 may indicate that a higher dose of ADC would be suitable. In some cases, a high expression level of CD25 may indicate the need for administration of another agent in addition to the ADC. For example, administration of the ADC in conjunction with a chemotherapeutic agent. A high expression level of the CD25 may indicate a more aggressive therapy.

In general, a suitable dose of each active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In some situations dosage normalization based on body size parameters such as Body Surface Area (BSA) better accounts for intersubject variability in ADC pharmacokinetics such as clearance rate than normalization based on body weight. In these situations, calculation of dosage levels using body size parameters allows for more precise dosing.

Accordingly, in some aspects the dose of the ADC administered to the subject is normalised to the subject body size (i.e. not subject body weight). In some cases, the dose of the ADC administered to the subject is normalised to the subject body surface area (BSA). Preferably, the ADC dosage is normalised to BSA using the DuBois formula (as disclosed in, for example, Japanese Journal of Clinical Oncology, Volume 33, Issue 6, 1 Jun. 2003, Pages 309-313, doi.org/10.1093/jjco/hyg062).

Antibodies

The term "antibody" herein is used in the broadest sense and specifically covers monoclonal antibodies, polyclonal antibodies, dimers, multimers, multispecific antibodies (e.g., bispecific antibodies), intact antibodies (also described as "full-length" antibodies) and antibody fragments, so long as they exhibit the desired biological activity, for example, the ability to bind a first target protein (Miller et al (2003) *Jour. of Immunology* 170:4854-4861). Antibodies may be murine, human, humanized, chimeric, or derived from other species such as rabbit, goat, sheep, horse or camel.

An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by Complementarity Determining Regions (CDRs) on multiple antibodies. Each antibody that specifically binds to a different epitope has a different structure. Thus, one antigen may have more than one corresponding antibody. An antibody may comprise a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass, orallotype (e.g. human G1m1, G1m2, G1m3, non-G1m1 [that, is any allotype other than G1m1], G1m17, G2m23, G3m21, G3m28, G3m11, G3m5, G3m13, G3m14, G3m10, G3m15, G3m16, G3m6, G3m24, G3m26, G3m27, A2 ml, A2m2, Km1, Km2 and Km3) of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) *Nature*, 352:624-628; Marks et al (1991) *J. Mol. Biol.*, 222:581-597 or from transgenic mice carrying a fully human immunoglobulin system (Lonberg (2008) *Curr. Opinion* 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA*, 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Anti-CD25 antibodies are known in the art and are useful in the methods disclosed herein. These include antibodies 4C9 (obtainable from Ventana Medical Systems, Inc.). Other suitable antibodies include antibody AB12 described in WO 2004/045512 (Genmab A/S), IL2R.1 (obtainable from Life Technologies, catalogue number MA5-12680) and RFT5 (described in U.S. Pat. No. 6,383,487). Other suitable antibodies include B489 (143-13) (obtainable from Life Technologies, catalogue number MA1-91221), SP176 (obtainable from Novus, catalogue number NBP2-21755), 1B5D12 (obtainable from Novus, catalogue number NBP2-37349), 2R12 (obtainable from Novus, catalogue number NBP2-21755), or BC96 (obtainable from BioLegend, catalogue number V T-072) and M-A251 (obtainable from BioLegend, catalogue number IV A053). Other suitable anti-CD25 antibodies are daclizumab (Zenapax™) and basiliximab (Simulect™), both of which have been approved for clinical use.

BRIEF DESCRIPTION OF THE FIGURES

Embodiments and experiments illustrating the principles of the disclosure will now be discussed with reference to the accompanying figures in which:

FIG. 1.
Sequences
FIG. 2.
Subcutaeneous Karpas-e007 model—murine xenograft
FIG. 3.
Systemic Karpas299-e008 model—murine xenograft
FIG. 4.
ADCx25 Exposure versus Time Following q3w Dosing (n=19) (A) Cycle 1; (B) Cycle 2

Figure 2:
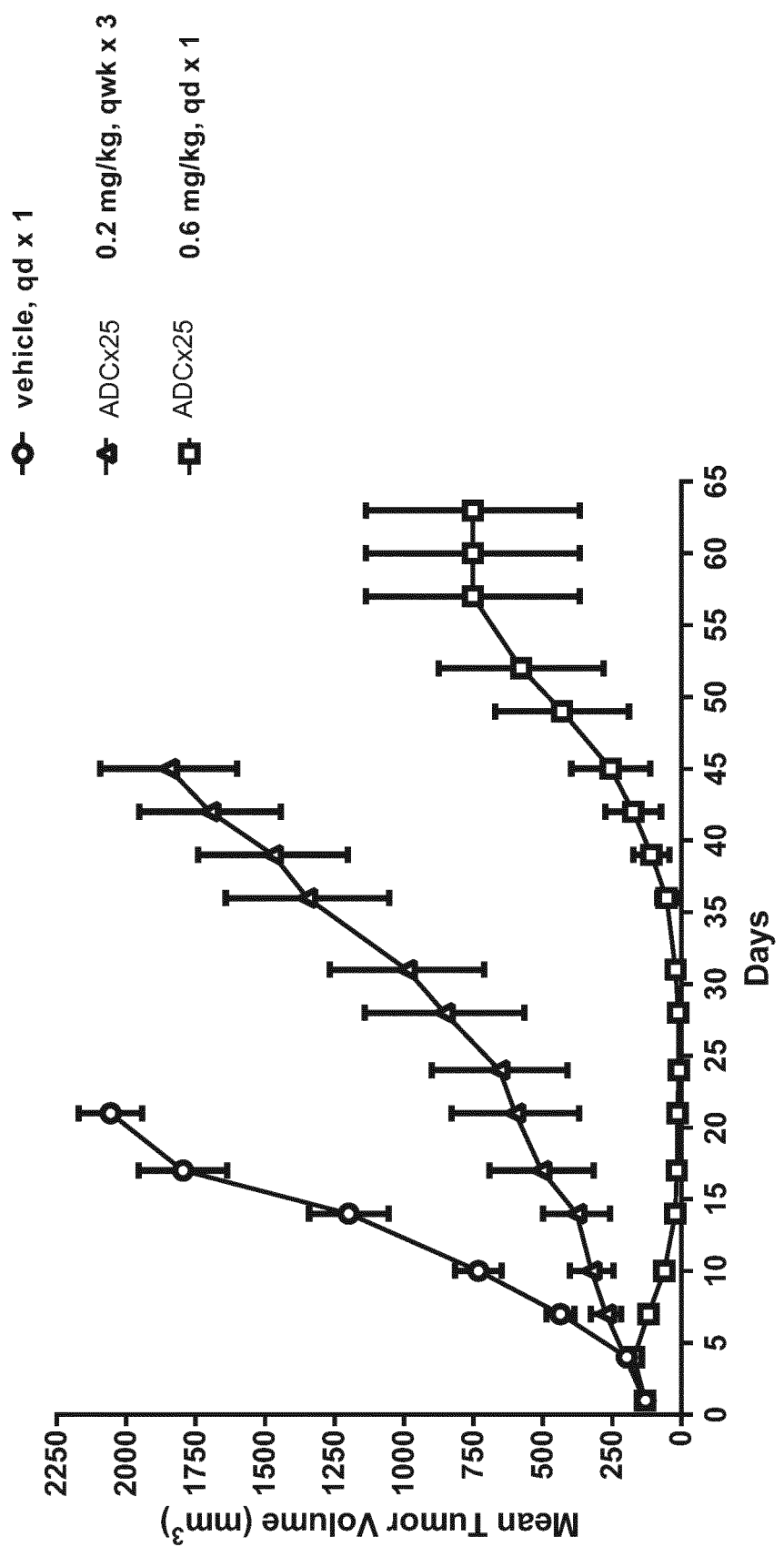

The disclosure includes the combination of the cases and preferred features described except where such a combination is clearly impermissible or expressly avoided.

The section headings used herein are for organizational purposes only and are not to be construed as limiting the subject matter described.

Cases and embodiments of the present disclosure will now be illustrated, by way of example, with reference to the accompanying figures. Further cases and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

SOME EMBODIMENTS

Fractionated Dosage Regimes

Fractionated dosage regimes in which a partial dose is administered to the subject once per week are specifically contemplated. For example, on days 1, 8, and 15 of a 21 day (3-week) treatment cycle.

Preferably each partial dose is of equal size, that is, each partial dose delivers the same amount of CD25-ADC to the subject.

Each partial dose may be 37.5, 40, 42.5, 45, 47.5, or 50 µg/kg. Preferably, each partial dose is about 40 to 60 µg/kg, such as about 45 to 55 µg/kg. Most preferably, each partial dose is about 50 µg/kg.

Preferably the CD25-ADC is ADCx25 as described herein.

Preferably the subject is human.

The use of this type of fractionated dosage regime to treat haematological cancers such as AML and ALL are embodiments of particular interest. Preferably the AML and ALL are CD25+, and may be relapsed or refractory types.

Administration of ADCx25 in combination with SGN-CD33A for the treatment of AML is envisaged. Administration of ADCx25 in combination with inotuzumab ozogamicin for the treatment of ALL is envisaged.

Preferably the CD25-ADC is administered in combination with dexamethasone, as described herein.

Tapered/Elongated Dosage Regimes

The disclosure provides a method of treating a proliferative disease in a subject, said method comprising administering to a subject a CD25-ADC, wherein the CD25-ADC is administered to the subject in a tapered and/or elongated dosage regimes.

In some cases the dosage regime comprises dosing about 120 µg/kg every 3 weeks for 2 cycles, then continuing treatment with the third and subsequent cycles at a reduced dose of about 60 µg/kg every 6 weeks, beginning 6 weeks after cycle 2 administration. Preferably only subjects who have attained at least SD after the second cycle will continue with the reduced dose and increased cycle length.

In some cases the dosage regime comprises dosing about 150 µg/kg every 3 weeks for 2 cycles, then continuing treatment with the third and subsequent cycles at a reduced dose of about 60 µg/kg every 6 weeks, beginning 6 weeks after cycle 2 administration. Preferably only subjects who have attained at least SD after the second cycle will continue with the reduced dose and increased cycle length.

In some particularly preferred cases the dosage regime comprises dosing about 150 µg/kg every 3 weeks for 2 cycles, then continuing treatment with the third and subsequent cycles at a reduced dose of about 75 µg/kg every 3 weeks, beginning 3 weeks after cycle 2 administration. Preferably only subjects who have attained at least SD after the second cycle will continue with the reduced dose.

In some cases the dosage regime comprises dosing about 200 µg/kg every 6 weeks for 2 cycles, then continuing treatment with the third and subsequent cycles at a reduced dose of about 60 µg/kg every 6 weeks, beginning 6 weeks after cycle 2 administration. Preferably only subjects who have attained at least SD after the second cycle will continue with the reduced dose.

In some cases the dosage regime comprises dosing about 200 µg/kg every 6 weeks for 1 cycle, then continuing treatment with the second and subsequent cycles at a reduced dose of about 60 µg/kg every 6 weeks, beginning 6 weeks after cycle 1 administration. Preferably only subjects who have attained at least SD after the first cycle will continue with the reduced dose.

In some cases the dosage regime comprises dosing about 45 µg/kg every 3 weeks for up to 4 treatment cycles, then continuing treatment every 3 weeks at a reduced dose of about 30 µg/kg or about 20 µg/kg (such as 20 to 30 µg/kg). In some cases, the starting dose of 45 µg/kg is administered for only 1 treatment cycle before the dose is reduced. In some cases, the starting dose of 45 µg/kg is administered for only 2 treatment cycles before the dose is reduced. In some cases, the starting dose of 45 µg/kg is administered for only 3 treatment cycles before the dose is reduced. In some cases, the starting dose of 45 µg/kg is administered for 4 treatment cycles before the dose is reduced.

Preferably the CD25-ADC is administered as single dose on Day 1 of each cycle, unless otherwise specified.

Preferably the CD25-ADC is ADCx25 as described herein.

Preferably the proliferative disease is lymphoma, such as a Hodgkin lymphoma or Non Hodgkin Lymphoma. The disease may be relapsed or refractory.

Administration of ADCx25 in combination with SGN-CD33A for the treatment of AML is envisaged. Administration of ADCx25 in combination with inotuzumab ozogamicin for the treatment of ALL is envisaged.

Preferably the subject is human.

Preferably the CD25-ADC is administered in combination with dexamethasone, as described herein.

A preferred dosage regime for subjects having, suspected of having, or having been diagnosed with Hodgkin's Lymphoma is as follows:
- about 40-50 µg/kg (preferably 45 µg/kg) of CD25-ADC Q3W (every 3 weeks) for 3 treatment cycles, followed by
- about 25-35 µg/kg (preferably 30 µg/kg) CD25-ADC Q3W (every 3 weeks) until treatment discontinued.

A preferred dosage regime for subjects having, suspected of having, or having been diagnosed with Acute T-cell lymphoblastic lymphoma (ATLL), is as follows:
- about 75-85 µg/kg (preferably 80 µg/kg) of CD25-ADC Q3W (every 3 weeks) until treatment discontinued, optionally wherein
- the dose is reduced after the first 2 or 3 treatment cycles to, for example, 40-60 µg/kg.

A preferred dosage regime for subjects having, suspected of having, or having been diagnosed with a T-cell lymphoma, is as follows:
- about 55-65 µg/kg (preferably 60 µg/kg) of CD25-ADC Q3W (every 3 weeks) until treatment discontinued, optionally wherein
- the dose is reduced after the first 2 or 3 treatment cycles to, for example, 30-40 µg/kg.

STATEMENTS OF DISCLOSURE

Fractionated Dosage Regimes

1. A method of treating a proliferative disease in a subject, said method comprising administering to a subject a CD25-ADC, wherein the CD25-ADC is administered to the subject in a fractionated dosage regime, and;
wherein the CD25-ADC comprises a conjugate of formula $L-(D^L)_p$, where $D^L$ is of formula I or II:

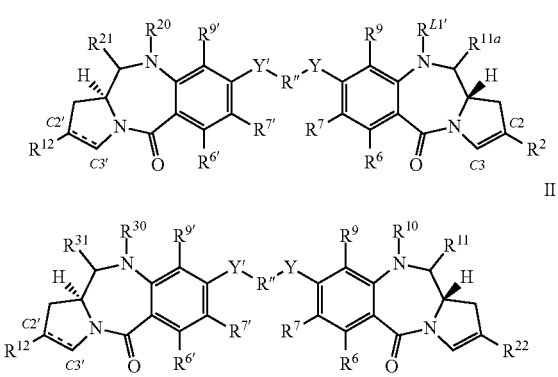

wherein:

L is an antibody (Ab) which is an antibody that binds to CD25;

when there is a double bond present between C2' and C3', $R^{12}$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

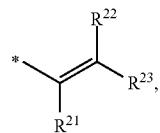

(id)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

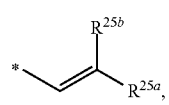

(ie)

wherein one of $R^{25a}$ and $R^{25b}$ is H and the other is selected from: phenyl, which phenyl is optionally substituted by a group selected from halo, methyl, methoxy; pyridyl; and thiophenyl; and

(if)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is

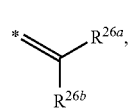

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, NH$_2$, NHR, NRR', nitro, Me$_3$Sn and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, NH$_2$, NHR, NHRR', nitro, Me$_3$Sn and halo;

R" is a $C_{3-12}$ alkylene group, which chain may be interrupted by one or more heteroatoms, e.g. O, S, NR$^{N2}$ (where $R^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

[Formula I]

$R^{L1'}$ is a linker for connection to the antibody (Ab);

$R^{11a}$ is selected from OH, $OR^A$, where $R^A$ is $C_{1-4}$ alkyl, and $SO_zM$, where z is 2 or 3 and M is a monovalent pharmaceutically acceptable cation;

$R^{20}$ and $R^{21}$ either together form a double bond between the nitrogen and carbon atoms to which they are bound or;

$R^{20}$ is selected from H and $R^C$, where $R^C$ is a capping group;

$R^{21}$ is selected from OH, $OR^A$ and $SO_zM$;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

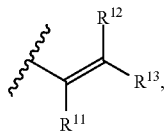

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

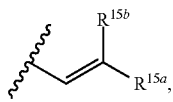

wherein one of $R^{15a}$ and $R^{15b}$ is H and the other is selected from: phenyl, which phenyl is optionally substituted by a group selected from halo, methyl, methoxy; pyridyl; and thiophenyl; and (if)

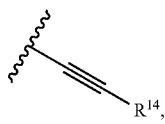

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is

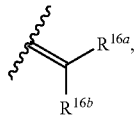

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{i6b}$ is H, the other is selected from nitrile and a $C_{1-4}$ alkyl ester;

[Formula II]

$R^{22}$ is of formula IIIa, formula IIIb or formula IIIc:

(a)

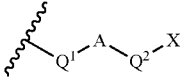

IIIa where A is a $C_{5-7}$ aryl group, and either (i) $Q^1$ is a single bond, and $Q^2$ is selected from a single bond and $-Z-(CH_2)_n-$, where Z is selected from a single bond, O, S and NH and n is from 1 to 3; or (ii) $Q^1$ is $-CH=CH-$, and $Q^2$ is a single bond;

(b)

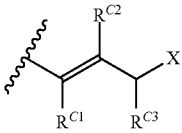

IIIb where;

$R^{C1}$, $R^{C2}$ and $R^{C3}$ are independently selected from H and unsubstituted $C_{1-2}$ alkyl;

(c)

IIIc where Q is selected from $O-R^{L2'}$, $S-R^{L2'}$ and $NR^N-R^{L2'}$, and $R^N$ is selected from H, methyl and ethyl X is selected from the group comprising: $O-R^{L2'}$, $S-R^{L2'}$, $CO_2-R^{L2'}$, $CO-R^{L2'}$, $NH-C(=O)-R^{L2'}$, $NHNH-R^{L2'}$, $CONHNH-R^{L2'}$,

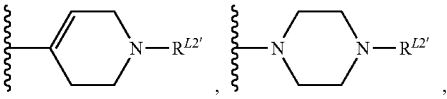

$NR^NR^{L2'}$, wherein $R^N$ is selected from the group comprising H and $C_{1-4}$ alkyl;

$R^{L2'}$ is a linker for connection to the antibody (Ab);

$R^{10}$ and $R^{11}$ either together form a double bond between the nitrogen and carbon atoms to which they are bound or;

$R^{10}$ is H and $R^{11}$ is selected from OH, $OR^A$ and $SO_zM$;

$R^{30}$ and $R^{31}$ either together form a double bond between the nitrogen and carbon atoms to which they are bound or;

$R^{30}$ is H and $R^{31}$ is selected from OH, $OR^A$ and $SO_zM$.

2. The method according to statement 1 wherein the CD25-ADC has the chemical structure:

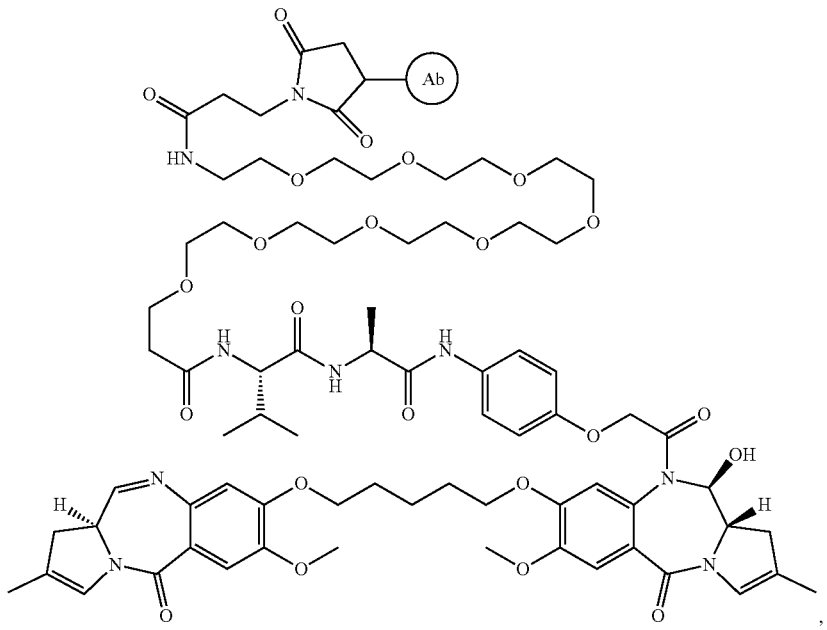

where the Ab is a CD25 antibody, and the DAR is between 1 and 8.

3. The method according to either of statement 1 or statement 2 wherein Ab comprises: a VH domain comprising a VH CDR1 with the amino acid sequence of SEQ ID NO:3, a VH CDR2 with the amino acid sequence of SEQ ID NO:4, and a VH CDR3 with the amino acid sequence of SEQ ID NO:5; and, optionally, a VL domain comprising a VL CDR1 with the amino acid sequence of SEQ ID NO:6, a VL CDR2 with the amino acid sequence of SEQ ID NO:7, and a VL CDR3 with the amino acid sequence of SEQ ID NO:8.

4. The method according to any one of statements 1 to 3 wherein Ab comprises a VH domain having the sequence of SEQ ID NO:1 and a VL domain having the sequence of SEQ ID NO:2.

5. The method according to any one of statements 1 to 4 wherein the CD25-ADC is ADCx25.

6. The method according to any preceding statement wherein the total dose of CD25-ADC administered during the treatment cycle is administered as a series of two or more partial doses during a treatment cycle.

7. The method according to any preceding statement wherein the partial doses of CD25 ADC are administered at regularly spaced intervals throughout the treatment cycle.

8. The method according to any preceding statement wherein a partial dose of CD25-ADC is administered to the subject once per week.

9. The method according to any preceding statement wherein the length of the treatment cycle is 3 weeks.

10. The method according to any preceding statement wherein the length of the treatment cycle is 6 weeks.

11. The method according to any preceding statement wherein a partial dose of the CD25-ADC is administered once a week in a 3-week treatment cycle.

12. The method according to any preceding statement wherein a partial dose of the CD25-ADC is administered on days 1, 8, and 15 of a 3-week treatment cycle.

13. The method according to any preceding statement wherein a total dose of about 10 µg/kg CD25-ADC is administered during the treatment cycle.

14. The method according to any preceding statement wherein a total dose of about 20 µg/kg CD25-ADC is administered during the treatment cycle.

15. The method according to any preceding statement wherein a total dose of about 30 µg/kg CD25-ADC is administered during the treatment cycle.

16. The method according to any preceding statement wherein a total dose of about 40 µg/kg CD25-ADC is administered during the treatment cycle.

17. The method according to any preceding statement wherein a total dose of about 50 µg/kg CD25-ADC is administered during the treatment cycle.

18. The method according to any preceding statement wherein a total dose of about 60 µg/kg CD25-ADC is administered during the treatment cycle.

19. The method according to any preceding statement wherein a total dose of about 70 µg/kg CD25-ADC is administered during the treatment cycle.

20. The method according to any preceding statement wherein a total dose of about 80 µg/kg CD25-ADC is administered during the treatment cycle.

21. The method according to any preceding statement wherein a total dose of about 90 µg/kg CD25-ADC is administered during the treatment cycle.

22. The method according to any preceding statement wherein a total dose of about 100 µg/kg CD25-ADC is administered during the treatment cycle.

22a. The method according to any preceding statement wherein a total dose of about 112.5 µg/kg CD25-ADC is administered during the treatment cycle.

23. The method according to any preceding statement wherein a total dose of about 120 µg/kg CD25-ADC is administered during the treatment cycle.

23a. The method according to any preceding statement wherein a total dose of about 127.5 µg/kg CD25-ADC is administered during the treatment cycle.

23b. The method according to any preceding statement wherein a total dose of about 135 µg/kg CD25-ADC is administered during the treatment cycle.

23c. The method according to any preceding statement wherein a total dose of about 142.5 µg/kg CD25-ADC is administered during the treatment cycle.

24. The method according to any preceding statement wherein a total dose of about 150 µg/kg CD25-ADC is administered during the treatment cycle.

25. The method according to any preceding statement wherein a total dose of about 200 µg/kg CD25-ADC is administered during the treatment cycle.

26. The method according to any preceding statement wherein a total dose of about 250 µg/kg CD25-ADC is administered during the treatment cycle.

27. The method according to any preceding statement wherein a total dose of about 300 µg/kg CD25-ADC is administered during the treatment cycle.

28. The method according to any preceding statement wherein a total dose of 1 to 10 µg/kg CD25-ADC is administered during the treatment cycle.

29. The method according to any preceding statement wherein a total dose of 11 to 20 µg/kg CD25-ADC is administered during the treatment cycle.

30. The method according to any preceding statement wherein a total dose of 21 to 30 µg/kg CD25-ADC is administered during the treatment cycle.

31. The method according to any preceding statement wherein a total dose of 31 to 40 µg/kg CD25-ADC is administered during the treatment cycle.

32. The method according to any preceding statement wherein a total dose of 41 to 50 µg/kg CD25-ADC is administered during the treatment cycle.

33. The method according to any preceding statement wherein a total dose of 51 to 60 µg/kg CD25-ADC is administered during the treatment cycle.

34. The method according to any preceding statement wherein a total dose of 61 to 70 µg/kg CD25-ADC is administered during the treatment cycle.

35. The method according to any preceding statement wherein a total dose of 71 to 80 µg/kg CD25-ADC is administered during the treatment cycle.

36. The method according to any preceding statement wherein a total dose of 81 to 90 µg/kg CD25-ADC is administered during the treatment cycle.

37. The method according to any preceding statement wherein a total dose of 91 to 100 µg/kg CD25-ADC is administered during the treatment cycle.

38. The method according to any preceding statement wherein a total dose of 101 to 120 µg/kg CD25-ADC is administered during the treatment cycle.

39. The method according to any preceding statement wherein a total dose of 121 to 140 µg/kg CD25-ADC is administered during the treatment cycle.

40. The method according to any preceding statement wherein a total dose of 141 to 160 µg/kg CD25-ADC is administered during the treatment cycle.

41. The method according to any preceding statement wherein a total dose of 161 to 180 µg/kg CD25-ADC is administered during the treatment cycle.

42. The method according to any preceding statement wherein a total dose of 181 to 200 µg/kg CD25-ADC is administered during the treatment cycle.

43. The method according to any preceding statement wherein a total dose of 201 to 220 µg/kg CD25-ADC is administered during the treatment cycle.

44. The method according to any preceding statement wherein a total dose of 221 to 240 µg/kg CD25-ADC is administered during the treatment cycle.

45. The method according to any preceding statement wherein a total dose of 241 to 260 µg/kg CD25-ADC is administered during the treatment cycle.

46. The method according to any preceding statement wherein a total dose of 261 to 280 µg/kg CD25-ADC is administered during the treatment cycle.

46. The method according to any preceding statement wherein a total dose of 281 to 300 µg/kg CD25-ADC is administered during the treatment cycle.

47. The method according to any preceding statement wherein the partial dose is about 10 µg/kg.

48. The method according to any preceding statement wherein the partial dose is about 20 µg/kg.

49. The method according to any preceding statement wherein the partial dose is about 30 µg/kg.

49a. The method according to any preceding statement wherein the partial dose is about 37.5 µg/kg.

50. The method according to any preceding statement wherein the partial dose is about 40 µg/kg.

50a. The method according to any preceding statement wherein the partial dose is about 42.5 µg/kg.

50b. The method according to any preceding statement wherein the partial dose is about 45 µg/kg.

50c. The method according to any preceding statement wherein the partial dose is about 47.5 µg/kg.

51. The method according to any preceding statement wherein the partial dose is about 50 µg/kg.

52. The method according to any preceding statement wherein the partial dose is about 60 µg/kg.

53. The method according to any preceding statement wherein the partial dose is about 70 µg/kg.

54. The method according to any preceding statement wherein the partial dose is about 80 µg/kg.

55. The method according to any preceding statement wherein the partial dose is about 90 µg/kg.

56. The method according to any preceding statement wherein the partial dose is about 100 µg/kg.

57. The method according to any preceding statement wherein the partial dose is 1 to 10 µg/kg.

58. The method according to any preceding statement wherein the partial dose is 11 to 20 µg/kg.

59. The method according to any preceding statement wherein the partial dose is 21 to 30 µg/kg.

60. The method according to any preceding statement wherein the partial dose is 31 to 40 µg/kg.

61. The method according to any preceding statement wherein the partial dose is 41 to 50 µg/kg.

62. The method according to any preceding statement wherein the partial dose is 51 to 60 µg/kg.

63. The method according to any preceding statement wherein the partial dose is 61 to 70 µg/kg.

64 The method according to any preceding statement wherein the partial dose is 71 to 80 µg/kg.

65. The method according to any preceding statement wherein the partial dose is 81 to 90 µg/kg.

66. The method according to any preceding statement wherein the partial dose is 91 to 100 µg/kg.

67. The method according to any preceding statement wherein the amount of CD25-ADC in each partial dose is the same.

68. The method according to any preceding statement wherein the proliferative disease is characterised by the presence of a neoplasm comprising CD25+ve cells 69. The method according to any preceding statement wherein the subject has been diagnosed as having the proliferative disease prior to the start of treatment with the CD25–ADC.

70. The method according to statement 69, wherein the disease is CD25+AML.

71. The method according to statement 69, wherein the disease is CD25+ALL.

72. The method according to any preceding statement wherein the method comprises the step of selecting a subject for treatment based on expression of CD25.

73. The method according to statement 72, wherein a subject is selected if at least 5% of neoplasm cells express CD25.

74. The method according to any preceding statement wherein the proliferative disease is Hodgkin's lymphoma or non-Hodgkin's lymphoma, optionally wherein the non-Hodgkin's lymphoma is selected from: Peripheral T-cell Lymphoma; Cutaneous T-cell Lymphoma; Diffuse Large B-cell Lymphoma; Follicular Lymphoma; Mantle-cell Lymphoma; Chronic Lymphocytic Leukemia; Anaplastic Large-cell Lymphoma; Acute Myeloid Leukemia (AML); Acute Lymphoblastic Leukemia (ALL) such as Philadelphia chromosome-positive ALL (Ph+ALL) or Philadelphia chromosome-negative ALL (Ph-ALL).

75. The method according to any preceding statement wherein the proliferative disease is CD25+AML.

76. The method according to any preceding statement wherein the proliferative disease is CD25+ALL.

77. The method according to any preceding statement wherein the proliferative disease is resistant, relapsed or refractory.

78. The method according to any preceding statement wherein the subject is human.

79. The method according to any preceding statement wherein the CD25-ADC is administered intravenously.

80. The method according to any preceding statement further comprising administering a chemotherapeutic agent in combination with the CD25-ADC.

81. The method according to statement 80, wherein the chemotherapeutic agent is inotuzumab ozogamicin.

82. The method according to statement 80, wherein the chemotherapeutic agent is inotuzumab SGN-CD33A.

83. The method according to any one of statements 80 to 82, wherein the chemotherapeutic agent is administered to the subject before, at the same time, or after the CD25-ADC.

84. The method according to any preceding statement, wherein the CD25-ADC is administered in combination with a steroid.

85. The method according to statement 84, wherein a first dose of steroid is administered on the same day as the ADC.

86. The method according to statement 85, wherein the first dose of steroid is administered at least 2 hours before the ADC.

87. The method according to either one of statements 85 or 86, wherein a second dose of steroid is administered the day after the ADC.

88. The method according to statement 84, wherein a first dose of steroid is administered the day before the ADC.

89. The method according to statement 88, wherein a second dose of steroid is administered on the same day as the ADC.

90. The method according to statement 89, wherein the second dose of steroid is administered at least 2 hours before the ADC.

91. The method according to either one of statements 89 or 90, wherein a third dose of steroid is administered the day after the ADC.

92. The method according to any one of statements 84 to 91, wherein the steroid or steroid doses are administered only in conjunction with the first administration of ADC in each treatment cycle.

93. The method according to any one of statements 84 to 92, wherein the steroid is administered orally.

94. The method according to any one of statements 84 to 93, wherein each dose of steroid is 8 mg.

95. The method according to any one of statements 84 to 94, wherein each dose of steroid is 16 mg.

96. The method according to any one of statements 84 to 95, wherein each dose of steroid is administered as two equal, partial doses.

97. The method according to any one of statements 84 to 96, wherein each partial dose is 4 mg.

98. The method according to any one of statements 84 to 97, wherein each partial dose is 8 mg.

99. The method according to any one of statements 84 to 98, wherein the steroid is dexamethasone.

100. The method according to statement 84, wherein 4 mg dexamethasone is administered orally twice daily: (i) the day before ADC administration on week 1, day 1 of the treatment cycle, (ii) the day of ADC administration on week 1, day 1 of the treatment cycle, and (iii) the day after ADC administration on week 1, day 1 of the treatment cycle.

101. The method according to statement 84, wherein 4 mg dexamethasone is administered orally twice daily: (i) the day of ADC administration on week 1, day 1 of the treatment cycle, and (ii) the day after ADC administration on week 1, day 1 of the treatment cycle.

102. The method according to either one of statements 100 and 101, wherein the dexamethasone administered on the same day as the ADC is administered at least two hours before the ADC.

103. The method according to any one of statements 100 to 102, wherein the dexamethasone is administered only in conjunction with the first administration of ADC in each treatment cycle.

104. The method according to any preceding statement wherein the fractionated dosage regime has lower toxicity than a single-dose dosage regime having the same total dose administered and length of treatment cycle.

105. The method according to statement 104, wherein the the incidence of TEAE with the fractionated dosage regime is no more than 50% of the incidence of TEAE in the single-dose regime.

106. The method according to statement 104, wherein the incidence of SAE with the fractionated dosage regime is no more than 50% of the incidence of SAE in the single-dose regime.

107. The method according to statement 104, wherein the incidence of DLT with the fractionated dosage regime is no more than 50% of the incidence of DLT in the single-dose regime.

108. The method according to any preceding statement wherein the fractionated dosage regime has greater efficacy than a single-dose dosage regime having the same total dose administered and length of treatment cycle.

109. The method according to statement 108, wherein the proportion of subjects achieving at least PR with the fractionated dosage regime is at least 150% of the proportion of subjects achieving at least a partial response [PR] in the single dose regime.

110. The method according to any preceding statement, wherein the subject undergoes a neurological examination prior to treatment with the ADC.

111. The method according to any preceding statement, wherein the subject undergoes a neurological examination after administration of the ADC.

112. The method according to any preceding statement, wherein the subject undergoes a neurological examination after each administration of the ADC.

113. The method according to any preceding statement, wherein the subject undergoes a neurological examination if they experience a neurologic toxicity following administration of the ADC.

114. The method according to any one of statements 110 to 111, wherein the neurological examination includes tests of strength, sensation, and/or deep-tendon reflexes.

115. The method according to any preceding statement, wherein treatment with the ADC is reduced, suspended, or permanently discontinued if the subject has a neurological disorder or experiences a neurologic toxicity.

116. The method according to any preceding statement, wherein treatment with the ADC is reduced or suspended if the subject experiences a grade 1 neurologic toxicity.

117. The method according to any preceding statement, wherein treatment with the ADC is permenantly discontinued if the subject experiences a grade 2 neurologic toxicity.

118. The method according to any one of statements 115 to 117, wherein treatment with the ADC is reduced by reducing the dose of ADC that is administered to the subject in each subsequent treatment cycle, and/or by increasing the length of each subsequent treatment cycle.

119. A method of selecting a subject for treatment by a method according to any one of statements 1 to 118, which method comprises determining if the subject has, or recently had, a neurologic disorder, wherein the subject is determined to be not suitable for treatment with the ADC if they have, or have recently had, a neurologic disorder.

120. A method of selecting a subject for treatment by a method according to any one of statements 1 to 118, which method comprises determining if the subject has, or recently had, an infection caused by a pathogen that may be associated with neurologic and/or immune-related disease; wherein the subject is determined to be not suitable for treatment with the ADC if they have, or have recently had, such an infection and/or immune-related disease.

121. The method according to any one of statements 113 to 120, wherein the neurologic disorder or neurological toxicity is polyradiculopathy, acute inflammatory demyelinating (AIDP), Guillain-Barré syndrome (GBS), myasthenia gravis, or a neurologic disorder that is linked to or is an early indicator of polyradiculitis, GBS, or myasthenia gravis, such as ascending sensory loss and/or motor weakness.

122. The method according to any one of statements 113 to 120, wherein the neurologic disorder or neurological toxicity is Guillain-Barré syndrome (GBS).

123. A method of reducing the toxicity and/or side effects associated with administration of a CD25-ADC to a subject, the method comprising administering the CD25-ADC according to the method of any preceding statement.

124. A method of increasing the treatment efficacy associated with administration of a CD25-ADC to a subject, the method comprising administering the CD25-ADC according to the method of any preceding statement.

125. A method of selecting a subject for treatment by a method according to any one of statements 1 to 122, which method comprises selecting for treatment subjects that express CD25 in a tissue of interest.

126. The method according to statement 125 wherein subjects are selected if at least 5% of cells in a sample of the tissue of interest express CD25.

127. The method according to either one of statements 123 and 124 wherein the tissue of interest is lymphoid tissue or tumour tissue.

128. The method according to any one of statements 125 to 127, wherein the subject has experienced a DLT in a single-dose dosage regime of a CD25-ADC.

129. A packaged pharmaceutical product comprising a CD25-ADC as defined in any one of statements 1 to 5, in combination with a label or insert advising that the CD25-ADC should be administered according to the method of any one of statements 1 to 122.

130. A kit comprising:
a first medicament comprising a CD25-ADC as defined in any one of statements 1 to 5; and, optionally,
a package insert or label comprising instructions for administration of the CD25-ADC according to the method of any one of statements 1 to 122.

131. A CD25-ADC as defined in any one of statements 1 to 5 for use in a method of any one of statements 1 to 122.

132. A pharmaceutical composition comprising a CD25-ADC as defined in any one of statements 1 to 5, optionally in combination with a pharmaceutically acceptable excipient, for use in a method of any one of statements 1 to 122.

133. Use of a CD25-ADC as defined in any one of statements 1 to 5 in the preparation of a medicament for use in a method of any one of statements 1 to 122.

Tapered I Elongated Dosage Regimes

1. A method of treating a proliferative disease in a subject, said method comprising administering to a subject a CD25-ADC, wherein the CD25-ADC is administered to the subject in a tapered and/or elongated dosage regime, and;
wherein the CD25-ADC comprises a conjugate of formula $L\text{-}(D^L)_p$, where $D^L$ is of formula I or II:

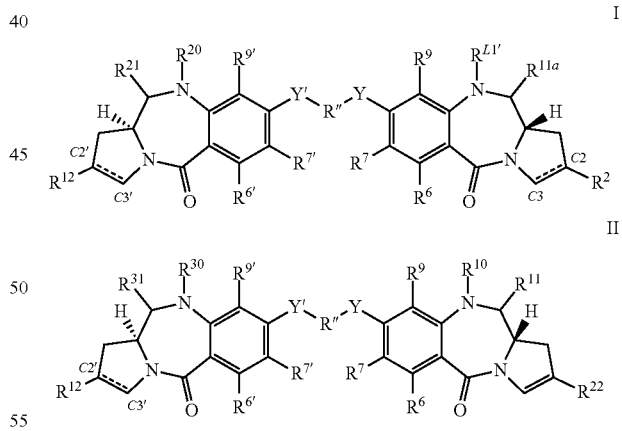

wherein:
L is an antibody (Ab) which is an antibody that binds to CD25;
when there is a double bond present between C2' and C3', $R^{12}$ is selected from the group consisting of:
(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;

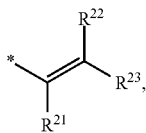
(id)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

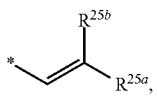
(ie)

wherein one of $R^{25a}$ and $R^{25b}$ is H and the other is selected from: phenyl, which phenyl is optionally substituted by a group selected from halo, methyl, methoxy; pyridyl; and thiophenyl; and

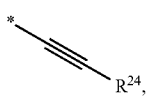
(if)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is

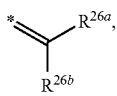

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, NH$_2$, NHR, NRR', nitro, Me$_3$Sn and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, NH$_2$, NHR, NHRR', nitro, Me$_3$Sn and halo;

R" is a $C_{3-12}$ alkylene group, which chain may be interrupted by one or more heteroatoms, e.g. O, S, NR$^{N2}$ (where R$^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

[Formula I]
$R^{L1'}$ is a linker for connection to the antibody (Ab);
$R^{11a}$ is selected from OH, OR$^A$, where R$^A$ is $C_{1-4}$ alkyl, and SO$_z$M, where z is 2 or 3 and M is a monovalent pharmaceutically acceptable cation;

$R^{20}$ and $R^{21}$ either together form a double bond between the nitrogen and carbon atoms to which they are bound or;

$R^{20}$ is selected from H and $R^C$, where $R^e$ is a capping group;

$R^{21}$ is selected from OH, OR$^A$ and SO$_z$M;

when there is a double bond present between C2 and C3, $R^2$ is selected from the group consisting of:
(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;

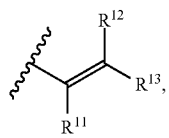
(id)

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

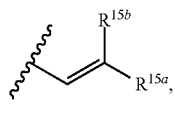
(ie)

wherein one of $R^{15a}$ and $R^{15b}$ is H and the other is selected from: phenyl, which phenyl is optionally substituted by a group selected from halo, methyl, methoxy; pyridyl; and thiophenyl; and

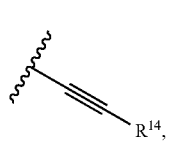
(if)

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is

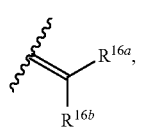

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula IIIa, formula IIIb or formula IIIc:

(a)

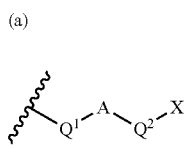

IIIa where A is a $C_{5-7}$ aryl group, and either (i) $Q^1$ is a single bond, and $Q^2$ is selected from a single bond and $-Z-(CH_2)_n-$, where Z is selected from a single bond, O, S and NH and n is from 1 to 3; or (ii) $Q^1$ is $-CH=CH-$, and $Q^2$ is a single bond;

(b)

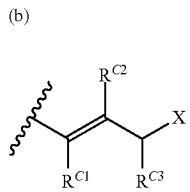

IIIb where;

$R^{C1}$, $R^{C2}$ and $R^{C3}$ are independently selected from H and unsubstituted $C_{1-2}$ alkyl;

(a)

IIIc where Q is selected from $O-R^{L2'}$, $S-R^{L2'}$ and $NR^N-R^{L2'}$, and $R^N$ is selected from H, methyl and ethyl X is selected from the group comprising: $O-R^{L2'}$, $S-R^{L2'}$, $CO_2-R^{L2'}$, $CO-R^{L2'}$, $NH-C(=O)-R^{L2'}$, $NHNH-R^{L2'}$, $CONHNH-R^{L2'}$,

$NR^N R^{L2'}$, wherein $R^N$ is selected from the group comprising H and $C_{1-4}$ alkyl;

$R^{L2'}$ is a linker for connection to the antibody (Ab);

$R^{10}$ and $R^{11}$ either together form a double bond between the nitrogen and carbon atoms to which they are bound or;

$R^{10}$ is H and $R^{11}$ is selected from OH, $OR^A$ and $SO_zM$;

$R^{30}$ and $R^{31}$ either together form a double bond between the nitrogen and carbon atoms to which they are bound or;

$R^{30}$ is H and $R^{31}$ is selected from OH, $OR^A$ and $SO_zM$.

2. The method according to statement 1 wherein the CD25-ADC has the chemical structure:

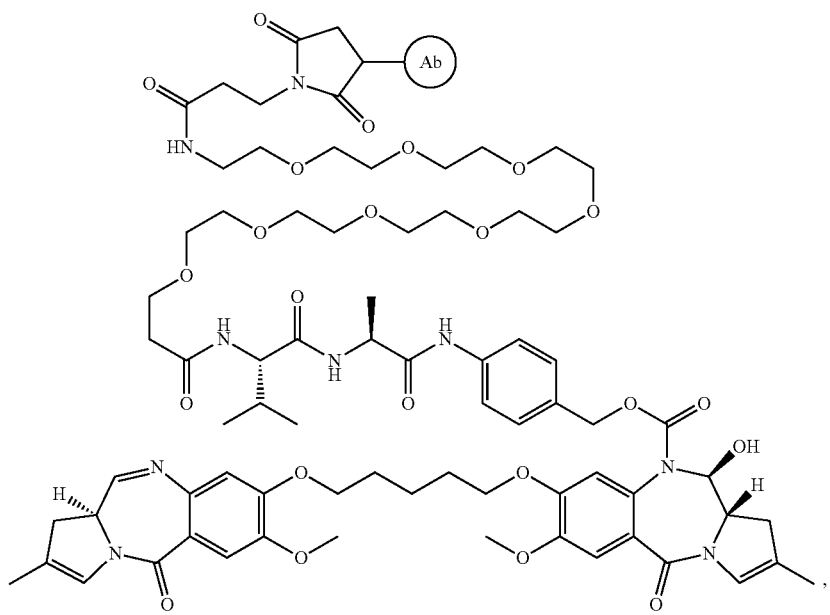

where the Ab is a CD25 antibody, and the DAR is between 1 and 8.

3. The method according to either of statement 1 or statement 2 wherein Ab comprises:
- a VH domain comprising a VH CDR1 with the amino acid sequence of SEQ ID NO:3, a VH CDR2 with the amino acid sequence of SEQ ID NO:4, and a VH CDR3 with the amino acid sequence of SEQ ID NO:5; and, optionally,
- a VL domain comprising a VL CDR1 with the amino acid sequence of SEQ ID NO:6, a VL CDR2 with the amino acid sequence of SEQ ID NO:7, and a VL CDR3 with the amino acid sequence of SEQ ID NO:8.

4. The method according to any one of statements 1 to 3 wherein Ab comprises a VH domain having the sequence of SEQ ID NO:1 and a VL domain having the sequence of SEQ ID NO:2.

5. The method according to any one of statements 1 to 4 wherein the CD25-ADC is ADCx25.

6. The method according to any preceding statement wherein the starting dose of CD25-ADC is reduced no more than twice during the dosage regime.

7. The method according to any preceding statement wherein the starting dose of CD25-ADC is reduced no more than once during the dosage regime.

8. The method according to any preceding statement wherein the dose is reduced following the first treatment cycle.

9. The method according to any preceding statement wherein the dose is reduced following the second treatment cycle.

10. The method according to any preceding statement wherein the dose is reduced following the third treatment cycle.

11. The method according to any preceding statement wherein the dose is reduced following the fourth treatment cycle.

12. The method according to any preceding statement wherein the dose is reduced only if the subject has attained at least Stable Disease [SD] at the end of the preceding treatment cycle.

13. The method according to any preceding statement wherein the starting dose is at least about 10, 15, 20, 25, 30, 35, 40, 45, 50, 55, 60, 65, 70, 75, 80, 85, 90, 95, 100, 110, 120, 130, 140, 150, 160, 170, 180, 190, or 200 µg/kg.

14. The method according to any preceding statement wherein the starting dose is about 10, 15, 20, 25, 30, 35, 40, 45, 50, 55, 60, 65, 70, 75, 80, 85, 90, 95, 100, 120, 150, 200, 250, 300, 350, 400, 450, 500, 550, or 600 µg/kg.

15. The method according to any preceding statement wherein the starting dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240 µg/kg, 241 to 260 µg/kg, 261 to 280 µg/kg, 281 to 300 µg/kg, 301 to 320 µg/kg, 321 to 340 µg/kg, 341 to 360 µg/kg, 361 to 380 µg/kg, 381 to 400 µg/kg, 401 to 420 µg/kg, 421 to 440 µg/kg, 441 to 460 µg/kg, 461 to 480 µg/kg, 481 to 500 µg/kg, 501 to 520 µg/kg, 521 to 540 µg/kg, 541 to 560 µg/kg, 561 to 580 µg/kg, or 581 to 600 µg/kg.

16. The method according to any preceding statement wherein the starting dose is 40 to 50 µg/kg, such as about 45 µg/kg.

17. The method according to any preceding statement wherein the starting dose is 55 to 65 µg/kg, such as about 60 µg/kg.

18. The method according to any preceding statement wherein the starting dose is 75 to 85 µg/kg, such as about 80 µg/kg.

19. The method according to any preceding statement wherein the starting dose is at least 120 µg/kg.

20. The method according to any preceding statement wherein the starting dose is about 120 µg/kg.

21. The method according to any preceding statement wherein the starting dose is at least 150 µg/kg.

22. The method according to any preceding statement wherein the starting dose is about 140 to 160 µg/kg, such as 150 µg/kg.

23. The method according to any preceding statement wherein the starting dose is at least 200 µg/kg.

24. The method according to any preceding statement wherein the starting dose is about 200 µg/kg.

25. The method according to any preceding statement wherein the the reduced dose is about 10, 20, 30, 40, 50, 60, 70, 80, 90, 100, 120, 150, 200, 250, or 300 µg/kg.

26. The method according to any preceding statement wherein the reduced dose is 1 to 10 µg/kg, 11 to 20 µg/kg, 21 to 30 µg/kg, 31 to 40 µg/kg, 41 to 50 µg/kg, 51 to 60 µg/kg, 61 to 70 µg/kg, 71 to 80 µg/kg, 81 to 90 µg/kg, 91 to 100 µg/kg, 101 to 120 µg/kg, 121 to 140 µg/kg, 141 to 160 µg/kg, 161 to 180 µg/kg, 181 to 200 µg/kg, 201 to 220 µg/kg, 221 to 240 µg/kg, 241 to 260 µg/kg, 261 to 280 µg/kg, or 281 to 300 µg/kg.

27. The method according to any preceding statement wherein the reduced dose is 15 to 35 µg/kg, such as about 20 µg/kg or about 30 µg/kg.

28. The method according to any preceding statement wherein the reduced dose is 25 to 35 µg/kg, such as about 30 µg/kg.

29. The method according to any preceding statement wherein the reduced dose is 35 to 45 µg/kg, such as about 40 µg/kg.

30. The method according to any preceding statement wherein the reduced dose is 45 to 55 µg/kg, such as about 50 µg/kg.

31. The method according to any preceding statement wherein the reduced dose is 55 to 65 µg/kg, such as about 60 µg/kg.

32. The method according to any preceding statement wherein the reduced dose is about 60 µg/kg.

33. The method according to any preceding statement wherein the reduced dose is about 70 to 80 µg/kg, such as 75 µg/kg.

34. The method according to any preceding statement wherein each treatment cycle is the same length.

35. The method according to statement 34, wherein each treatment cycle is 3 weeks.

36. The method according to statement 35, wherein about 140 to 160 µg/kg of CD25-ADC are administered for two, 3-week treatment cycles,
followed by subsequent 3-week cycles of 70 to 80 µg/kg beginning 3 weeks after the cycle 2 administration.

37. The method according to statement 36, wherein about 150 µg/kg of CD25-ADC are administered for two, 3-week treatment cycles,
followed by subsequent 3-week cycles of 75 µg/kg beginning 3 weeks after the cycle 2 administration.

38. The method according to statement 35, wherein about 40 to 50 µg/kg of CD25-ADC are administered for three, 3-week treatment cycles,
followed by subsequent 3-week cycles of 25 to 35 µg/kg beginning 3 weeks after the cycle 3 administration.

37. The method according to statement 38, wherein about 45 μg/kg of CD25-ADC are administered for three, 3-week treatment cycles,
followed by subsequent 3-week cycles of 30 μg/kg beginning 3 weeks after the cycle 3 administration.

38. The method according to statement 34, wherein each treatment cycle is 6 weeks.

39. The method according to statement 38, wherein about 200 μg/kg of CD25-ADC are administered for two, 6-week treatment cycles,
followed by subsequent 6-week cycles of 60 μg/kg beginning 6 weeks after the cycle 2 administration.

40. The method according to statement 38, wherein about 200 μg/kg of CD25-ADC are administered for one, 6-week treatment cycle,
followed by subsequent 6-week cycles of 60 μg/kg beginning 6 weeks after the cycle 1 administration.

41. The method according to any one of statements 1 to 33, wherein the treatment cycle length is increased no more than twice during the dosage regime.

42. The method according to any one of statements 1 to 33 or 41, wherein the treatment cycle length is increased no more than once during the dosage regime.

43. The method according to any one of statements 1 to 33 or 41 to 42, wherein the treatment cycle length is increased following the first treatment cycle.

44. The method according to any one of statements 1 to 33 or 41 to 43, wherein the treatment cycle length is increased following the second treatment cycle.

45. The method according to any one of statements 1 to 33 or 41 to 44, wherein the cycle length is increased only if the subject has attained at least Stable Disease [SD] at the end of the preceding treatment cycle.

46. The method according to any one of statements 1 to 33 or 41 to 45, wherein 'Day 1' of the first treatment cycle of increased length is delayed so that the time elapsed between 'Day 1' of the final shorter treatment cycle and 'Day 1' of the first treatment cycle of increased length is equal in length to the increased treatment cycle.

47. The method according to any one of statements 1 to 33 or 41 to 46, wherein the starting length is 3 weeks.

48. The method according to any one of statements 1 to 33 or 41 to 47, wherein the increased length is 6 weeks.

49. The method according to statement 48, wherein about 150 μg/kg of CD25-ADC are administered for two, 3-week treatment cycles,
followed by subsequent 6-week cycles of 60 μg/kg beginning 6 weeks after the cycle 2 administration.

50. The method according to statement 48, wherein about 120 μg/kg of CD25-ADC are administered for two, 3-week treatment cycles, followed by subsequent 6-week cycles of 60 μg/kg beginning 6 weeks after the cycle 2 administration.

51. The method according to any preceding statement, wherein the CD25-ADC is administered as a single dose.

52. The method according to any preceding statement, wherein the dose of CD25-ADC is administered on Day 1 of the treatment cycle.

53. The method according to any preceding statement wherein the proliferative disease is characterised by the presence of a neoplasm comprising CD25+ve cells 54. The method according to any preceding statement wherein the subject has been diagnosed as having the proliferative disease prior to the start of treatment with the CD25-ADC.

55. The method according to any preceding statement wherein the method comprises the step of selecting a subject for treatment based on expression of CD25.

56. The method according to statement 57, wherein a subject is selected if at least 5% of neoplasm cells express CD25.

57. The method according to any preceding statement wherein the proliferative disease is lymphoma.

58. The method according to statement 57 wherein the proliferative disease is Hodgkin's lymphoma.

59. The method according to statement 57, wherein the lymphoma is Non-Hodgkin Lymphoma (NHL).

60. The method according to statement 59, wherein the non-Hodgkin's lymphoma is either:
(a) a B-cell lineage lymphoma such as diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL); or
(b) a T-cell lineage lymphoma, such as Extranodal T cell lymphoma, Cutaneous T-cell lymphomas (Sézary syndrome and Mycosis fungoides), Anaplastic large cell lymphoma, T-cell lymphoblastic lymphoma, including acute T-cell lymphoblastic lymphoma (ATLL), and Angioimmunoblastic T-cell lymphoma.

61. The method according to statement 59, wherein the non-Hodgkin's lymphoma is acute T-cell lymphoblastic lymphoma (ATLL).

62. The method according to statement 59, wherein the non-Hodgkin's lymphoma is a T-cell lineage lymphoma.

63. The method according to any one of statements 1 to 56 wherein the proliferative disease is a T-cell lineage leukaemia, such as Large granular lymphocytic leukaemia, adult T-cell leukaemia, or T-cell prolymphocytic leukaemia.

64. The method according to any preceding statement wherein the proliferative disease is resistant, relapsed or refractory.

65. The method according to any preceding statement wherein the subject is human.

66. The method according to any preceding statement wherein the CD25-ADC is administered intravenously.

67. The method according to any preceding statement, further comprising administering a chemotherapeutic agent in combination with the CD25-ADC; optionally wherein the chemoptherpeutic agent is inotuzumab ozogamicin, inotuzumab SGN-CD33A, or a checkpoint inhibitor, such as ibrutinib and durvalumab.

68. The method according to statement 67, wherein the chemotherapeutic agent is administered to the subject before, at the same time, or after the CD25-ADC.

69. The method according to any preceding statement, wherein the CD25-ADC is administered in combination with a steroid.

70. The method according to statement 69, wherein a first dose of steroid is administered on the same day as the ADC.

71. The method according to statement 60, wherein the first dose of steroid is administered at least 2 hours before the ADC.

72. The method according to either one of statements 69 or 70, wherein a second dose of steroid is administered the day after the ADC.

73. The method according to statement 69, wherein a first dose of steroid is administered the day before the ADC.

74. The method according to statement 73, wherein a second dose of steroid is administered on the same day as the ADC.

75. The method according to statement 74, wherein the second dose of steroid is administered at least 2 hours before the ADC.

76. The method according to either one of statements 74 or 75, wherein a third dose of steroid is administered the day after the ADC.

77. The method according to any one of statements 69 to 76, wherein the steroid or steroid doses are administered only in conjunction with the first administration of ADC in each treatment cycle.

78. The method according to any one of statements 69 to 77, wherein the steroid is administered orally.

79. The method according to any one of statements 69 to 78, wherein each dose of steroid is 8 mg.

80. The method according to any one of statements 69 to 79, wherein each dose of steroid is 16 mg.

81. The method according to any one of statements 69 to 80, wherein each dose of steroid is administered as two equal, partial doses.

82. The method according to any one of statements 69 to 81, wherein each partial dose is 4 mg.

83. The method according to any one of statements 69 to 82, wherein each partial dose is 8 mg.

84. The method according to any one of statements 69 to 83, wherein the steroid is dexamethasone.

85. The method according to statement 69, wherein 4 mg or 8 mg dexamethasone is administered orally twice daily: (i) the day before ADC administration on week 1, day 1 of the treatment cycle, (ii) the day of ADC administration on week 1, day 1 of the treatment cycle, and (iii) the day after ADC administration on week 1, day 1 of the treatment cycle.

86. The method according to statement 69, wherein 4 mg or 8 mg dexamethasone is administered orally twice daily: (i) the day of ADC administration on week 1, day 1 of the treatment cycle, and (ii) the day after ADC administration on week 1, day 1 of the treatment cycle.

87. The method according to either one of statements 85 and 86, wherein the dexamethasone administered on the same day as the ADC is administered at least two hours before the ADC.

88. The method according to any one of statements 85 to 87, wherein the dexamethasone is administered only in conjunction with the first administration of ADC in each treatment cycle.

89. The method according to any preceding statement wherein the tapered and/or elongated dosage regime has lower toxicity than a single-dose dosage regime a dosage regime having constant dosage level and cycle length, optionally wherein the constant dose level and cycle length of the comparator regime is the same as the starting dose and starting length of the tapered and/or elongated regime.

90. The method according to statement 89, wherein the the incidence of TEAE with the tapered and/or elongated dosage regime is no more than 50% of the incidence of TEAE in the constant dose level and cycle length regime.

91. The method according to statement 90, wherein the incidence of SAE with the tapered and/or elongated dosage regime is no more than 50% of the incidence of SAE in the constant dose level and cycle length regime.

92 The method according to statement 89, wherein the incidence of DLT with the tapered and/or elongated dosage regime is no more than 50% of the incidence of DLT in the constant dose level and cycle length regime.

93. The method according to any preceding statement wherein the tapered and/or elongated dosage regime has greater efficacy than a dosage regime having constant dosage level and cycle length, optionally wherein the constant dose level and cycle length of the comparator regime is the same as the starting dose and starting length of the tapered and/or elongated regime.

94. The method according to statement 93, wherein the proportion of subjects achieving at least PR with the tapered and/or elongated dosage regime is at least 150% of the proportion of subjects achieving at least a partial response [PR] in the constant dose level and cycle length regime.

95. The method according to any preceding statement, wherein the subject undergoes a neurological examination prior to treatment with the ADC.

96. The method according to any preceding statement, wherein the subject undergoes a neurological examination after administration of the ADC.

97. The method according to any preceding statement, wherein the subject undergoes a neurological examination after each administration of the ADC.

98. The method according to any preceding statement, wherein the subject undergoes a neurological examination if they experience a neurologic toxicity following administration of the ADC.

99. The method according to any one of statements 95 to 98, wherein the neurological examination includes tests of strength, sensation, and/or deep-tendon reflexes.

100. The method according to any preceding statement, wherein treatment with the ADC is reduced, suspended, or permanently discontinued if the subject has a neurological disorder or experiences a neurologic toxicity.

101. The method according to any preceding statement, wherein treatment with the ADC is reduced or suspended if the subject experiences a grade 1 neurologic toxicity.

102. The method according to any preceding statement, wherein treatment with the ADC is permanently discontinued if the subject experiences a grade 2 neurologic toxicity.

103. The method according to any one of statements 100 to 102, wherein treatment with the ADC is reduced by reducing the dose of ADC that is administered to the subject in each subsequent treatment cycle, and/or by increasing the length of each subsequent treatment cycle.

104. A method of selecting a subject for treatment by a method according to any one of statements 1 to 103, which method comprises determining if the subject has, or recently had, a neurologic disorder, wherein the subject is determined to be not suitable for treatment with the ADC if they have, or have recently had, a neurologic disorder.

105. A method of selecting a subject for treatment by a method according to any one of statements 1 to 103, which method comprises determining if the subject has, or recently had, an infection caused by a pathogen that may be associated with neurologic and/or immune-related disease; wherein the subject is determined to be not suitable for treatment with the ADC if they have, or have recently had, such an infection and/or immune-related disease.

106. The method according to any one of statements 98 to 105, wherein the neurologic disorder or neurological toxicity is polyradiculopathy, acute inflammatory demyelinating (AIDP), Guillain-Barré syndrome (GBS), myasthenia gravis, or a neurologic disorder that is linked to or is an early indicator of polyradiculitis, GBS, or myasthenia gravis, such as ascending sensory loss and/or motor weakness.

107. The method according to any one of statements 98 to 105, wherein the neurologic disorder or neurological toxicity is Guillain-Barré syndrome (GBS).

108. A method of reducing the toxicity and/or side effects associated with administration of a CD25-ADC to a subject, the method comprising administering the CD25-ADC according to the method of any preceding statement.

109. A method of increasing the treatment efficacy associated with administration of a CD25-ADC to a subject, the method comprising administering the CD25-ADC according to the method of any preceding statement.

110. A method of selecting a subject for treatment by a method according to any one of statements 1 to 107, which method comprises selecting for treatment subjects that express CD25 in a tissue of interest.

111. The method according to statement 110 wherein subjects are selected if at least 5% of cells in a sample of the tissue of interest express CD25.

112. The method according to either one of statements 110 and 101 wherein the tissue of interest is lymphoid tissue or tumour tissue.

113. The method according to any one of statements 110 to 112, wherein the subject has experienced a DLT in a constant dose and or constant cycle length dosage regime of a CD25-ADC.

114. A packaged pharmaceutical product comprising a CD25-ADC as defined in any one of statements 1 to 5, in combination with a label or insert advising that the CD25-ADC should be administered according to the method of any one of statements 1 to 113.

115. A kit comprising:
a first medicament comprising a CD25-ADC as defined in any one of statements 1 to 5; and, optionally,
a package insert or label comprising instructions for administration of the CD25-ADC according to the method of any one of statements 1 to 113.

116. A CD25-ADC as defined in any one of statements 1 to 5 for use in a method of any one of statements 1 to 113.

117. A pharmaceutical composition comprising a CD25-ADC as defined in any one of statements 1 to 5, optionally in combination with a pharmaceutically acceptable excipient, for use in a method of any one of statements 1 to 113.

118. Use of a CD25-ADC as defined in any one of statements 1 to 5 in the preparation of a medicament for use in a method of any one of statements 1 to 113.

EXAMPLES

Example 1: Efficacy of ADCx25 Treatment in Mouse Xenograft In Vivo Model

Subcutaeneous Karpas-e007 Model

Female severe combined immunodeficient mice (Fox Chase SCID®, C.B-17/lcr-Prkdcscid, Charles River) were eight weeks old with a body weight (BW) range of 16.5 to 21.3 grams on Day 1 of the study.

On the day of tumor implant, each test mouse received 1×107 Karpas-299 cells (0.1 mL cell suspension in PBS) implanted subcutaneously in the right flank. Tumor growth was monitored as the average size approached the target range of 100 to 150 mm3. Twelve days after tumor implantation, designated as Day 1 of the study, the animals were sorted into groups, each consisting of ten mice, with individual tumor volumes of 88 to 196 mm3 and group mean tumor volumes of 122 to 137 mm3. Tumors were measured in two dimensions using calipers, and volume was calculated using the formula:

Tumor Volume(mm3)=$w2 \times l/2$ where w=width and l=length, in mm, of the tumor. Tumor weight may be estimated with the assumption that 1 mg is equivalent to 1 mm3 of tumor volume.

All treatments were administered intravenously (i.v.). The dosing volume was 0.2 mL per 20 grams of body weight (10 mL/kg), and was scaled to the body weight of each individual animal. Tumors were measured using calipers twice per week, and each animal was euthanized when its tumor reached the endpoint volume of 2000 mm3 or at the end of the study (Day 63), whichever came first.

In one group of animals, 0.6 mg/kg ADCx25 was administered as a single dose on day 1 (qd×1).

In the other group, the same dose of ADCx25 was administered as 3 fractionated doses i.e. 3 doses each of 0.2 mg/kg at 1 week intervals (qwk×3).

It was observed that in the group receiving the fractionated dose, tumour size grew steadily throughout the study. In contrast, the group receiving the single dose on day 1 showed no significant tumour mass until ~day 30 (see FIG. 2).

Systemic Karpas299-e008 Model

Female severe combined immunodeficient mice (Fox Chase SCID®, C.B-17/lcr-Prkdcscid, Charles River) were eight weeks old with a body weight (BW) range of 15.5 to 23.6 grams on Day 1 of the study.

On the day of tumor implantation, Karpas 299 cells were harvested during mid-log phase growth and resuspended in PBS. The mice each received 1×107 cells (0.2 mL cell suspension) via a bolus tail vein injection. Twelve days after tumor cell injection, the mice were randomized into nine groups (n=10/group) and dosing was initiated. The first day of dosing was designated as Day 1 of the study. Each ADC and the PBS vehicle were administered intravenously (i.v.). The dosing volume of 0.2 mL/20 g mouse (10 mL/kg) was scaled to the last recorded weight of each animal.

The study endpoint was death or moribundity due to disseminated Karpas 299 lymphoma progression.

Animals were weighed twice weekly for the duration of the study, starting on Day 1, and were frequently examined for overt signs of tumor progression such as ocular proptosis and loss of hind limb function.

Animals were euthanized if they were unable to ambulate or were moribund. Each animal found dead, or euthanized, because of tumor progression was recorded as a death on survival study (DSS). The day of death or euthanasia represented the time to endpoint (TTE). Animals that did not reach the endpoint were euthanized at the end of the study, and assigned a TTE value equal to the last day (63 days).

In one group of animals, 0.6 mg/kg ADCx25 was administered as a single dose on day 1 (qd×1).

In two other groups, the same dose of ADCx25 was administered as 3 fractionated doses i.e. 3 doses each of 0.2 mg/kg. In one group the doses were administered at 1 week intervals (qwk×3), in the second group the doses were administered at 4-day intervals (day 1, 5, 9).

Figure 3:
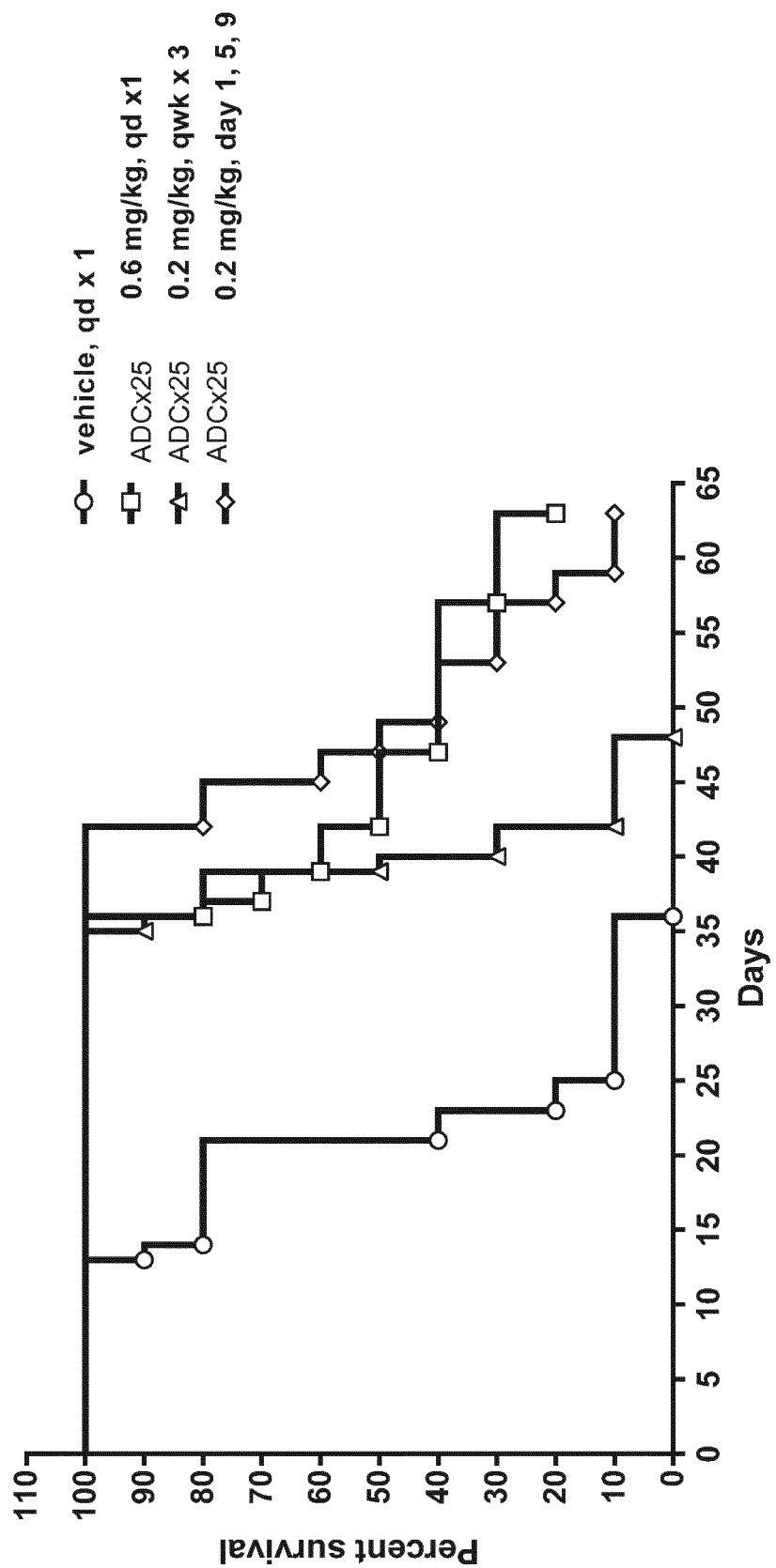

It was observed that in both groups receiving the fractionated dose, mortality rates were higher and occurred sooner in the study, with the effect more pronounced in the weekly dosing than the 4-day dosing (see FIG. 3).

Example 2: Myeloblast Count of AML Patients

ADCx25 was administered to 25 patients with relapsed or refractory CD25+ acute myeloid leukemia (AML) comprising 8 dose cohorts (3, 6, 12, 22, 32, 52, 72, and 92 µg/kg), using a 3-week treatment cycle with a single-dose administered on day 1.

Two patients were observed to have transient significant decrease in their peripheral myeloblast count (>70% to 2% in one patient and 38 to 1% in the other) but the percentage of myeloblasts in the peripheral blood increased prior to the scheduled subsequent dose (three-week intervals between doses). No dose-limiting toxicities (DLTs) or significant toxicities were reported.

The full clinical study protocol for the 3-week treatment cycle with a single-dose administered on day 1 is publically available at www.clinical trials.gov, having the ClinicalTrials.gov unique identifier: NCT02588092 (27 Apr. 2017 update).

Example 3: Pharmokinetics of ADCx25

Preliminary pharmacokinetic (PK) information was obtained from 12 patients on a 3-week treatment cycle with a single-dose administered on day 1 (3 patients each at 6, 12, 22 and 32 µg/kg). Collection of data was done in the standard manner (see full clinical study protocol NCT02588092 referenced above for more details).

The data suggests that peak exposure is dose-related. ADCx25 is rapidly cleared, with concentrations less than the lower limit of quantification for most patients through the 22 µg/kg dose group by Day 7.

Example 4: Synopsis of Fractionated Dosage Protocol

Indication

Patients with relapsed or refractory cluster of differentiation 25 (CD25)-positive acute myeloid leukemia (AML) or CD25-positive acute lymphoblastic leukemia (ALL) who have failed, or are intolerant to, any established therapy known to provide clinical benefit at current state of disease. Patients with myelodysplastic syndrome who have received treatment with hypomethylating agents and subsequently present with CD25+AML and who failed, or are ineligible for standard induction therapy, are eligible for treatment with ADCx25.

Objectives

Primary Objectives:

The primary objectives for Part 1 (dose-escalation) and Part 2 (expansion) of the study are:

Evaluate the safety and tolerability and determine the maximum tolerated dose (MTD) of ADCX25 in patients with CD25-positive relapsed or refractory AML and CD25-positive ALL (Part 1).

Determine the recommended dose of ADCX25 for Part 2.

Evaluate the safety and tolerability of ADCX25 in Part 2 at the dose level recommended in Part 1.

Secondary Objectives:

The secondary objectives for Part 1 and Part 2 of the study are:

Evaluate the clinical activity of ADCX25, based on the patient's response to treatment (complete response [CR], CR with incomplete blood count recover [CRi], partial response [PR], progressive disease [PD], no response [NR]) and determination of the overall duration of response (DOR), overall response rate (ORR), overall survival (OS), and progression-free survival (PFS).

Characterize the pharmacokinetic (PK) profile of ADCX25 (total antibody, drug-to-antibody ratio [DAR]≥0), PBD-conjugated antibody (DAR≥1), and free warhead SG3199.

Evaluate anti-drug antibodies (ADAs) to ADCX25 in blood before, during, and after treatment with ADCX25.

Efficacy Assessment

Assessment of response to treatment with ADCX25 will be based on bone marrow samples (aspirate or biopsy, if aspirate unattainable). The activity of ADCX25 will be evaluated based on the Investigator's evaluation of the patient's response to ADCX25 as CR, CRi, PR, PD, or NR as defined herein.

PK Assessment

The PK profile of ADCX25 (total antibody; drug-to-antibody ratio [DAR]≥0), PBD-conjugated antibody (DAR≥1), and free warhead will be assessed. Additional PK, ADA, cytokines, and serum CD25 (sCD25); blood samples will be collected at the discretion of the Investigator during any visit where toxicity is observed. A PK, ADA, cytokines, and sCD25 sample will also be collected concurrently with any other blood draw to assess safety (e.g., Unscheduled Visit), if possible. The PK profile will include determination of standard PK parameters (e.g., maximum concentration [Cmax], time to Cmax [Tmax], AUC0-last, AUC0-τ, AUC0-□, Al, Vss, MRT, λz, t½, CL, and Vz.).

Safety Assessment

Safety will be assessed based on AEs, serious AEs (SAEs), treatment discontinuations due to AEs, DLTs (as defined herein) measurements of cytokines in serum, periodic 12-lead electrocardiogram (ECG) recordings, physical examinations, vital signs measurements, ECOG performance status, and hematology, biochemistry, coagulation panel, pregnancy testing (for women of child-bearing potential) and urinalysis test results. Adverse events will be graded according to CTCAE Version 4.0 (v4.03, published Jun. 14, 2010; NIH Publication No. 09-5410).

Product Dosage and Mode of Administration

ADCX25 is a sterile formulation containing PBD-conjugated HuMax®-TAC (DAR≥1), HuMax®-TAC (DAR=0), and SG3249. It is provided pre-formulated in 10-mL glass vials containing approximately 30 mg of ADCX25 per vial (deliverable volume 5.4 mL at 6 mg/mL). The appropriate quantity of ADCX25 will be diluted in 50 mL of 5% dextrose in water (D5W).

Patients will receive a 1-hour intravenous (IV) infusion of ADCX25 on Day 1 of Cycle 1. If ADCX25 is well tolerated after the first infusion, the infusion duration may be shortened to 30 minutes for subsequent cycles for that patient, at the Investigator's discretion.

The investigational product administration schedule is as follows:

Patients will be given ADCX25 (weekly [QW]) on Days 1, 8, and 15 of each 3-week (21-day) treatment cycle.

A patient will maintain the same treatment schedule throughout the duration of the trial.

Once a patient achieves CR/CRi, frequency or dose may be adjusted by the DESC based on emerging safety, efficacy, and PK profile.

The trial will be continuously monitored for emerging safety, efficacy and/or PK profile, and the DESC will determine if it is appropriate to maintain a QW schedule, revert to an every 3-week (Q3W) schedule, or test other dosing regimens.

Dose Escalation Design

Dose-escalation (Part 1) will be conducted according to a 3+3 design. The initial dose of ADCX25 will be 3 µg/kg (Dose Level 1), and the highest allowed dose will be 300 µg/kg.

The DLT observation period for dose-escalation will be 1 cycle. The first patient at each new dose level must be observed for 7 days for occurrence of AEs prior to treating the second patient at that dose level. Patients will be entered sequentially to each dose level.

For each dose level, if none of the first 3 patients at that level experiences a DLT, new patients may be entered at the next higher dose level. If 1 of 3 patients experiences a DLT, up to 3 more patients are to be treated at that same dose level. If none of the additional 3 patients at that dose level experiences a DLT, new patients may then be entered at the next higher dose level. However, if 1 or more of the additional 3 patients experience a DLT, then no further patients are to be started at that dose level and the preceding dose is identified as the MTD. The MTD; therefore, is defined as the highest dose level at which none of the first 3 treated patients, or no more than 1 of the first 6 treated patients, experiences a DLT.

No intra-patient dose-escalation is allowed.

The number of dose levels will depend on the emergent toxicity profile of ADCX25 and will be decided by the DESC; PK and PD evaluations may also inform decision making. During Part 1 (dose-escalation), the DESC may expand enrolment at doses below the current dose level as part of the dose-escalation process.

Additional patients may only be added at a lower dose level provided there is at least 1 patient who has achieved a PR or better (Section 7.1). No more than 10 patients in total can be treated at any dose level unless ≥3 of the 10 patients have achieved a PR or better.

Patients will be given ADCX25 (QW) on Days 1, 8 and 15 of each 3-week treatment cycle.

The first dose level for the weekly fractionated dosage regime/3 week treatment cycle (QW) dosing will be based on the safety and tolerability of patients who have been treated on the single dose/3-week treatment cycle schedule (Q3W). The first 3 patients will be given a cumulative dose each cycle that is comparable to (but not higher than) the highest dose tested at the Q3W dose schedule at which 3 patients completed the DLT observation period without a DLT. For example, if the highest Q3W dose tested at which 3 patients did not experience a DLT was cohort 92 µg/kg, the first cohort to receive QW dosing will receive 30 µg/kg each week for 3 weeks.

When the dose is escalated, the dose may increase by 50% if no DLTs are observed at the current level. Once a DLT is observed at a given dose level, the next dose may only increase by 25%. The dose may never increase by more than 50%, or more than an absolute value of 20 µg/kg/week, whichever is less. During Part 1, the DESC may expand enrolment at doses below the current dose level as part of the dose-escalation process. Additional patients may only be added at a lower dose level provided there is at least 1 patient who has achieved a partial response (PR or better). No more than 10 patients in total can be treated at any dose level unless ≥3 of the 10 patients have achieved a PR or better.

During Part 2 (dose expansion), patients will be monitored for safety using the same DLT criteria employed during dose-escalation. If during the treatment period, >30% of patients experience safety events that would meet the criteria that define a DLT in the dose-escalation phase of the study, enrolment in the expansion cohort(s) may be paused and the study data reviewed to determine whether additional monitoring or other action (such as alternate dose levels) should be evaluated prior to further enrolment.

A maximum of 80 patients (up to 50 patients in Part 1 and up to 30 patients in Part 2) may be enrolled at approximately 10 study sites in Part 1 and 10 study sites in Part 2.

Example 5: Summary of ADCx25 Treatment Safety and Efficacy Studies

Study Design

Phase 1, open-label, multicenter dose-escalation (part 1) and dose-expansion (part 2) study in patients with R/R CD25+AML or ALL.

Patients receive ADCx25 as an intravenous (IV) infusion with a starting dose cohort at 3 µg/kg every 3 weeks (q3w).

In part 1, patients are assigned to treatment using a 3+3 dose-escalation design, based on assessment of dose-limiting toxicities (DLTs) during Cycle 1, to determine the MTD.

Dose frequency in subsequent cohorts may increase to once weekly (qw) based on emerging safety, efficacy, and PK profile.

Part 2 will further evaluate safety, tolerability, PK, and clinical activity at the dose recommended from part 1.

| Key patient inclusion criteria | Key patient exclusion criteria |
|---|---|
| Age 18 years or older | Active graft-versus-host disease |
| Histologically confirmed relapsed or refractory lymphoma, including stage ≥Ib cutaneous T-cell lymphoma | Evidence of myelodysplasia or myeloid leukemia |
| Failed, or intolerant to, any established therapy known to provide clinical benefit at current state of disease | Known history of positive serum human anti-drug antibody, or known allergy to any component of ADCx25 |
| Eastern Cooperative Oncology Group performance status 0 to 2 | History of symptomatic autoimmune disease |
| WBC count <15,000 cells/µL prior to Cycle 1, Day 1. Patients with WBC ≥15,000 cells/µL could receive hydroxyurea to lower WBC count. | Major surgery, chemotherapy, systemic therapy, or radiotherapy within 14 days prior to Day 1 treatment |
| | Autologous or allogenic transplant within the 60 days prior to screening |

Results

Patient Characteristics

As of Oct. 31, 2017, 33 patients have been treated with ADCx25. Baseline CD25 expression was present in 5% to 100% of local blast cells.

Safety Data

No DLTs were observed up to the highest evaluated q3w dose of 92 µg/kg.

Upon switching to weekly dosing, one DLT (maculopapular rash) was reported in the 30 µg/kg dose group.

During exposure, a total of 391 treatment-emergent adverse events (TEAEs) were reported in 31/33 (94%) patients.

Most common TEAEs were fatigue (n=10) and nausea (n=8) followed by febrile neutropenia and pneumonia (both n=7).

A summary of Grade ≥3 TEAEs that occurred in ≥10% patients are presented in the table below.

Summary of Grade ≥3 Treatment-Emergent Adverse Events (TEAEs):

| | Dose Escalation | | | | | | | | | | Total |
|---|---|---|---|---|---|---|---|---|---|---|---|
| | q3w | | | | | | | | qw | | |
| | 3 µg/kg N = 4 | 6 µg/kg N = 3 | 12 µg/kg N = 3 | 22 µg/kg N = 3 | 32 µg/kg N = 3 | 52 µg/kg N = 3 | 72 µg/kg N = 3 | 92 µg/kg N = 4 | 30 µg/kg N = 6 | 37.5 µg/kg N = 1 | N = 33 (%) |
| Any TEAE for Grade ≥ 3 | 1 | 2 | 3 | 3 | 3 | 3 | 3 | 3 | 6 | 0 | 27 (818) |
| Febrile neutropenia | 0 | 0 | 2 | 0 | 1 | 0 | 1 | 0 | 3 | 0 | 7 (21.2) |
| Thrombocytopenia | 0 | 0 | 1 | 1 | 0 | 0 | 1 | 0 | 2 | 0 | 5 (15.2) |
| Fatigue | 0 | 0 | 0 | 1 | 0 | 1 | 1 | 1 | 0 | 0 | 4 (12.1) |
| Neutrophil count decreased | 0 | 1 | 0 | 0 | 0 | 1 | 1 | 0 | 1 | 0 | 4 (12.1) |
| Pneumonia | 0 | 1 | 1 | 0 | 0 | 0 | 1 | 0 | 1 | 0 | 4 (12.1) |

Grade ≥3 TEAEs were reported by 27/33 (81.8%) patients

Eight deaths from TEAEs were recorded (disease progression and AML [both n=3], and cardiac arrest and pneumonia [both n=1]). One case each of increased QTc and palpitations was evaluated to be infusion-related by the investigator. Four patients experienced TEAEs leading to a dose delay or reduction (2 cases of skin rash, 1 case each of pericarditis and supraventricular tachycardia). Three patients discontinued treatment due to Grade 2 and 3 skin rash (1 and 2 cases, respectively) and 1 patient due to Grade 3 gamma-glutamyltransferase increase. In 6 patients who underwent prior allogeneic stem cell transplantation, no cases of graft-versus-host disease were observed.

In a separate study of ADCx25 in patients with Hodgkin lymphoma, there have been 2 reports of Guillain-Barré syndrome and 1 report of polyradiculopathy. To date, no such cases have been observed in patients with leukemia treated with ADCx25.

Efficacy Data

One patient had complete response with incomplete blood count recovery.

Transient C025+ blast clearance in 2 patients who received 2 and 7 cycles, respectively, of ADCx25 32 µg/kg q3w, was observed, supporting on-target activity of ADCx25. One patient had 6.25% 0025+ blasts in the marrow prior to Cycle 1, which was reduced to 0% after 2 cycles of ADCx25, despite overall disease progression.

A second patient had 10% 0025+ blasts in the marrow prior to Cycle 1, which was reduced to 0% after 2 cycles, with a total marrow blast count of 5%. 0025+ blasts remained at 0% until after cycle 7 when the patient had disease progression with 0025+ blasts.

PK Data

Figure 4:
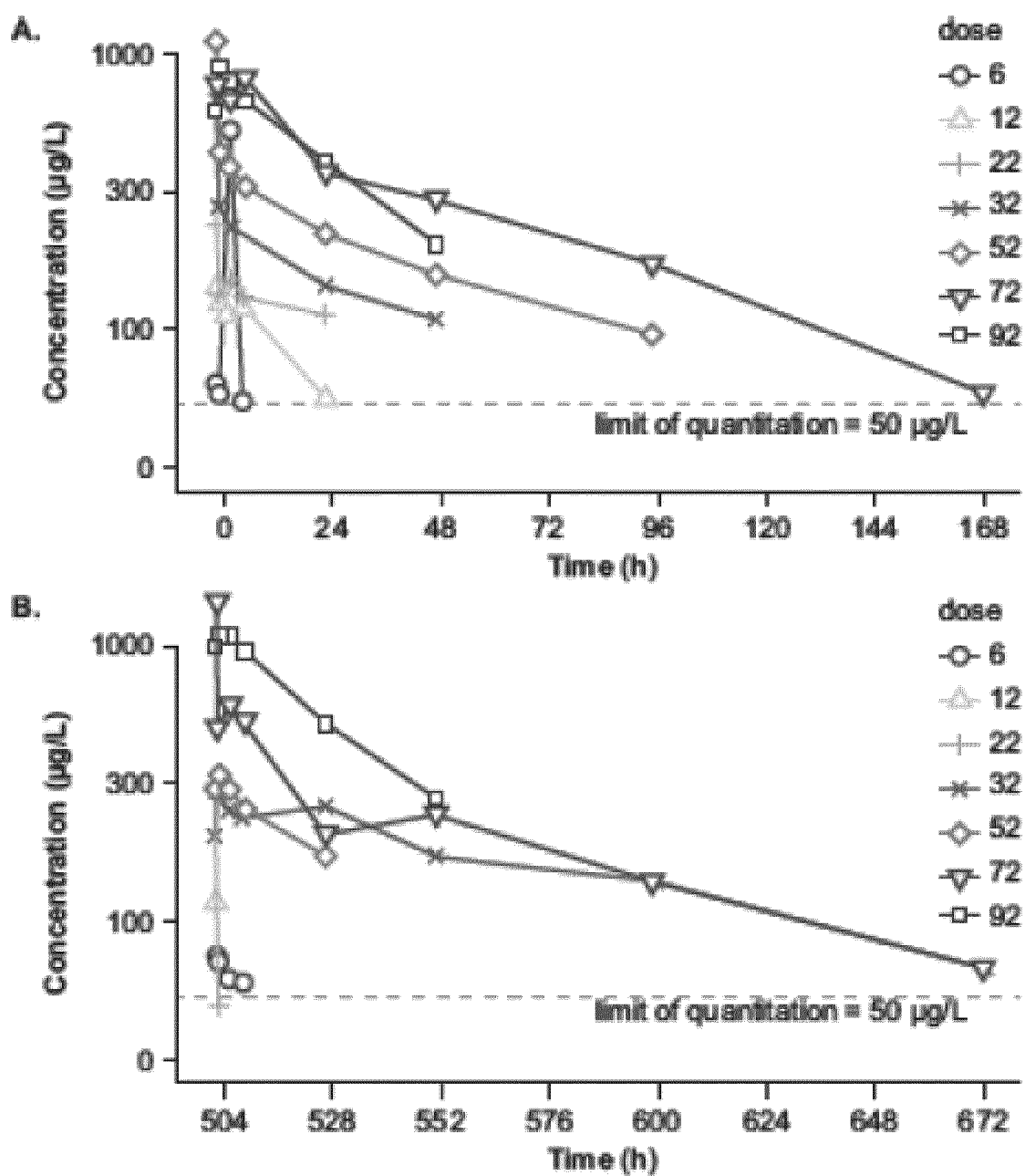

PK data show increasing concentrations of PBD-conjugated antibody with dose (see FIG. 4).

No drug accumulation is apparent with a q3w regimen. Rapid systemic clearance of the drug with levels below limit of quantitation suggests that q3w dosing may be insufficient for therapeutic efficacy.

Conclusions

In this ongoing Phase 1 study in patients with CD25+R/R AML or ALL, single-agent ADCx25 has shown an acceptable safety profile thus far.

The study is continuing to explore the safety profile of weekly dosing.

Example 6: Pharmokinetics of ADC in Patients

At least one dose of ADC was administered to 48 patients with Relapsed or Refractory Non Hodgkin Lymphoma (4 at 15 µg/kg, 4 at 30 µg/kg, 4 at 60 µg/kg, 5 at 90 µg/kg, 12 at 120 µg/kg, 3 at 150 µg/kg and 17 at 200 µg/kg). Cohorts at 120 µg/kg and 200 µg/kg were expanded to further explore the early efficacy signals seen at those dose levels.

Emerging safety, pharmacokinetic and efficacy data suggest that repetitive dosing every three weeks is not well tolerated or necessary at doses of 120 µg/kg and higher. Twelve patients have been treated at 120 µg/kg (10 DLBCL, 1 FL and 1 MCL) with 4 patients attaining complete remission (CR) and 2 partial remission (PR). The 6 responding patients have received 3-7 infusions of ADC with 4 of these patients having at least one dose delay due to adverse events (fatigue (2), edema (3), muscle pain (2), rash (1), Elevated GGT and alkaline phosphatase (1)). Two patients were discontinued from treatment due to adverse events in this cohort (both had attained CR).

At 150 µg/kg, the three initial patients received either 2 or 3 cycles of ADCT before side effects necessitated dose delay which eventually led to removal from the study since the toxicities were slow to resolve.

The first six evaluable patients treated on the 200 µg/kg cohort with dose administered every three weeks attained CR(5) or PR(1) on first restaging scans at the end of Cycle 2 (after second dose). However, all patients had some evidence of toxicity at the end of Cycle 2 (4 patients) or cycle 3 (1 patient). The pharmacokinetic profiles for the first two cycles for the initial 3 patients treated on the 200 µg/kg cohort indicated that the AUC and Cmax at the 200 µg/kg dose level are significantly higher than seen at lower doses. The trough levels at the end of Cycle 1 appear to be in the range of 500-1000 ng/ml.

In view of the emerging safety profile, it is proposed to modify the dosage regimes for future subjects at doses of 120 µg/kg or higher so that they are tapered and/or elongated dosage regimes as described herein. In particular, the following tapered and elongated dosage regimes will be utilised:

A. 120 µg/kg: Dosing every 3 weeks for 2 cycles. Patients with at least SD after the second cycle continue treatment at a reduced dose of 60 µg/kg q6 weeks, beginning 6 weeks after Cycle 2 infusion.
  B. 150 µg/kg: Dosing every 3 weeks for 2 cycles. Patients with at least SD after the second cycle continue treatment at a reduced dose of 60 µg/kg q6 weeks, beginning 6 weeks after Cycle 2 infusion.
  C. 200 µg/kg: Dosing every 6 weeks for 2 cycles. For patients with at least SD 6 weeks after Cycle 2, continue treatment at a reduced dose of 60 µg/kg q6 weeks, beginning 6 weeks after Cycle 2 infusion.
  D. 200 µg/kg: Dosing every 6 weeks. For patients with at least SD 6 weeks after Cycle 1, continue treatment at a reduced dose of 60 µg/kg every 6 weeks beginning 6 weeks after Cycle 1 infusion.

A full clinical study protocol for the 3-week treatment cycle with a single-dose of ADCx25 administered on day 1 is publically available at www.clinical trials.gov, having the ClinicalTrials.gov unique identifier: NCT02432235 (27 Apr. 2017 update).

Example 7: Synopsis of Tapered and/or Elongated Dosage Protocol

Indication

Patients with relapsed or refractory non-Hodgkin Lymphoma (NHL) who have failed, or are intolerant to, any established therapy; or for whom no other treatment options are available, in the opinion of the Investigator.

The Dose Escalation Steering Committee (DESC) will determine which histologic sub-types will be investigated in Part 2 of the study based on the emerging efficacy and tolerability profile from part 1.

NHL defined as:
Diffuse large B-cell lymphoma (DLBCL)
Follicular lymphoma (FL)
Chronic lymphocytic leukemia (CLL)
Mantle cell lymphoma (MCL)
Marginal Zone B-cell Lymphoma (MZBCL)
Burkitt's lymphoma (BL)
Lymphoplasmacytic lymphoma (Waldenstrom macroglobulinemia [WM]).

Objectives

Primary Objectives:
Evaluate the safety and tolerability, and determine, as appropriate, the maximum tolerated dose (MTD) of ADC in patients with relapsed or refractory NHL (Part 1).
Determine the recommended dose(s) of ADC for Part 2 (expansion).
Evaluate the safety and tolerability of ADC in Part 2 (expansion) at the dose level(s) recommended in Part 1.

Secondary Objectives:
Evaluate the clinical activity of ADC as measured by overall response rate (ORR), duration of response (DOR), progression-free survival (PFS), and overall survival (OS).
Characterize the pharmacokinetic (PK) profile of ADC (total antibody; drug to-antibody ratio [DAR]≥0), PBD-conjugated antibody (DAR≥1), and free warhead.
Evaluate anti-drug antibodies (ADAs) in blood before, during, and after treatment with ADC.

Efficacy Assessment

Disease assessments will be conducted within 6 days prior to Day 1 of Cycles 3 and 5 and thereafter every third cycle (i.e., Cycles 8, 11, 14, etc.), until disease progression, or more frequently, if clinically indicated. The same methods used at Screening which identify sites of disease should be used uniformly for all subsequent assessments. If PET-CT is positive, subsequent diagnostic CT and MRI are not needed unless clinically indicated. PET-CT is not required if a PET-CT examination at Screening was negative.

For patients who have reduced dosing frequency and are following a 6 week schedule, disease assessments should occur approximately 6 weeks and 12 weeks after Cycle 1 Day 1, and thereafter at least every 12 weeks. It is understood that there will be a ±6 day window for restaging of these patients.

The patient's response to treatment will be determined by the Investigator as complete response (CR), partial response (PR), stable disease (SD), or progressive disease (PD), based on the 2014 Lugano Classification Criteria.

PK Assessment

The PK profile of ADC (total antibody; DAR≥0), PBD-conjugated antibody (DAR≥1), and free warhead will be assessed using measures from validated bioanalytical methods. The PK profile will include determination of standard PK parameters (e.g., maximum concentration [Cmax], time to Cmax [Tmax]).

The following pharmacodynamic and other exploratory assessments will be performed at various time points in the study:
Immunohistochemistry (archival tumor tissue or pre-treatment tumor biopsies in consenting patients) for CD25 protein expression
Level of ADAs against ADC in serum.
Analysis of peripheral WBC populations and CD marker panel expression (CD25, CD20, CD21, CD22), before, during, and after treatment with ADC (US only).
Serum concentrations of ADC and free warhead will be determined. The QTc interval will also be measured.

Safety Assessment

Safety will be assessed based on the evaluation of adverse events (AEs), serious AEs (SAEs), treatment discontinuations due to AEs, dose limiting toxicity(s) (DLTs), periodic 12-lead electrocardiogram (ECG) recordings, physical examinations, vital signs measurements, ECOG performance status, and hematology, coagulation panel and pregnancy testing (for women of child-bearing potential), biochemistry, and urinalysis test results obtained at various timepoints during the study. Adverse events will be graded according to CTCAE Version 4.0 (v4.03, published Jun. 14, 2010; NIH Publication No. 09-5410).

Product Dosage and Mode of Administration

ADC is a sterile formulation containing PBD-conjugated humanized monoclonal IgG1 antibody (DAR≥1), humanized monoclonal IgG1 antibody (DAR=0), and drug-linker. It is provided pre-formulated in 10 mL single-use, glass vials containing approximately 16 mg ADC per vial (deliverable volume 3.2 mL, with an additional 0.3 mL overfill at 5 mg/mL). Patients will receive a 1-hour intravenous (IV) infusion of ADC on Day 1 of Cycle 1. If ADC is well tolerated after the first infusion, the infusion duration may be shortened to 30 minutes for subsequent cycles for that patient, at the Investigator's discretion.

Dose Escalation Design

In Part 1, patients will be assigned to treatment with ADCx25 at escalating doses according to a 3+3 study design. The initial dose of ADCx25 will be 15 µg/kg (Dose Level 1), and the highest allowed dose will be 300 µg/kg.

Further dose levels and schedules evaluated include the following:

A. 120 µg/kg: Dosing every 3 weeks for 2 cycles. Patients with at least SD after the second cycle continue treatment at a reduced dose of 60 µg/kg q6 weeks, beginning 6 weeks after Cycle 2 infusion.

B. 150 µg/kg: Dosing every 3 weeks for 2 cycles. Patients with at least SD after the second cycle continue treatment at a reduced dose of 60 µg/kg q6 weeks, beginning 6 weeks after Cycle 2 infusion.

C. 200 µg/kg: Dosing every 6 weeks for 2 cycles. For patients with at least SD 6 weeks after Cycle 2, continue treatment at a reduced dose of 60 µg/kg q6 weeks, beginning 6 weeks after Cycle 2 infusion.

D. 200 µg/kg: Dosing every 6 weeks. For patients with at least SD 6 weeks after Cycle 1, continue treatment at a reduced dose of 60 µg/kg every 6 weeks beginning 6 weeks after Cycle 1 infusion.

The first patient enrolled into the study at 15 µg/kg (Dose Level 1) must be observed for 7 days for occurrence of AEs prior to treating the second patient in the study. The DLT observation period for dose escalation is 1 cycle.

For each dose level, if none of the first 3 patients at that level experiences a DLT, new patients may be entered at the next higher dose level. If 1 of 3 patients experiences a DLT, up to 3 more patients are to be treated at that same dose level. If none of the additional 3 patients at that dose level experiences a DLT, new patients may then be entered at the next higher dose level. However, if 1 or more of the additional 3 patients experiences a DLT, then no further patients are to be started at that dose level and the preceding dose is identified as the MTD. The MTD is therefore defined as the highest dose level at which none of the first 3 treated patients, or no more than 1 of the first 6 treated patients, experiences a DLT.

The study will be continuously monitored for safety and early stopping for successful identification of the MTD.

Dose Expansion Design

In Part 2, (expansion), patients will be assigned to dose level(s) and/or schedule(s) of ADCx25 identified in Part 1 based on evolving safety, efficacy and pharmacokinetic data.

The population in Part 2 expansion may be restricted to specific histologies based on both signals of activity and the safety observed in Part 1.

Further, dose levels and schedules evaluated in Part 2 may include the regimes A, B, C. and D as described for Part 1, above.

Example 8: Summary of ADCx25 Treatment Safety and Efficacy Studies

Study Design

In this Phase 1, open-label, multicenter study, eligible patients (see table below) with R/R HL or NHL receive 1-hour intravenous infusions of ADCx25 every 3 weeks (=1 treatment cycle).

| Key patient inclusion criteria | Key patient exclusion criteria |
| --- | --- |
| Age 18 years or older | Active graft-versus-host disease |
| Histologically confirmed relapsed or refractory lymphoma, including stage ≥1b cutaneous T-cell lymphoma | Evidence of myelodysplasia or myeloid leukemia |
| Failed, or intolerant to, any established therapy known to provide clinical benefit at current state of disease | Known history of positive serum human anti-drug antibody, or known allergy to any component of ADCx25 |
| Eastern Cooperative Oncology Group performance status 0 to 2 | History of symptomatic autoimmune disease Major surgery, chemotherapy, systemic therapy, or radiotherapy within 14 days prior to Day 1 treatment |

In part 1, the initial cohort received a starting dose of 3 µg/kg, with subsequent cohorts enrolled at escalating doses up to a maximum of 300 µg/kg according to a continual reassessment method, which allows expansion at different doses for different lymphoma subtypes.

The dose-limiting toxicity (DLT) observation period is Cycle 1, with cumulative DLTs occurring through Cycle 3 incorporated into the adaptive dose-escalation algorithm No more than 10 patients can be treated at any dose level unless at least 3/10 patients have documented a partial response or better The MTD will be the highest dose that has at least a 60% probability of the DLT rate being <30%.

Part 2 will further evaluate safety, tolerability, PK.

Results

Patient Characteristics

As of Nov. 1, 2017, 86 patients have been treated with ADCx25.

Median number of cycles: 2 [min, max: 1, 15], with a median treatment duration of 43 days [min, max: 7, 375]

71 patients have been treated with doses ranging from 3 to 150 µg/kg during part 1. 15 patients have been treated with dose 45 µg/kg in part 2. Histological subtypes treated include HL, n=50 and NHL, n=36.

Safety Data

DLTs have been reported in 4 patients: Oral mucositis and small bowel enteritis at 20 µg/kg, Elevated creatine phosphokinase at 30 µg/kg, Maculopapular rash and pruritus at 30 µg/kg, Lip ulceration and skin infection at 45 µg/kg.

The most common treatment-emergent adverse events (TEAEs) were fatigue, rash, elevated gamma-glutamyltransferase and pyrexia. The most common Grade ≥3 TEAEs were elevated gamma-glutamyltransferase, decreased platelet count, elevated alanine aminotransferase, anemia and rash.

Drug dose was delayed or reduced following a TEAE for 28/86 patients (32.6%). TEAEs leading to treatment discontinuation occurred in 12/86 patients (14.0%). There have been 3 cases of autoimmune neurotoxicity: Two cases of Guillain-Barré syndrome (GBS); one case of polyradiculopathy in a patient with concurrent thyroiditis.

The MTD has not been reached, but no further dose escalation is planned for patients with HL.

Any Grade TEAEs (safety analysis set; N=86):

| TEAEs (any grade) reported by ≥20% of patients, n (%) | ADCx25 dose (µg/kg) q3w | | | | | | |
| --- | --- | --- | --- | --- | --- | --- | --- |
| | ≤30 µg/kg (n = 16) | 45a (n = 30) | 60 (n = 20) | 80 (n = 15) | 100 (n = 3) | 150 (n = 2) | Total (N = 86) |
| Patients with TEAE (any grade) | 15 (93.8) | 26 (86.7) | 20 (100) | 15 (100) | 3 (100) | 2 (100) | 81 (94.2) |
| Fatigue | 4 (25.0) | 7 (23.3) | 9 (45.0) | 5 (33.3) | 1 (33.3) | 0 | 26 (30.2) |
| Rash maculopapular | 6 (37.5) | 5 (16.7) | 7 (35.0) | 4 (26.7) | 0 | 0 | 22 (25.6) |

-continued

| TEAEs (any grade) reported by ≥20% of patients, n (%) | ADCx25 dose (µg/kg) q3w | | | | | | |
|---|---|---|---|---|---|---|---|
| | ≤30 µg/kg (n = 16) | 45a (n = 30) | 60 (n = 20) | 80 (n = 15) | 100 (n = 3) | 150 (n = 2) | Total (N = 86) |
| Gamma-glutamyltransferase increased | 3 (18.8) | 4 (13.3) | 5 (25.0) | 5 (33.3) | 1 (33.3) | 1 (50.0) | 19 (22.1) |
| Pyrexia | 2 (12.5) | 5 (16.7) | 6 (30.0) | 5 (33.3) | 0 | 0 | 18 (20.9) |

Grade ≥3 TEAEs (safety analysis set; N=86):

| TEAEs (Grade ≥3) reported by ≥5% of patients, n (%) | ADCx25 dose (µg/kg) q3w | | | | | | |
|---|---|---|---|---|---|---|---|
| | ≤30 µg/kg (n = 16) | 45a (n = 30) | 60 (n = 20) | 80 (n = 15) | 100 (n = 3) | 150 (n = 2) | Total (N = 86) |
| Patients with TEAE Grade ≥3 | 10 (62.5) | 12 (40.0) | 11 (550) | 13 (86.7) | 3 (100) | 2 (100) | 51 (59.3) |
| Gamma-glutamyltransferase increased | 2 (12.5) | 1 (3.3) | 3 (150) | 4 (26.7) | 0 | 1 (50.0) | 11 (128) |
| Platelet count decreased | 1 (6.3) | 1 (3.3) | 2 (10.0) | 2 (13.3) | 1 (33.3) | 1 (50.0) | 8 (9.3) |
| Alanine aminotransferase increased | 0 | 1 (3.3) | 2 (10.0) | 1 (6.7) | 0 | 1 (50.0) | 5 (5.8) |
| Anemia | 2 (12.5) | 1 (3.3) | 0 | 2 (13.3) | 0 | 0 | 5 (5.8) |
| Rash maculopapular | 4 (25.0) | 0 | 0 | 1 (6.7) | 0 | 0 | 5 (5.8) |

Efficacy Data

Response data for 35 patients with HL give ORR for all doses was 71.4% (25/35 patients).

27 patients with HL have been treated with doses ≥45 µg/kg in part 1, with an ORR of 77.8% (21/27) that comprises a CR rate of 44.4% (12/27) and PR rate of 33.3% (9/27).

Of the 12 patients with HL who have been treated with dose 45 µg/kg in parts 1 and 2, 6 patients each have achieved a CR or PR, respectively, resulting in an ORR of 100% (12/12).

In part 1 and 2 at doses ≥45 µg/kg, a CR or PR was achieved by:

21/27 patients (77.8%) with prior brentuximab vedotin

13/18 patients (72.2%) with prior checkpoint inhibitor

9/14 patients (64.3%) who had prior stem cell transplantation

4/8 patients (50.0%) who had received all three of the above treatments.

Median duration of response was 5.1 months.

Responses were also seen in patients with NHL (all doses; partial response: 18.2% [6/33]; complete response: 6.1% [2/33]).

Dose escalation will continue for patients with NHL.

Best overall responses a (efficacy analysis set):

| | HL | | | NHL | |
|---|---|---|---|---|---|
| n (%) | Part 1 only: ≥45 µg/kg (n = 27) | Parts 1 & 2: All doses (n = 35) | Parts 1 & 2: 45 µg/kg (n = 12) | T-cell lymphoma (n = 12) | B-cell lymphoma (n = 21) |
| OR | 21 (778) | 25 (71.4) | 12 (100) | 4 (333) | 4 (190) |
| CR | 12 (444) | 14 (400) | 6 (50) | 0 | 2 (95) |
| PR | 9 (33.3) | 11 (314) | 6 (50) | 4 (33.3) | 2 (9.5) |
| SD | 1 (37) | 4 (114) | 0 | 1 (83) | 0 |
| PD | 4 (14.8) | 4 (11.4) | 0 | 6 (50.0) | 15 (71.4) |
| NE | 1 (3.7) | 2 (5.7) | 0 | 1 (8.3) | 2 (9.5) |

Conclusions

In patients with R/R HL, ADCx25 was active with the safety profile as described during dose escalation and expansion.

The ORR in this heavily pretreated population is very promising and HL expansion cohorts are underway.

Dose escalation will continue to identify the MTD in NHL, with planned subtype-specific expansion cohorts at the MTD.

ADCx25 has shown high levels of activity in HL, T- and B-cell lymphomas.

Characterization of the dosing regimen is ongoing to maximize the therapeutic window for Phase 2 in HL.

Example 9: Pharmacometric Characterization for Safety of ADCx25 in Patients with Hematologic Malignancies in a Phase 1 Trial Aims To optimize future studies of ADCx25, the relationship between drug exposure and treatment emergent adverse events (TEAE) was analysed.

Methods

Exposure was determined using a population pharmacokinetic (PPK) model of conjugated antibody (cAb) and total antibody (tAb) disposition, comprising shared terms for clearance (linear and non-linear, time-dependent) and volume. The model was fitted by first order conditional estimation using NONMEM v7.3.0 (ICON Solutions). Parameters for peak ($C_{max}$) and average ($C_{avg}$) exposure were derived for each patient and associated to occurrence and severity of TEAE categories for autoimmune-mediated, edema/effusion, fatigue, liver function test (LFT), neurological, pain, and skin. Kaplan-Meier curves for event-free time (EFT) to TEAE were drawn for patients grouped according to low and high exposure. Testing for significance of covariates included sex, race, age, weight, disease subtype, body mass index, body surface area, performance status (ECOG), tumor size and number of prior therapies, and was performed using Kaplan-Meier and the associated log rank test.

Results

Measures of cAb (n=938) and tAb (n=963) in serum were assessed from 77 patients given intravenous Cami-T doses of 3-150 µg/kg Q3W. Unconjugated PBD toxin levels were below the 10 pg/mL lower limit of quantification for most patients and not used in analysis. Modeling yielded a linear clearance of 0.674 L/day, deconjugation clearance of 0.210 L/day, and nonlinear terms for $V_{max}$=0.319 mg/day, $K_m$=0.169 µg/mL, and $K_{des}$=0.00113 day$^{-1}$. For TEAEs grade ≥1, significant differences in EFT by cAb exposure (high/low) during Cycle 1 or at any time were observed for LFT (Cycle 1), pain (Cycle 1), and skin-related toxicities (any cycle) (Table 1).

TABLE 1

Log Rank Test (p-value) and mEFT for treatment emergent adverse events (TEAEs) Grade ≥1 and conjugated antibody (cAb) Exposure

| TEAEs grade ≥1 | cAb exposure (high vs low) | p-value | mEFT for high exposure (days) | mEFT for low exposure (days) |
|---|---|---|---|---|
| LFT | Cycle 1 $C_{avg}$ | 0.027 | 146 | NR |
| LFT | Cycle 1 $C_{max}$ | 0.036 | NR | NR |
| Pain | Cycle 1 $C_{avg}$ | 0.048 | NR | NR |
| Skin | max $C_{avg}$ | 0.024 | 37 | 234 |
| Skin | max $C_{max}$ | 0.0096 | 35 | 234 |
| Edema/Effusion | max $C_{avg}$ | 0.081 | NR | NR |

LFT, liver function test; mEFT, median event-free time; NR, not reached

Potentially clinically important, but not significant was edema/effusion. Covariates with a significant effect on TEAEs grade ≥1 included ECOG (0 vs ≥1) on autoimmune-mediated toxicity (p=0.007, median EFTs [mEFTs] not reached), race effect (White vs non-White) on edema/effusion (p=0.035, mEFTs not reached) and on neurological toxicity (p=0.042, mEFTs not reached). For TEAEs grade ≥3, no significant differences in EFT by cAb exposure were observed.

CONCLUSION

Using an integrated PPK model, individual patient drug exposures were obtained and used as drivers of observed safety effects in an exposure-response analysis. Data indicated apparent exposure relatedness to mild severities of LFT, pain, and skin-related toxicities following ADCx25 treatment of patients with R/R lymphomas. Development of a parametric model to predict time-to-event for various dosage regimens is planned to optimize the benefit/risk ratio in these patients

The invention claimed is:

1. A method of treating a proliferative disease in a subject, said method comprising administering to a subject a CD25-ADC, wherein the CD25-ADC is administered to the subject in a dosage regime where the dose is reduced following the second treatment cycle, wherein each treatment cycle is 3 weeks and the reduced dose is 25 to 55 μg/kg, and wherein the CD25-ADC has the chemical structure:

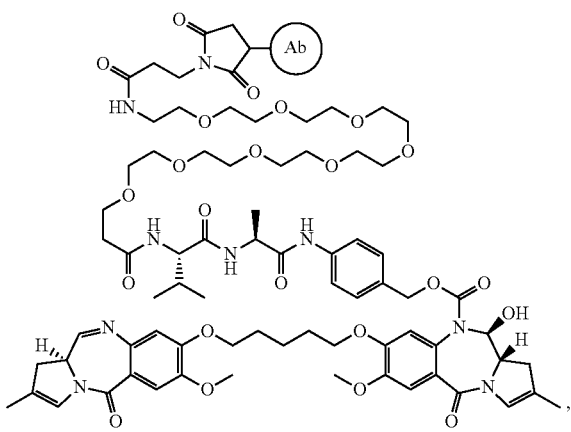

where the Ab is a CD25 antibody comprising:
a VH domain comprising a VH CDR1 with the amino acid sequence of SEQ ID NO:3, a VH CDR2 with the amino acid sequence of SEQ ID NO:4, and a VH CDR3 with the amino acid sequence of SEQ ID NO:5, and
a VL domain comprising a VL CDR1 with the amino acid sequence of SEQ ID NO:6, a VL CDR2 with the amino acid sequence of SEQ ID NO:7, and a VL CDR3 with the amino acid sequence of SEQ ID NO:8,
and the DAR (drug to antibody ratio) is between 1 and 8.

2. The method according to claim 1, wherein Ab comprises a VH domain having the amino acid sequence of SEQ ID NO:1 and a VL domain having the amino acid sequence of SEQ ID NO:2.

3. The method according to claim 1, wherein the starting dose of CD25-ADC is reduced no more than once during the dosage regime.

4. The method according to claim 1, wherein the starting dose is 40 to 50 μg/kg.

5. The method according to claim 3, wherein the starting dose is about 45 μg/kg.

6. The method according to claim 1, wherein the starting dose is 55 to 65 μg/kg.

7. The method according to claim 6, wherein the starting dose is about 60 μg/kg.

8. The method according to claim 1, wherein the starting dose is 75 to 85 μg/kg.

9. The method according to claim 8, wherein the starting dose is about 80 μg/kg.

10. The method according to claim 1, wherein the reduced dose is 25 to 35 μg/kg.

11. The method according to claim 10, wherein the reduced dose is about 30 μg/kg.

12. The method according to claim 1, wherein the reduced dose is 35 to 45 μg/kg.

13. The method according to claim 12, wherein the reduced dose is about 40 μg/kg.

14. The method according to claim 1, wherein the reduced dose is 45 to 55 μg/kg.

15. The method according to claim 14, wherein the reduced dose is about 50 μg/kg.

16. The method according to claim 1, wherein about 40 to 50 μg/kg of CD25-ADC are administered for two, 3-week treatment cycles, followed by subsequent 3-week cycles of 25 to 35 μg/kg beginning 3 weeks after the cycle 2 administration.

17. The method according to claim 1, wherein about 45 μg/kg of CD25-ADC are administered for two, 3-week treatment cycles, followed by subsequent 3-week cycles of 30 μg/kg beginning 3 weeks after the cycle 2 administration.

18. The method according to claim 1, wherein the proliferative disease is Hodgkin's lymphoma.

19. The method according to claim 1, wherein the proliferative disease is non-Hodgkin's lymphoma of B-cell or T-cell lineage.

20. The method according to claim 1, wherein the non-Hodgkin's lymphoma is either:
  (a) a B-cell lineage lymphoma selected from diffuse large B-cell lymphoma (DLBCL), follicular lymphoma, (FL), Mantle Cell lymphoma (MCL), chronic lymphatic lymphoma (CLL), and Marginal Zone B-cell lymphoma (MZBL); or
  (b) a T-cell lineage lymphoma selected from Extranodal T cell lymphoma, Cutaneous T-cell lymphomas (Sézary syndrome and Mycosis fungoides), Anaplastic large cell lymphoma, T-cell lymphoblastic lymphoma, including acute T-cell lymphoblastic lymphoma (ATLL), and Angioimmunoblastic T-cell lymphoma.

21. The method according to claim 1, wherein the proliferative disease is resistant, relapsed, or refractory.

22. The method according to claim 1, wherein the subject is human.

23. The method according to claim 1, further comprising administering a chemotherapeutic agent in combination with the CD25-ADC.

24. The method according to claim 1, wherein the CD25-ADC is administered in combination with a steroid.

25. The method according to claim 24, wherein the steroid is dexamethasone.

* * * * *

UNITED STATES PATENT AND TRADEMARK OFFICE
CERTIFICATE OF CORRECTION

| | |
|---|---|
| PATENT NO. | : 11,426,467 B2 |
| APPLICATION NO. | : 16/622663 |
| DATED | : August 30, 2022 |
| INVENTOR(S) | : Jay Marshall Feingold and Jens Wuerthner |

It is certified that error appears in the above-identified patent and that said Letters Patent is hereby corrected as shown below:

In the Claims

Column 95, Line 1 (Claim 20):
"The method according to claim 1"
Should be replaced with:
-- "The method according to claim 19" --.

Signed and Sealed this
Twentieth Day of December, 2022

Katherine Kelly Vidal
*Director of the United States Patent and Trademark Office*

SEQUENCE LISTING

```
<160> NUMBER OF SEQ ID NOS: 10

<210> SEQ ID NO 1
<211> LENGTH: 127
<212> TYPE: PRT
<213> ORGANISM: Artificial Sequence
<220> FEATURE:
<223> OTHER INFORMATION: AB12 VH

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ile Ile Asn Trp Val Arg Gln Ala Pro Gly Gln Gly Leu Glu Trp Met
        35                  40                  45

Gly Arg Ile Ile Pro Ile Leu Gly Val Glu Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Asp Trp Phe Asp Tyr Trp Gly Gln Gly Thr Leu Val Thr
```

```
                    100                 105                 110
Val Ser Ser Ala Ser Thr Lys Gly Pro Ser Val Phe Pro Leu Ala
            115                 120                 125

<210> SEQ ID NO 2
<211> LENGTH: 119
<212> TYPE: PRT
<213> ORGANISM: Artificial Sequence
<220> FEATURE:
<223> OTHER INFORMATION: AB12 VL

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro
        115

<210> SEQ ID NO 3
<211> LENGTH: 5
<212> TYPE: PRT
<213> ORGANISM: Artificial Sequence
<220> FEATURE:
<223> OTHER INFORMATION: VH CDR1

<400> SEQUENCE: 3

Arg Tyr Ile Ile Asn
1               5

<210> SEQ ID NO 4
<211> LENGTH: 17
<212> TYPE: PRT
<213> ORGANISM: Artificial Sequence
<220> FEATURE:
<223> OTHER INFORMATION: VH CDR2

<400> SEQUENCE: 4

Arg Ile Ile Pro Ile Leu Gly Val Glu Asn Tyr Ala Gln Lys Phe Gln
1               5                   10                  15

Gly

<210> SEQ ID NO 5
<211> LENGTH: 6
<212> TYPE: PRT
<213> ORGANISM: Artificial Sequence
<220> FEATURE:
<223> OTHER INFORMATION: VH CDR3

<400> SEQUENCE: 5

Lys Asp Trp Phe Asp Tyr
1               5
```

<210> SEQ ID NO 6
<211> LENGTH: 11
<212> TYPE: PRT
<213> ORGANISM: Artificial Sequence
<220> FEATURE:
<223> OTHER INFORMATION: VL CDR1

<400> SEQUENCE: 6

Arg Ala Ser Gln Ser Val Ser Ser Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: VL CDR2

<400> SEQUENCE: 7

Gly Ala Ser Ser Arg Ala Thr
1               5

<210> SEQ ID NO 8
<211> LENGTH: 9
<212> TYPE: PRT
<213> ORGANISM: Artificial Sequence
<220> FEATURE:
<223> OTHER INFORMATION: VL CDR3

<400> SEQUENCE: 8

Gln Gln Tyr Gly Ser Ser Pro Leu Thr
1               5

<210> SEQ ID NO 9
<211> LENGTH: 447
<212> TYPE: PRT
<213> ORGANISM: Artificial Sequence
<220> FEATURE:
<223> OTHER INFORMATION: Heavy Chain Antibody sequence

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Gly Tyr Glu Asp Ala Met Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Cys Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 10
<211> LENGTH: 214
<212> TYPE: PRT
<213> ORGANISM: Artificial Sequence
<220> FEATURE:
<223> OTHER INFORMATION: Light chain antibody sequence

<400> SEQUENCE: 10

Asp Ile Gln Met Thr Gln Ser Pro Ser Ser Leu Ser Ala Ser Val Gly
1               5                   10                  15

Asp Arg Val Thr Ile Asn Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80
```

```
Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```